(12) United States Patent
Ta et al.

(10) Patent No.: US 9,956,099 B2
(45) Date of Patent: *May 1, 2018

(54) THIN-WALLED SCAFFOLDS HAVING REDUCED CRIMP PROFILE AND CARRYING RADIOPAQUE MARKERS

(71) Applicant: Abbott Cardiovascular Systems Inc., Santa Clara, CA (US)

(72) Inventors: Diem Ta, San Jose, CA (US); Chad Abunassar, San Francisco, CA (US); Senthil Eswaran, Sunnyvale, CA (US); Zhicheng Lin, Palo Alto, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 7 days.

This patent is subject to a terminal disclaimer.

(21) Appl. No.: 14/973,628

(22) Filed: Dec. 17, 2015

(65) Prior Publication Data

US 2017/0172769 A1 Jun. 22, 2017

(51) Int. Cl.
*A61F 2/82* (2013.01)
*A61F 2/915* (2013.01)
*A61F 2/844* (2013.01)
*A61F 2/958* (2013.01)

(52) U.S. Cl.
CPC .............. *A61F 2/915* (2013.01); *A61F 2/844* (2013.01); *A61F 2/958* (2013.01); *A61F 2002/91583* (2013.01); *A61F 2210/0004* (2013.01); *A61F 2250/0098* (2013.01)

(58) Field of Classification Search
CPC ...... A61F 2/82; A61F 2/92; A61F 2/91; A61F 2/9195

USPC ................................................ 623/1.15–1.48
See application file for complete search history.

(56) References Cited

U.S. PATENT DOCUMENTS

| | | | |
|---|---|---|---|
| 6,402,777 B1 | 6/2002 | Globerman et al. | |
| 6,942,681 B2 | 9/2005 | Johnson | |
| 7,731,740 B2 | 6/2010 | LaFont et al. | |
| 8,002,817 B2 | 8/2011 | Limon et al. | |
| 8,062,465 B1 | 11/2011 | Huang et al. | |
| 8,303,644 B2 | 11/2012 | Lord et al. | |
| 8,388,673 B2 * | 3/2013 | Yang ......................... | A61F 2/91 623/1.14 |
| 8,752,261 B2 | 6/2014 | Van Sciver | |
| 9,700,443 B2 | 7/2017 | Lumauig et al. | |
| 2005/0273157 A1 | 12/2005 | Pinchasik | |
| 2007/0100431 A1 | 5/2007 | Bonsignore et al. | |

(Continued)

OTHER PUBLICATIONS

Kajtoch, J., "Strain in the Upsetting Process," Metallurgy and Foundry Engineering, 2007, vol. 33, No. 1, pp. 51-61.

(Continued)

*Primary Examiner* — Suzette J Gherbi
(74) *Attorney, Agent, or Firm* — Squire Patton Boggs (US) LLP

(57) ABSTRACT

A thin-walled scaffold includes a radiopaque marker connected to a link. In a first example, the marker is retained on the strut by a head at one or both ends by swaging. In a second example of a thin-walled scaffold the link is modified to avoid interference during crimping. In a third example a distal end of the thin-walled scaffold is modified to improve deliverability of the thin-walled scaffold. These features are combined in a fourth example.

21 Claims, 28 Drawing Sheets

(56) References Cited

U.S. PATENT DOCUMENTS

| | | |
|---|---|---|
| 2007/0156230 A1 | 7/2007 | Dugan |
| 2007/0239251 A1 | 10/2007 | Prabhu et al. |
| 2008/0009933 A1* | 1/2008 | Ta ............................ A61F 2/856 623/1.11 |
| 2008/0275537 A1* | 11/2008 | Limon ...................... A61F 2/91 623/1.15 |
| 2010/0004735 A1 | 1/2010 | Yang et al. |
| 2010/0274349 A1 | 10/2010 | Lord et al. |
| 2012/0035709 A1 | 2/2012 | Young et al. |
| 2012/0042501 A1 | 2/2012 | Wang et al. |
| 2012/0079706 A1 | 4/2012 | Knott et al. |
| 2012/0102708 A1 | 5/2012 | Strauss et al. |
| 2012/0261858 A1 | 10/2012 | Roberts et al. |
| 2013/0000548 A1 | 1/2013 | Eidenschink et al. |
| 2013/0255853 A1 | 10/2013 | Wang et al. |
| 2013/0310913 A1 | 11/2013 | Wang et al. |
| 2014/0013575 A1 | 1/2014 | Wang et al. |
| 2014/0039604 A1 | 2/2014 | Mikael Trollsas et al. |
| 2014/0096357 A1 | 4/2014 | Wang |
| 2014/0330363 A1 | 11/2014 | Anukhin et al. |
| 2015/0073535 A1* | 3/2015 | Consigny .............. A61L 31/148 623/1.38 |
| 2015/0074975 A1 | 3/2015 | Huang et al. |
| 2015/0282969 A1 | 10/2015 | Pacetti |
| 2015/0306282 A1* | 10/2015 | Scanlon .................. A61L 31/14 623/1.11 |
| 2015/0320577 A1 | 11/2015 | Zheng et al. |
| 2016/0030216 A1 | 2/2016 | Wang |
| 2016/0031150 A1 | 2/2016 | Gada et al. |
| 2016/0038320 A1 | 2/2016 | Wang et al. |
| 2016/0081824 A1 | 3/2016 | Harrington et al. |
| 2016/0228267 A1 | 8/2016 | Pacetti et al. |
| 2016/0278952 A1* | 9/2016 | Ngo ....................... A61F 2/915 |
| 2016/0374840 A9 | 12/2016 | Trollsas et al. |
| 2017/0049592 A1* | 2/2017 | Pacetti ................... A61F 2/915 |
| 2017/0156899 A1* | 6/2017 | Zheng .................... A61F 2/915 |
| 2017/0172768 A1* | 6/2017 | Ta ............................ A61F 2/89 |
| 2017/0172770 A1* | 6/2017 | Ta ............................ A61F 2/915 |

OTHER PUBLICATIONS

International Search Report and Written Opinion mailed in International Patent Application No. PCT/US2016/067023, 18 pages.

* cited by examiner

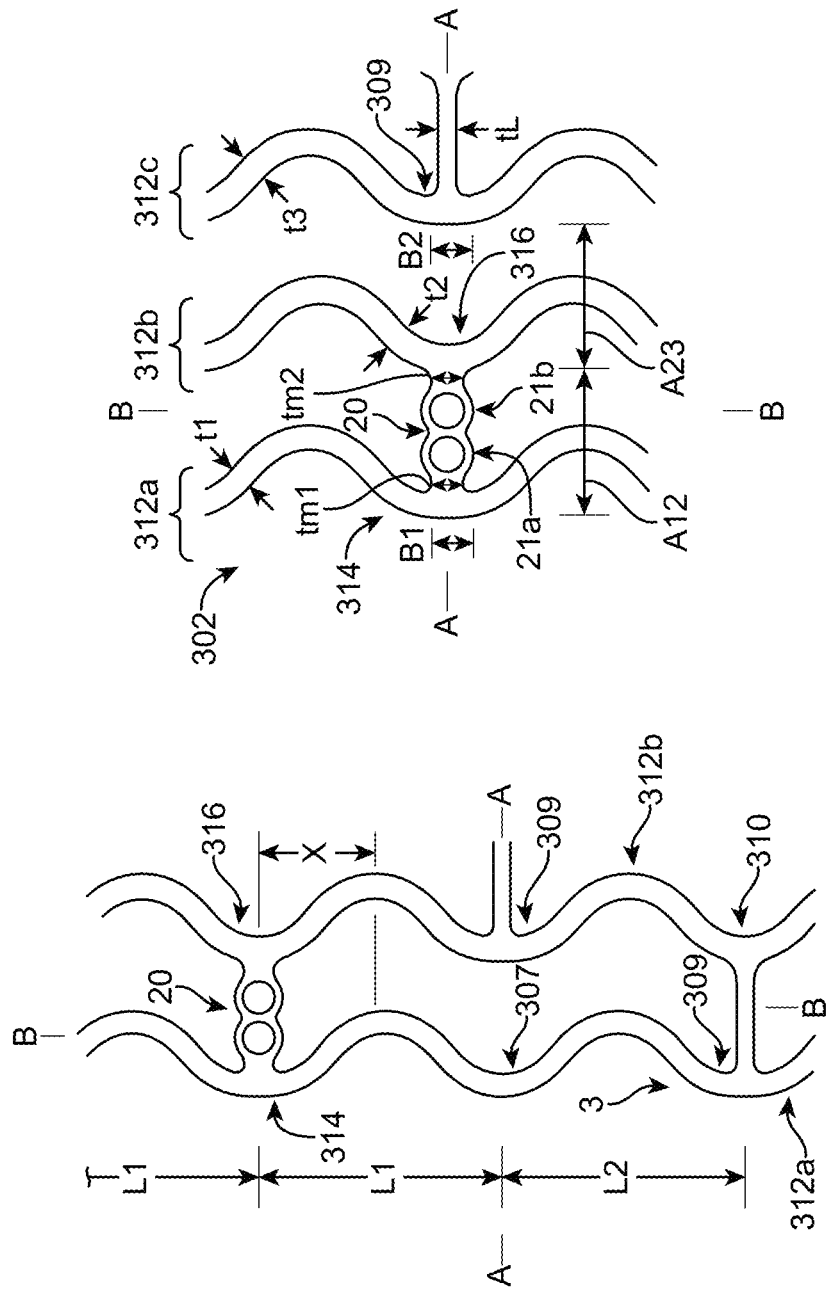

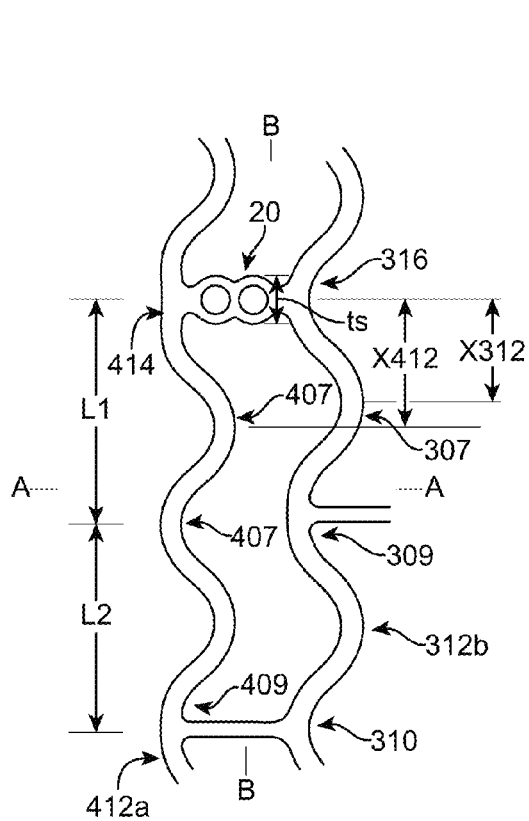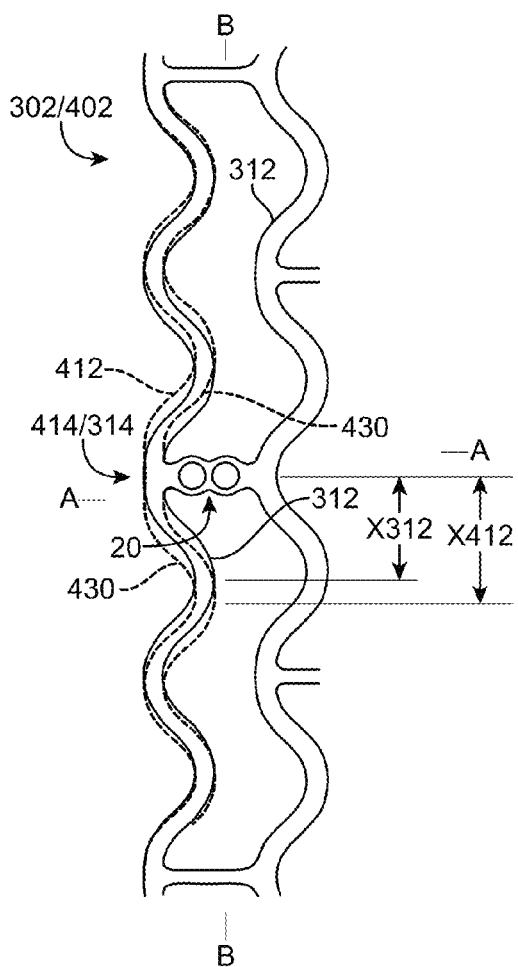
FIG. 4A
FIG. 4B

THIN-WALLED SCAFFOLDS HAVING REDUCED CRIMP PROFILE AND CARRYING RADIOPAQUE MARKERS

BACKGROUND OF THE INVENTION

Field of the Invention

The present invention relates to bioresorbable scaffolds; more particularly, this invention relates to bioresorbable scaffolds for treating an anatomical lumen of the body.

Description of the State of the Art

Radially expandable endoprostheses are artificial devices adapted to be implanted in an anatomical lumen. An "anatomical lumen" refers to a cavity, or duct, of a tubular organ such as a blood vessel, urinary tract, and bile duct. Stents are examples of endoprostheses that are generally cylindrical in shape and function to hold open and sometimes expand a segment of an anatomical lumen. Stents are often used in the treatment of atherosclerotic stenosis in blood vessels. "Stenosis" refers to a narrowing or constriction of the diameter of a bodily passage or orifice. In such treatments, stents reinforce the walls of the blood vessel and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into the anatomical lumen, advancing the catheter in the anatomical lumen to a desired treatment location, expanding the stent at the treatment location, and removing the catheter from the lumen.

Scaffolds and stents traditionally fall into two general categories—balloon expanded and self-expanding. The later type expands (at least partially) to a deployed or expanded state within a vessel when a radial restraint is removed, while the former relies on an externally-applied force to configure it from a crimped or stowed state to the deployed or expanded state.

Self-expanding stents are designed to expand significantly when a radial restraint is removed such that a balloon is often not needed to deploy the stent. Self-expanding stents do not undergo, or undergo relatively no plastic or inelastic deformation when stowed in a sheath or expanded within a lumen (with or without an assisting balloon). Balloon expanded stents or scaffolds, by contrast, undergo a significant plastic or inelastic deformation when both crimped and later deployed by a balloon.

In the case of a balloon expandable stent, the stent is mounted about a balloon portion of a balloon catheter. The stent is compressed or crimped onto the balloon. Crimping may be achieved by use of an iris-type or other form of crimper, such as the crimping machine disclosed and illustrated in US 2012/0042501. A significant amount of plastic or inelastic deformation occurs both when the balloon expandable stent or scaffold is crimped and later deployed by a balloon. At the treatment site within the lumen, the stent is expanded by inflating the balloon.

The stent must be able to satisfy a number of basic, functional requirements. The stent (or scaffold) must be capable of sustaining radial compressive forces as it supports walls of a vessel. Therefore, a stent must possess adequate radial strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to remodel, after which the stent is no longer needed.

Examples of bioresorbable polymer scaffolds include those described in U.S. Pat. No. 8,002,817 to Limon, U.S. Pat. No. 8,303,644 to Lord, and U.S. Pat. No. 8,388,673 to Yang. FIG. 1 shows a distal region of a bioresorbable polymer scaffold designed for delivery through anatomical lumen using a catheter and plastically expanded using a balloon. The scaffold has a cylindrical shape having a central axis 2 and includes a pattern of interconnecting structural elements, which will be called bar arms or struts 4. Axis 2 extends through the center of the cylindrical shape formed by the struts 4. The stresses involved during compression and deployment are generally distributed throughout the struts 4 but are focused at the bending elements, crowns or strut junctions. Struts 4 include a series of ring struts 6 that are connected to each other at crowns 8. Ring struts 6 and crowns 8 form sinusoidal rings 5. Rings 5 are arranged longitudinally and centered on an axis 2. Struts 4 also include link struts 9 that connect rings 5 to each other. Rings 5 and link struts 9 collectively form a tubular scaffold 10 having axis 2 represent a bore or longitudinal axis of the scaffold 10. Ring 5d is located at a distal end of the scaffold. Crown 8 form smaller angles when the scaffold 10 is crimped to a balloon and larger angles when plastically expanded by the balloon. After deployment, the scaffold is subjected to static and cyclic compressive loads from surrounding tissue. Rings 5 are configured to maintain the scaffold's radially expanded state after deployment.

Scaffolds may be made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away from an implant site. Scaffolds may also be constructed of bioerodible metals and alloys. The scaffold, as opposed to a durable metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it has been shown that biodegradable scaffolds allow for improved healing of the anatomical lumen as compared to metal stents, which may lead to a reduced incidence of late stage thrombosis. In these cases, there is a desire to treat a vessel using a polymer scaffold, in particular a bioabsorbable or bioresorbable polymer scaffold, as opposed to a metal stent, so that the prosthesis's presence in the vessel is temporary.

Polymeric materials considered for use as a polymeric scaffold, e.g. poly(L-lactide) ("PLLA"), poly(D,L-lactide-co-glycolide) ("PLGA"), poly(D-lactide-co-glycolide) or poly(L-lactide-co-D-lactide) ("PLLA-co-PDLA") with less than 10% D-lactide, poly(L-lactide-co-caprolactone), poly (caprolactone), PLLD/PDLA stereo complex, and blends of the aforementioned polymers may be described, through comparison with a metallic material used to form a stent, in some of the following ways. Polymeric materials typically possess a lower strength to volume ratio compared to metals, which means more material is needed to provide an equivalent mechanical property. Therefore, struts must be made thicker and wider to have the required strength for a stent to support lumen walls at a desired radius. The scaffold made from such polymers also tends to be brittle or have limited fracture toughness. The anisotropic and rate-dependent inelastic properties (i.e., strength/stiffness of the material varies depending upon the rate at which the material is deformed, in addition to the temperature, degree of hydration, thermal history) inherent in the material, only compound this complexity in working with a polymer, particularly, bioresorbable polymers such as PLLA or PLGA.

An additional challenge with using a bioresorbable polymer (and polymers generally composed of carbon, hydrogen, oxygen, and nitrogen) for a scaffold structure is that the material is radiolucent with no radiopacity. Bioresorbable polymers tend to have x-ray absorption similar to body tissue. A known way to address the problem is to attach radiopaque markers to structural elements of the scaffold, such as a strut, bar arm or link. For example, FIG. 1 shows a link element 9d connecting a distal end ring 5d to an adjacent ring 5. The link element 9d has a pair of holes. Each of the holes holds a radiopaque marker 11. There are challenges to the use of the markers 11 with the scaffold 10. There needs to be a reliable way of attaching the markers 11 to the link element 9d so that the markers 11 will not separate from the scaffold during a processing step like crimping the scaffold to a balloon or when the scaffold is balloon-expanded from the crimped state. These two events—crimping and balloon expansion—are particularly problematic for marker adherence to the scaffold because both events induce significant plastic deformation in the scaffold body. If this deformation causes significant out of plane or irregular deformation of struts supporting, or near to markers the marker can dislodge (e.g., if the strut holding the marker is twisted or bent during crimping the marker can fall out of its hole). A scaffold with radiopaque markers and methods for attaching the marker to a scaffold body is discussed in US20070156230.

There is a need to improve upon the reliability of radiopaque marker securement to a scaffold for a thin-walled scaffold. Related to this need, there is a need to improve upon the performance characteristics of a scaffold, especially thin-walled scaffolds made from a bioresorbable material that must be navigated around tortuous anatomy.

SUMMARY OF THE INVENTION

What is disclosed are bioresorbable scaffolds having radiopaque markers and scaffold structure holding such radiopaque material and enabling a reduced a crimped profile ability and/or improved conformability to the catheter when the catheter, upon which the scaffold is mounted, is pushed through tortuous anatomy.

Scaffolds disclosed herein are suited to meet one of, or a combination of, the following objectives:
(i.) reduced crimped profile for a thin-walled scaffold carrying a radiopaque marker,
(ii.) securing the marker to the thin-walled scaffold,
(iii.) reducing strain energy buildup in marker-holding structure when the thin-walled scaffold is being deformed during crimping, balloon expansion at a target vessel site, or delivery of the scaffold to a target site, and
(iv.) reduced end ring flaring at a distal end of a scaffold for a thin-walled scaffold or scaffold comprising PLLA and having a wall thickness greater than 125 microns.

Being thin-walled, there has been realized through testing a need to modify certain critical areas of the scaffold that had not previously posed problems when a higher wall thickness was used. An example of a scaffold having a higher wall thickness of 158 microns is described in US 2010/0004735. It has been found that when a significant reduction in wall thickness is made, verses pre-existing bioresorbable scaffolds (e.g., from 160 microns wall thickness to 100 microns wall thickness) the arrangement, shape and dimensions of rings and link elements are, particularly at the distal end of the scaffold, in need of improvement.

A thin-walled scaffold is sought out because there is a clinical need to maintain low profiles for struts exposed in the bloodstream. Blood compatibility, also known as hemocompatibility or thromboresistance, is a desired property for scaffolds and stents. The adverse event of scaffold thrombosis, while a very low frequency event, carries with it a high incidence of morbidity and mortality. To mitigate the risk of thrombosis, dual anti-platelet therapy is administered with all coronary scaffold and stent implantation. This is to reduce thrombus formation due to the procedure, vessel injury, and the implant itself. Scaffolds and stents are foreign bodies and they all have some degree of thrombogenicity. The thrombogenicity of a scaffold refers to its propensity to form thrombus and this is due to several factors, including strut thickness, strut width, strut shape, total scaffold surface area, scaffold pattern, scaffold length, scaffold diameter, surface roughness and surface chemistry. Some of these factors are interrelated. Low strut profile also leads to less neointimal proliferation as the neointima will proliferate to the degree necessary to cover the strut. As such coverage is a necessary step to complete healing. Thinner struts are believed to endothelialize and heal more rapidly.

According to the various aspects of the invention, there is a thin-walled scaffold ("scaffold"), medical device, method for making such a scaffold, method of making a marker, attaching a marker to a strut, link or bar arm of a scaffold, method for crimping, or method for assembly of a medical device comprising such a scaffold having one or more, or any combination of the following things (1) through (15):
  (1) the scaffold crimped to a theoretical minimum crimp diameter (D-min);
  (2) the scaffold wall thickness is less than 125 microns, less than 100 microns, about 100 microns or about 93 microns;
  (3) a wavelength of a ring connected to a marker link is greater than a wavelength of another ring not connected to the marker link, and/or the wavelength of the ring connected to the marker length has a different length wavelengths;
  (4) a distance form a W crown to an adjacent U crown is higher than a distance from a Y crown to an adjacent U crown;
  (5) the scaffold is made from a tube comprising poly(L-lactide);
  (6) the scaffold crimped to a balloon, wherein the scaffold comprises a crimped state as shown and described in connection with FIG. 4D, 6A or 7A;
  (7) a method of crimping any of the scaffolds described in connection with FIG. 3, 4, 5, 6, or 7;
  (8) a method for attaching a radiopaque marker to the scaffold;
  (9) a marker link having the dimensions shown and described in connection with FIG. 2C.
  (10) a ring has n crests where n is more than 5, or more than 6 and less than or equal to 12.

(11) the ring has 2 wavelengths of a first size and n−3 wavelengths of a second size, the first size being greater than the second size;

(12) a ring connected to a marker link at a w crown has a first width and the adjoined ring connected to the marker link has a second width, greater than the first width;

(13) a ring connected to a marker link at a W crown has a wider flat portion or than a Y crown flat portion connected to the marker link and adjoined to the first ring.

(14) a first distance between rings adjoined by a marker link is greater than a second distance between rings not joined by marker links; and

(15) a first distance between rings adjoined by a non-linear link marker link is greater than a second distance between rings not joined by the non-linear marker link.

(16) D-min is about 1 mm or less than 1 mm

(17) An aspect ratio (AR) of the marker link for a thin-walled scaffold is between about 4 and 5, or about 4.5, where AR is defined as the maximum width of the marker link divided by the wall thickness at the marker link.

(18) A first wavelength or ½ wavelength of a first ring is greater than a second wavelength or ½ wavelength of an adjoined second ring.

(19) A first wavelength or ½ wavelength between two crests of a ring are different from a second wavelength between two other crests of the same ring.

(20) A ring is sinusoidal or zig-zag.

(21) A half wavelength measured from a W crown formed between a marker link and a first ring is about 15% higher than a half wavelength measured from a Y crown formed between the marker link and a second ring adjoined to the first ring; for a marker link that has a maximum width about 200% higher than the maximum width for a non-marker link.

(22) A wavelength measured from a W crown formed between a marker link and a first ring is between about 5% and 10% higher than the wavelength measured from a Y crown formed between the marker link and a second ring adjoined to the first ring; for a marker link that has a maximum width about 200% higher than the maximum width for a non-marker link.

(23) A wavelength measured from a W crown/crest formed between a marker link and a ring is between about 5% and 10% higher than the wavelength measured between other crests of the ring; for a marker link that has a maximum width about 200% higher than the maximum width for a non-marker link.

(24) A crown with B1 that is greater than a crown width B2; for example, a crown width B1 that is about 350% to about 400% greater than a crown width B2;

(25) A ring spacing A12 between a first ring and a second ring is greater than a ring spacing A23 between a second ring and a third ring; for example A12 is about 40% greater than A23.

(26) A link is a straight link or a non-linear link; for example link 20 and link 636.

(27) The length c1 that is about 36% higher than the length c2 for a marker link.

(28) The length c1 that is about 36% higher than the length c2 for a non-linear link.

(29) A medical device, comprising: a thin-walled scaffold having a network of rings interconnected by links, wherein each ring has a plurality of crests, wherein a crest is one of a U crown, Y crown and a W crown, each ring extends circumferentially in an undulating fashion along a vertical axis (B-B) perpendicular to a longitudinal axis (A-A); and a marker link extending between a first ring and a second ring of the rings, the marker link including a structure having a hole and a radiopaque material is contained within the hole; wherein the marker link forms with the first ring a first ring W crown and with the second ring a second ring Y crown, wherein a ½ wave length of the first ring measured from the first ring W crown to an adjacent U crown of the first ring is greater than a ½ wave length of the second ring measured from the second ring Y crown to an adjacent U crown of the second ring.

(30) The medical device of (29), in combination with one or more of, or any combination of items (a) through (g):
(a) wherein a length of the marker link is greater than a length of a link connecting the second ring to a third ring adjoined with the second ring;
(b) wherein the marker link includes a first link portion extending from the structure to the first ring W crown and a second link portion extending from the second ring Y crown to the structure, wherein a width of the first link portion is greater than a width of the second link portion;
(c) wherein a length of the first length portion is less than a length of the second link portion;
(d) wherein the structure includes a first and second holes, each containing the radiopaque material, wherein the first and second holes are aligned parallel to the axis A-A;
(e) wherein the first ring includes a first, second and third crest, the first crest corresponding to the first ring W crown, the second crest is adjacent the first crest and the third crest is adjacent the second crest, wherein a second wavelength extending from the second crest to the third crest is less than a first wavelength extending from the first crest to the second crest;
(f) wherein a flat portion of the first ring W crown is greater than a flat portion of a third ring W crown of a third ring adjoined with the second ring, and/or a flat portion of a fourth W crown of the first ring; and
(g) wherein a wavelength of the first ring forming the first ring W crown is longer than a wavelength of the second ring forming the second ring Y crown.

(31) A medical device, comprising: a thin-walled scaffold having proximal and distal end portions formed by a network of rings interconnected by links, wherein each ring has a plurality of crests, wherein a crest is one of a U crown, Y crown and W crown, and each ring extends circumferentially in an undulating fashion along a vertical axis (B-B) perpendicular to a longitudinal axis (A-A); a marker link extending between a first ring and a second ring of the rings, the marker link including a structure having a hole and a radiopaque material is contained within the hole; wherein the marker link forms with the first ring a first ring W crown and with the second ring a second ring Y crown, the first ring W crown corresponding to a first crest; and wherein a first wave length of the first ring measured from the first crest to a second crest of the first ring, adjacent the first crest, is greater than a second wave length of the first ring measured from the second crest to an adjacent third crest of the first ring.

(32) The medical device of (31), in combination with one or more of, or any combination of items (a) through (c):

(a) wherein the first ring has n crests and n−1 wavelengths where n is at least 6 and not more than 12, and wherein a first and second wavelength measured from the first crest and above and below, respectively, the first crest is greater than the remaining n−3 wavelengths measured between the n−1 crests;
(b) wherein all of the remaining n−3 wavelengths have the same length;
(c) wherein a length of the marker link is about equal to a length of a link connecting the second ring to a third ring.

(33) A medical device, comprising: a balloon catheter having a balloon, the balloon having a distal balloon end and a proximal balloon end; a thin-walled scaffold crimped to the balloon, the scaffold having proximal and distal end portions formed by a network of rings interconnected by links, wherein each ring has a plurality of crests, wherein a crest is one of a U crown, Y crown and W crown, and each ring extends circumferentially in an undulating fashion along a vertical axis (B-B) perpendicular to a longitudinal axis (A-A); a marker link extending between a first ring and a second ring of the rings, the marker link including a structure having a hole and a radiopaque material is contained within the hole; wherein the marker link forms with the first ring a first ring W crown and with the second ring a second ring Y crown, the first ring W crown corresponding to a first crest; wherein a first wave length of the first ring measured from the first crest to a second crest adjacent the first crest is greater than a second wave length of the first ring measured from the second crest to a third crest adjacent the second crest; wherein the thin-walled scaffold has an outer diameter of about D-min; and wherein D-min=$(1/\pi) \times [(n \times strut\_width) + (m \times link\_width)] + 2*t$.

(34) The medical device of (33), in combination with one or more of, or any combination of items (a) through (d):
(a) wherein a maximum width of the structure measured along axis B-B is greater than a maximum width of a link extending between the second ring and a third ring adjoined to the second ring;
(b) wherein the marker link includes a first link portion extending from the structure to the W crown and a second link structure extending from the Y crown to the structure, wherein a width of the first link portion is greater than a width of the second link portion;
(c) wherein a length of the first length portion is less than a length of the second link portion; and
(d) wherein the structure includes a first and second hole containing the radiopaque material, wherein the first and second holes are aligned parallel to the axis A-A.

(35) A method for making a medical device, comprising: using a tube comprising poly(L-lactide); forming a thin-walled scaffold pattern from the tube, the scaffold having proximal and distal end portions formed by a network of rings interconnected by links, wherein each ring has a plurality of crests, wherein a crest is one of a U crown, Y crown and W crown, and each ring extends circumferentially in an undulating fashion along a vertical axis (B-B) perpendicular to a longitudinal axis (A-A); the thin-walled scaffold including at least one marker link extending between a first ring and an adjoined second ring of the rings, the marker link including a structure having a hole; placing a radiopaque material in the marker hole, wherein the hole has a first size before the material placement and a second size, greater than the first size after material placement, and wherein the structure has a width measured along axis B-B; and crimping the thin-walled scaffold to a balloon catheter; wherein the thin-walled scaffold is crimped to about a theoretical-minimum crimped diameter (D-min); and wherein neither of the crowns adjacent and above and below the structure overlaps the structure.

(36) The medical device of (35), in combination with one or more of, or any combination of items (a) through (c):
(a) wherein the marker link forms with a first ring a first ring W crown and with the second ring a second ring Y crown, the first ring W crown corresponding to a first crest, and wherein a first wave length of the first ring measured from the first crest to a second crest adjacent the first crest is greater than a second wave length of the first ring measured from the second crest to an adjacent third crest;
(b) wherein the marker link forms with a first ring the first ring W crown and with the second ring a second ring Y crown, a first and second U crown is adjacent and above and below, respectively, the first ring W crown, a first strut extends from the first ring W crown to the first U crown and a second strut extends from the first ring W crown to the second U crown, wherein a distance between the first U crown and the second U crown, or a distance between the second strut to the first strut is greater than or equal to a maximum width of the marker structure measured along axis B-B; and
(c) wherein the width of the marker structure is greater than a maximum width of a link connecting the second ring to an adjacent third ring.

(37) A medical device, comprising: a thin-walled scaffold having proximal and distal end portions formed by a network of rings interconnected by links of the thin-walled scaffold, wherein each ring has a plurality of crowns, including U crowns and at least one of Y crowns and W crowns, each ring extends circumferentially in an undulating fashion along a vertical axis (B-B) perpendicular to a longitudinal axis (A-A); the proximal end portion includes an outermost proximal ring adjoined to a first proximal ring by first proximal links, and the first proximal ring is adjoined to a second proximal ring by second proximal links; the distal end portion includes an outermost distal ring adjoined to a first distal ring by first distal links, and the first distal ring is adjoined to a second distal ring by second distal links; wherein—the first proximal links include a proximal marker link comprising a proximal hole containing a radiopaque material, and—the first distal links are devoid of a link holding the radiopaque material.

(38) The medical device of (37), in combination with one or more of, or any combination of items (a) through (i):
(a) wherein the outermost proximal ring is adjoined to the first proximal ring only by the first proximal links, wherein two of which extend parallel to axis A-A and have a constant cross-sectional moment of inertia;
(b) wherein the outermost distal ring is adjoined to the first distal ring only by the first distal links, each of which are non-linear link struts;
(c) wherein the proximal marker link has a first end and a second end, the first end forming one of a W crown and a Y crown with the outermost proximal ring and the other of the W crown and Y crown with the first proximal ring;

(d) wherein the first distal ring and second distal ring are adjoined by a distal marker link;

(e) wherein the distal marker link includes a structure that circumscribes two holes and the first and second distal rings are adjoined additionally by one or two marker links;

(f) wherein the distal marker link has a first end and a second end, the first end forming one of a W crown and Y crown with the first distal ring and the other of the W crown and Y crown with the second distal ring, wherein the W crown is wider than the Y crown;

(g) wherein the proximal marker link further comprises: a rim substantially circumscribing the hole and defining a hole wall and a strut rim, wherein a distance between the wall and rim is D; a radiopaque marker disposed in the hole, the marker including a head having a flange disposed on the rim; wherein the flange has a radial length of between ½ D and less than D; wherein the thin-walled scaffold thickness (t) is related to a length (L) of the marker measured between an abluminal and luminal surface of the marker by $1.1 \leq (L/t) \leq 1.8$;

(h) wherein the distal marker link forms with the first distal ring one of the W crown and a Y crown with the second distal ring, wherein a ½ wave length of the ring having the W crown, measured from the W crown to a first adjacent crown is greater than a ½ wave length of the ring having the Y crown; and (i) wherein a length of the first proximal links is less than a length of the first distal links, and/or a length of the second distal links is less than the first distal links length.

(39) A medical device, comprising: a balloon catheter having a balloon, the balloon having a distal balloon end and proximal balloon end; a thin-walled scaffold crimped to the balloon, the thin-walled scaffold having proximal and distal end portions formed by a network of rings interconnected by links of the thin-walled scaffold, wherein each ring has a plurality of crowns, including U crowns and at least one of Y crowns and W crowns, each ring extends circumferentially in an undulating fashion along a vertical axis (B-B) perpendicular to a longitudinal axis (A-A); the proximal end portion, crimped to the proximal balloon end, includes an outermost proximal ring adjoined to a first proximal ring by first proximal links, and the first proximal ring is adjoined to a second proximal ring by second proximal links; the distal end portion, crimped the distal balloon end, includes an outermost distal ring adjoined to a first distal ring by first distal links, and the first distal ring is adjoined to a second distal ring by second distal links; wherein—the first proximal links include a proximal marker link comprising a proximal hole containing a radiopaque material,—the first distal links are devoid of a link holding the radiopaque material, and—the first distal links comprise non-linear links; wherein the thin-walled scaffold has an outer diameter of about D-min; and Wherein D-min=$(1/\pi) \times [(n \times \text{strut\_width}) + (m \times \text{link\_width})] + 2*t$.

(40) The medical device of (39), in combination with one or more of, or any combination of items (a) through (i):

(a) wherein the outermost proximal ring is adjoined to the first proximal ring only by the first proximal links, each of which extend parallel to axis A-A and have a constant cross-sectional moment of inertia;

(b) wherein the non-linear links are U-shaped links;

(c) wherein the proximal marker link has a first and second end, the first end forming one of a W crown and Y crown with the outermost proximal ring and the other of the W crown and Y crown with the first proximal ring, and wherein the marker link includes structure circumscribing holes;

(d) wherein a first link portion of the proximal marker link extends from the W-crown to the structure and a second link portion of the proximal marker link extends from the Y-crown to the structure, wherein a first link portion length is greater than a second link portion length;

(e) wherein the first link portion length is about equal to the sum of twice a ring width and a length of a strut extending between a U crown and a U, Y or W crown of the ring.

(f) wherein the non-linear link has a first and second end, the first end forming one of a W crown and Y crown with the outermost proximal ring and the other of a the W crown and Y crown with the first proximal ring, and wherein the non-linear link includes a U-shaped structure between the W crown and Y crown;

(g) wherein a first link portion of the proximal U-shaped link extends from the W-crown to the U-shaped structure and a second link portion of the proximal marker link extends from the Y-crown to the structure, wherein a first link portion length is greater than a second link portion length;

(h) wherein the first link portion length is about equal to the sum of twice a ring width and a length of a strut extending between a U crown and a U, Y or W crown crowns of a ring; and (i) wherein the distal marker link has a first and second end, the first end forming one of a W crown and Y crown with the first distal ring and the other of the W crown and Y crown with the second distal ring.

(41) A medical device, comprising: a thin-walled scaffold having proximal and distal end portions formed by a network of rings interconnected by links of the thin-walled scaffold, wherein each ring has a plurality of crowns, including U crowns and at least one of Y crowns and W crowns, each ring extends circumferentially in an undulating fashion along a vertical axis (B-B) perpendicular to a longitudinal axis (A-A); the proximal end portion includes an outermost proximal ring adjoined to a first proximal ring by first proximal links, and the first proximal ring is adjoined to a second proximal ring by second proximal links; the distal end portion includes an outermost distal ring adjoined to a first distal ring by first distal links, and the first distal ring is adjoined to a second distal ring by second distal links; wherein the first proximal links include a proximal marker link comprising a pair of proximal holes containing a radiopaque material, wherein the proximal holes are aligned along axis A-A, and the first distal links include a distal marker link comprising a pair of distal holes containing a radiopaque material, wherein the distal holes are aligned along axis B-B.

(42) The medical device of (41), in combination with one or more of, or any combination of items (a) through (i):

(a) wherein the outermost proximal ring is adjoined to the first proximal ring only by the first proximal links, wherein two of which extend parallel to axis A-A and have a constant cross-sectional moment of inertia;

(b) wherein the outermost distal ring is adjoined to the first distal ring only by the first distal marker link and non-linear link struts;

(c) wherein the proximal marker link has a first and second end, the first end forming one of a W crown and Y crown with the outermost proximal ring and the other of the W crown and Y crown with the first proximal ring;

(d) wherein a W crown width formed by the first end is greater than a Y crown width formed by the second end, such that a wavelength of the ring forming the W crown is longer than a wavelength of the ring forming the Y crown;

(e) wherein the distal marker link has a first and second end, the first end forming one of a W crown and Y crown with the outermost distal ring and the other of the W crown and Y crown with the first distal ring;

(f) wherein the distal marker link has a first link portion extending from the holes to the W crown and a second link portion extending from the holes to the Y crown, wherein a length of the first link portion is longer than a length of the second link portion;

(g) wherein the proximal marker link further comprises: a rim substantially circumscribing the hole and defining a hole wall and a strut rim, wherein a distance between the wall and rim is D; a radiopaque marker disposed in the hole, the marker including a head having a flange disposed on the rim; wherein the flange has a radial length of between ½ D and less than D; wherein the thin-walled scaffold thickness (t) is related to a length (L) of the marker measured between an abluminal and luminal surface of the marker by $1.1 \leq (L/t) \leq 1.8$;

(h) wherein the radiopaque material is contained within a hole and the radiopaque material has a shape of a frustum; and (i) wherein the hole comprises a first and second opening located on, respectively, a first and second side of the marker link, wherein the first opening is larger than the second opening and the frustum is substantially flush with the first and second openings.

(43) A medical device, comprising: a balloon catheter having a balloon, the balloon having a distal balloon end and a proximal balloon end; a thin-walled scaffold crimped to the balloon, the thin-walled scaffold having proximal and distal end portions formed by a network of rings interconnected by links of the thin-walled scaffold, wherein each ring has a plurality of crowns, including U crowns and at least one of Y crowns and W crowns, each ring extends circumferentially in an undulating fashion along a vertical axis (B-B) perpendicular to a longitudinal axis (A-A); the proximal end portion, crimped to the proximal balloon end, includes an outermost proximal ring adjoined to a first proximal ring by first proximal links, and the first proximal ring is adjoined to a second proximal ring by second proximal links; the distal end portion, crimped the distal balloon end, includes an outermost distal ring adjoined to a first distal ring by first distal links, and the first distal ring is adjoined to a second distal ring by second distal links; wherein (1) the first proximal links include a proximal marker link comprising a structure extending parallel to axis A-A and containing a radiopaque material, (2) the first distal links include a distal marker link comprising a structure, and extending parallel to axis B-B and containing the radiopaque material; wherein the thin-walled scaffold has an outer diameter of about D-min; and wherein D-min=$(1/\pi) \times [(n \times strut\_width) + (m \times link\_width)] + 2*t$.

(44) The medical device of (43), in combination with one or more of, or any combination of items (a) through (i):

(a) wherein the outermost proximal ring is adjoined to the first proximal ring only by the first proximal links, each of which extend parallel to axis A-A and have a constant cross-sectional moment of inertia;

(b) wherein the first distal links include non-linear links;

(c) wherein the proximal marker link has a first and second end, the first end forming one of a W crown and Y crown with the outermost proximal ring and the other of the W crown and Y crown with the first proximal ring, and wherein the marker link includes structure circumscribing holes;

(d) wherein a first link portion of the proximal marker link extends from the W crown to the structure and a second link portion of the proximal marker link extends from the Y crown to the structure, wherein a length of the first link portion is greater than a length of the second link portion.

(e) wherein the first link portion length is about equal to the sum of twice a ring width and a length of a strut extending between a U crown and a Y, U or W crown of a ring;

(f) wherein the first distal links comprise a non-linear link having a first and second end, the first end forming one of a W crown and a Y crown with the outermost proximal ring and the other of the W crown and Y crown with the first proximal ring, and wherein the non-linear link includes a U-shaped structure between the W crown and Y crown;

(g) wherein a first link portion of the non-linear link extends from the W crown to the U-shaped structure, and a second link portion of the non-linear link extends from the Y crown to the U-shaped structure, wherein a length of the first link portion length is greater than a length of the second link portion;

(h) wherein the first link portion length is about equal to the sum of twice a ring width and a length of a strut extending between a U crown and a Y, U or W crown of a ring; and (i) wherein the holes of the distal marker link are between and not overlapping or under-lapping a U-crown adjacent a W-crown of the outermost distal ring and a U crown adjacent a Y crown of the first distal ring.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIG. 3A shows section IIIA of the scaffold of FIG. 3.

FIG. 3B shows section IIIB of the scaffold of FIG. 3.

FIG. 4A shows section IVA of the scaffold of FIG. 4.

FIG. 4B shows the distal end ring of the scaffold in FIG. 3 with a distal end ring of the scaffold of FIG. 4 in phantom, to show differences between the two rings.

DETAILED DESCRIPTION

Figure 1:
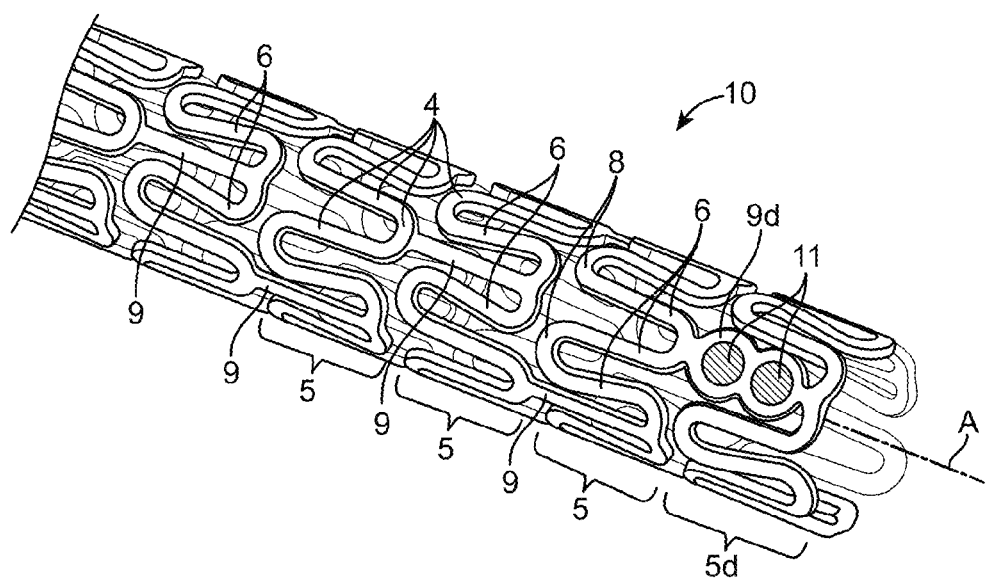
FIG. 1 is a perspective view of a portion of a prior art scaffold. The scaffold is shown in a crimped state (balloon not shown).

In the description like reference numbers appearing in the drawings and description designate corresponding or like elements among the different views.

For purposes of this disclosure, the following terms and definitions apply:

The terms "about," "approximately," "generally," or "substantially" mean 30%, 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, d1 about d2 means d1 is 30%, 20%, 15%, 10%, 5%, 4%, 3%, 2%, 1.5%, 1%, 0% or between 1-2%, 1-3%, 1-5%, or 0.5%-5% different from d2. If d1 is a mean value, then d2 is about d1 means d2 is within a one-sigma, two-sigma, or three-sigma variance or standard deviation from d1.

It is understood that any numerical value, range, or either range endpoint (including, e.g., "approximately none", "about none", "about all", etc.) preceded by the word "about," "approximately," "generally," or "substantially" in this disclosure also describes or discloses the same numerical value, range, or either range endpoint not preceded by the word "about," "approximately," "generally," or "substantially."

The "glass transition temperature," TG, is the temperature at which the amorphous domains of a polymer change from a brittle vitreous state to a solid deformable or ductile state at atmospheric pressure. This application defines TG and methods to find TG, or TG-low (the lower end of a TG range) for a polymer in the same way as in U.S. application Ser. No. 14/857,635.

A "stent" means a permanent, durable or non-degrading structure, usually comprised of a non-degrading metal or metal alloy structure, generally speaking, while a "scaffold" means a temporary structure comprising a bioresorbable or biodegradable polymer, metal, alloy or combination thereof and capable of radially supporting a vessel for a limited period of time, e.g., 3, 6 or 12 months following implantation. It is understood, however, that the art sometimes uses the term "stent" when referring to either type of structure.

"Inflated diameter" or "expanded diameter" refers to the inner diameter or the outer diameter the scaffold attains when its supporting balloon is inflated to expand the scaffold from its crimped configuration to implant the scaffold within a vessel. The inflated diameter may refer to a post-dilation balloon diameter which is beyond the nominal balloon diameter, e.g., a 6.5 mm balloon (i.e., a balloon having a 6.5 mm nominal diameter when inflated to a nominal balloon pressure such as 6 times atmospheric pressure) has about a 7.4 mm post-dilation diameter, or a 6.0 mm balloon has about a 6.5 mm post-dilation diameter. The nominal to post dilation ratios for a balloon may range from 1.05 to 1.15 (i.e., a post-dilation diameter may be 5% to 15% greater than a nominal inflated balloon diameter). The scaffold diameter, after attaining an inflated diameter by balloon pressure, will to some degree decrease in diameter due to recoil effects related primarily to, any or all of, the manner in which the scaffold was fabricated and processed, the scaffold material and the scaffold design.

When reference is made to a diameter it shall mean the inner diameter or the outer diameter, unless stated or implied otherwise given the context of the description.

When reference is made to a scaffold strut, it also applies to a link or bar arm.

"Post-dilation diameter" (PDD) of a scaffold refers to the inner diameter of the scaffold after being increased to its expanded diameter and the balloon removed from the patient's vasculature. The PDD accounts for the effects of recoil. For example, an acute PDD refers to the scaffold diameter that accounts for an acute recoil in the scaffold.

A "before-crimp diameter" means an outer diameter (OD) of a tube from which the scaffold was made (e.g., the scaffold is cut from a dip coated, injection molded, extruded, radially expanded, die drawn, and/or annealed tube) or the scaffold before it is crimped to a balloon. Similarly, a "crimped diameter" means the OD of the scaffold when crimped to a balloon. The "before-crimp diameter" can be about 2 to 2.5, 2 to 2.3, 2.3, 2, 2.5, 3.0 times greater than the crimped diameter and about 0.9, 1.0, 1.1, 1.3 and about 1-1.5 times higher than an expanded diameter, the nominal balloon diameter, or post-dilation diameter. Crimping, for purposes of this disclosure, means a diameter reduction of a scaffold characterized by a significant plastic deformation, i.e., more than 10%, or more than 50% of the diameter reduction is attributed to plastic deformation, such as at a crown in the case of a stent or scaffold that has an undulating ring pattern, e.g., FIG. 1. When the scaffold is deployed or expanded by the balloon, the inflated balloon plastically deforms the scaffold from its crimped diameter. Methods for crimping scaffolds made according to the disclosure are described in US20130255853.

A material "comprising" or "comprises" poly(L-lactide) or PLLA includes, but is not limited to, a PLLA polymer, a blend or mixture including PLLA and another polymer, and a copolymer of PLLA and another polymer. Thus, a strut comprising PLLA means the strut may be made from a material including any of a PLLA polymer, a blend or mixture including PLLA and another polymer, and a copolymer of PLLA and another polymer.

Figure 2:
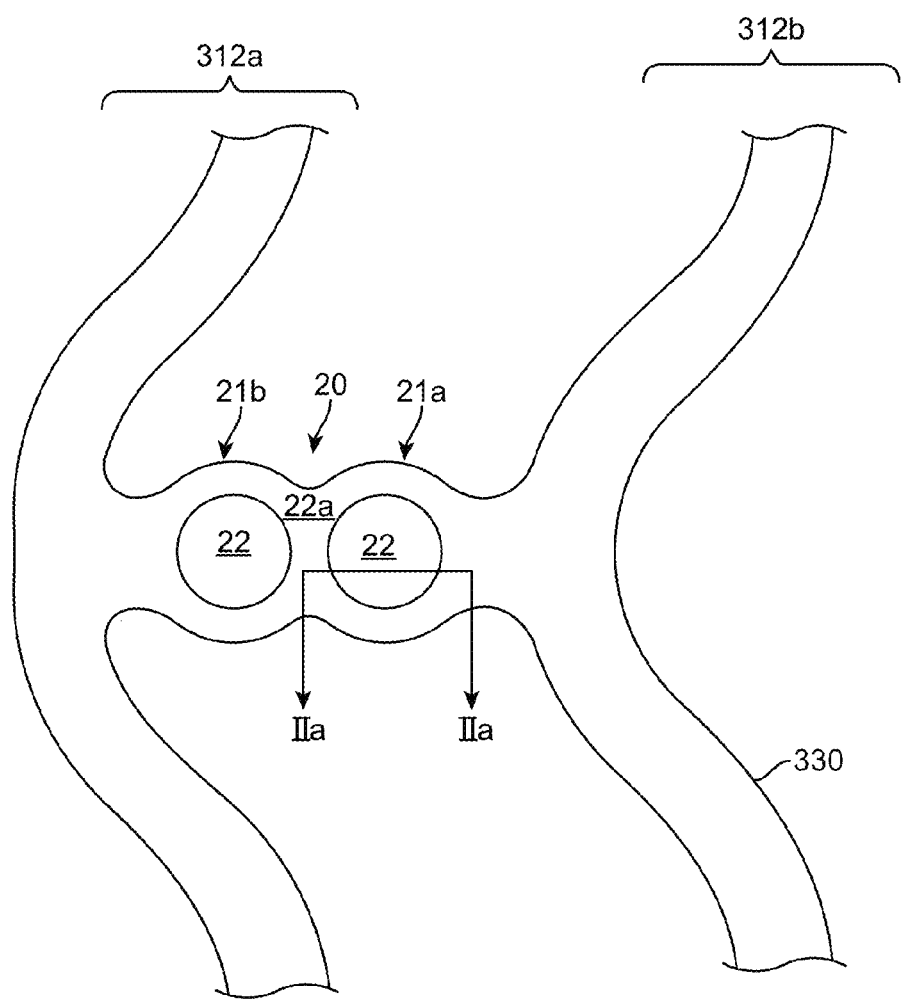
FIG. 2 is a top partial view of a scaffold showing a marker link that has holes for retaining a radiopaque material and connects adjoining rings.

Bioresorbable scaffolds comprised of biodegradable polyester polymers are radiolucent. In order to provide for fluoroscopic visualization, radiopaque markers are placed on the scaffold. For example, the scaffold described in U.S. Pat. No. 8,388,673 ('673 patent) has two platinum markers 206 secured at each end of the scaffold 200, as shown in FIG. 2 of the '673 patent.

Figure 3:
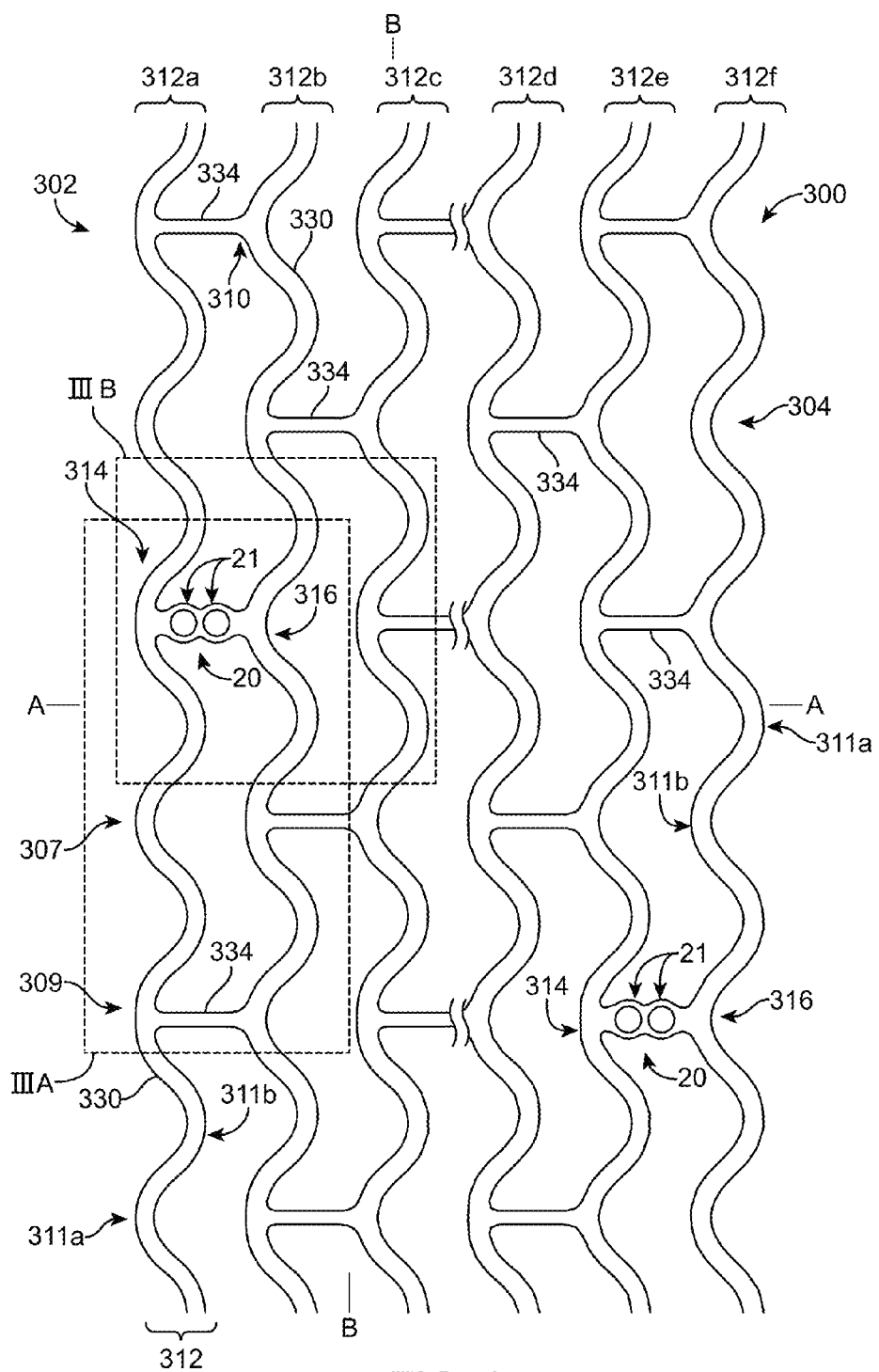
FIG. 3 shows distal and proximal end portions of a scaffold according to one embodiment. The end portions include the marker link of FIG. 2 connecting rings.

When reference is made to a direction perpendicular to, or parallel with/to axis A-A (e.g., as shown in FIG. 3) it will mean perpendicular to, or parallel with/to the axial direction of a scaffold or tube. Similarly, When reference is made to a direction perpendicular to, or parallel with/to axis B-B (e.g., as shown in FIG. 3) it will mean perpendicular to, or parallel with/to the circumferential direction of the scaffold or tube. Thus, a sinusoidal ring of a scaffold extends parallel with/to (in periodic fashion) the circumferential direction or parallel to axis B-B, and perpendicular to axis A-A whereas a link in one embodiment extends parallel to the axial direction or axis A-A of the scaffold or tube and perpendicular to the axis B-B.

Wherever the same element numbering is used for more than one drawing it is understood the same description first used for the element in a first drawing applies to embodiments described in later drawings, unless noted otherwise.

The dimension of thickness (e.g., wall, strut, ring or link thickness) refers to a dimension measured perpendicular to both of axes A-A and B-B. The dimension of width is measured in the plane of axes A-A and B-B; more specifically, the width is the cross-sectional width from one side to another side of a contiguous structure; thus, a U-shaped link 636 has a constant link width over its length just as link 334 has a constant link width. Moreover, it is understood that the so-called plane of axes A-A and B-B is technically not a plane since it describes surfaces of a tubular structure having central lumen axis parallel with axis A-A. Axis B-B therefore may alternatively be thought of as the angular component if the scaffold locations were being described using a cylindrical coordinate system (i.e., axis A-A is Z axis and location of a luminal/abluminal surface of a crown, link, ring, etc. is found by the angular coordinate and radial coordinate constant).

A "thin wall thickness," "thin-walled scaffold," "thin-wall" refers to a strut, ring, link, or bar arm made from a polymer comprising poly(L-lactide) and having a wall thickness less than 125 microns. The challenges faced when working with a thin-walled scaffold are discussed herein, including retaining a marker having the same volume of radiopaque material FIG. 2 is a top planar view of a portion of a polymer scaffold, e.g., a polymer scaffold having a pattern of rings interconnected by links. There is a marker link 20 ("link 20") extending between rings 312a, 312b in FIG. 2. The link 20 has formed left and right structures or strut portions 21b, 21a, respectively, for holding a radiopaque marker. The markers are retainable in holes 22 formed by the structures 21a, 21b. The surface 22a corresponds to an abluminal surface of the scaffold.

Figure 2A:
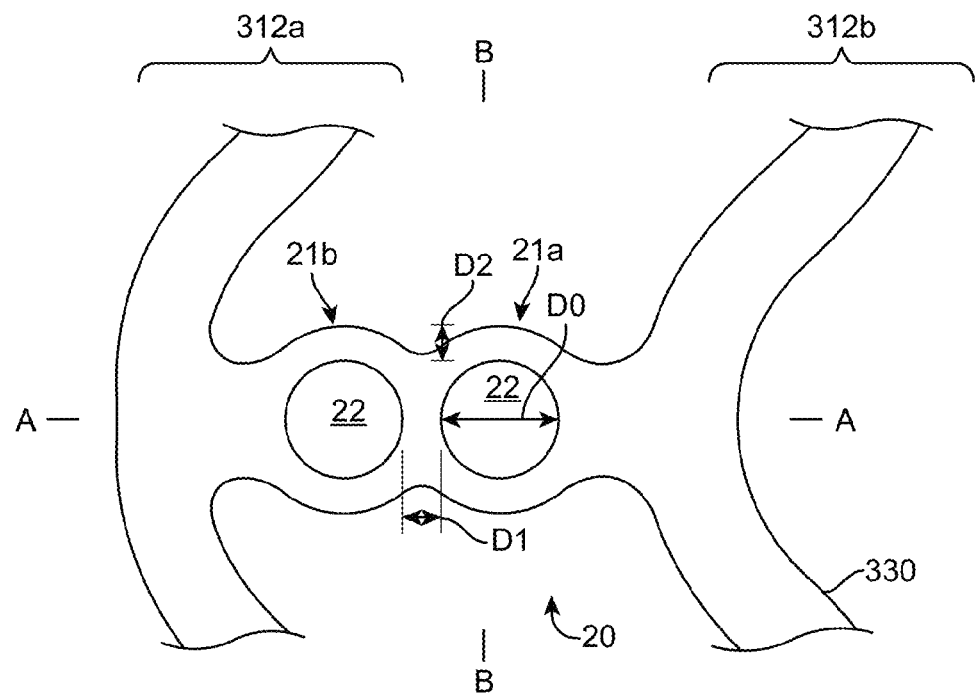
FIG. 2A is a reproduction of FIG. 2 showing additional dimensional characteristics and/or feature of link for holding two markers.

FIG. 2A is a reproduction of FIG. 2 illustrating additional dimensional features, specifically characteristic dimensional features D0, D1 and D2. The diameter of the hole 22 is D0. The distance between the adjacent holes 22 is greater than or equal to D1. And the brim width of either or both holes 22, or distance from the inner wall surface circumscribing either or both holes 22 to the edge of the link 20 is greater than or equal to D2.

Figure 2B:
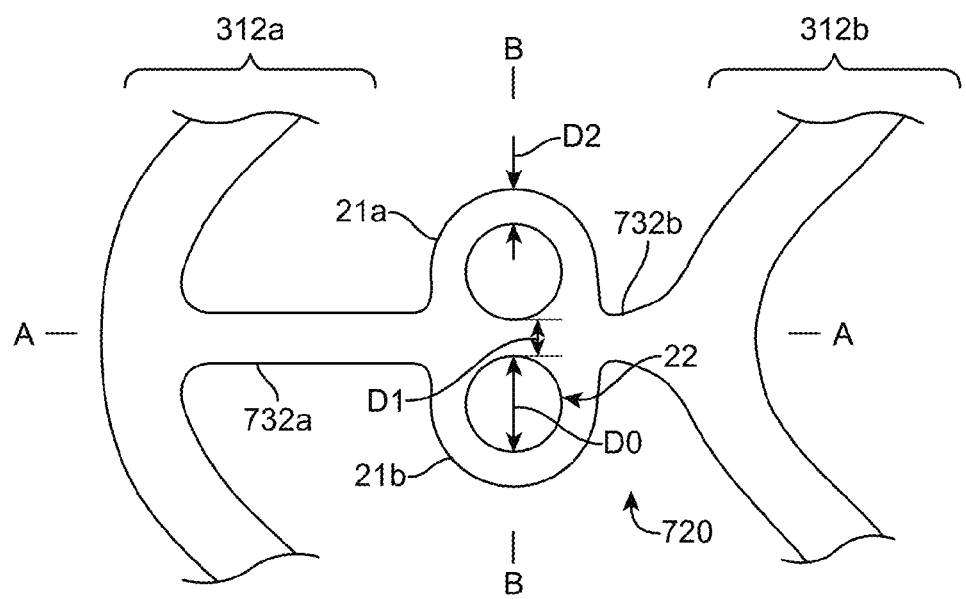
FIG. 2B shows an alternative embodiment of a marker link.
Figure 7:
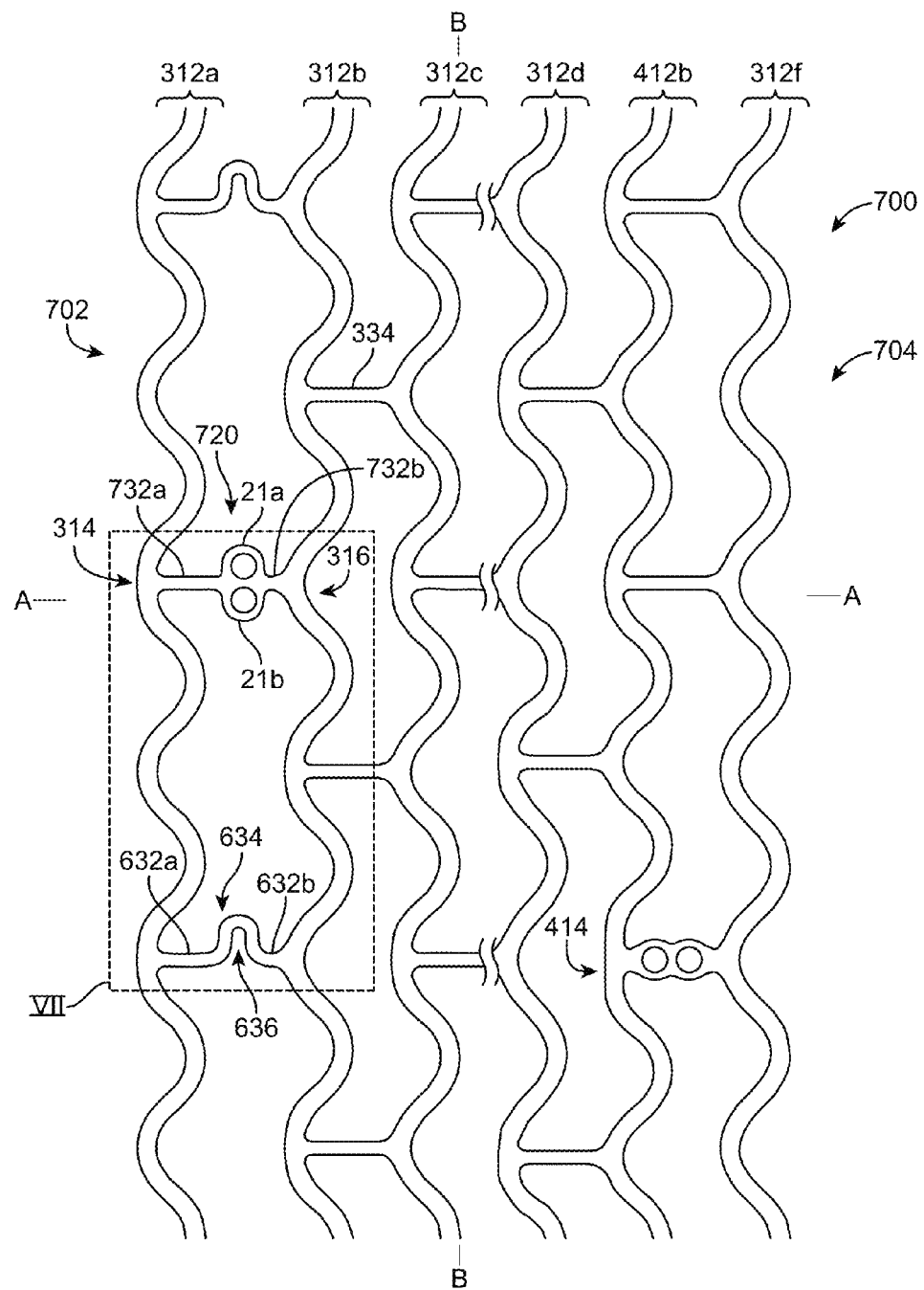
FIG. 7 shows end portions of a scaffold according to another embodiment. The proximal end portion is different from the distal end portion. Non-linear link struts and a modified marker link connects the outermost distal ring to an inner ring.

FIG. 2B shows the dimensional features described in connection with FIG. 2A for a marker link 720 oriented so that the structures 21a, 21b are offset along axis B-B, as opposed to axis A-A. The marker 720 connects rings 312a and 312b. A scaffold embodying this marker is shown in FIG. 7.

Figure 2C:
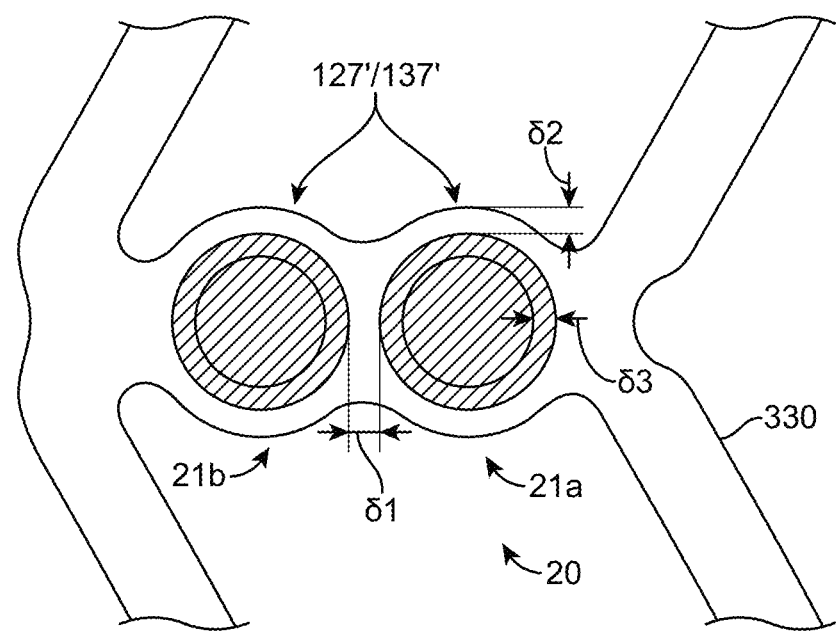
FIG. 2C is another reproduction of FIG. 2 with markers attached to the link.

FIG. 2C there is shown rivet-type markers 127'/137' secured in the holes 22. The dimensions indicated refer to parameters that may be used to inspect the marker link (after the radiopaque is connected) to evaluate its capacity for resisting forces that tend to dislodge the rivet 127'/137' from the hole 22. These dislodging forces can be produced by a pressurized balloon surface or a deformation of nearby scaffold structure tending to deform the hole 22, such as when the scaffold is crimped or balloon expanded. According to one aspect, the rivet heads and/or tails of the rivet 127'/137' pair may be inspected to determine whether the minimum distances δ1, δ2, and δ3 (FIG. 2C) are satisfied. The distances δ1, δ2, and δ3 reflect either or both a minimum size of a head and/or tail of the rivet that was pressed into the hole, which indicates both that the rivet should hold in the hole 22 (if the head or tail is too small in diameter it cannot resist as well the dislodging forces) and that excess rivet material will not cause problems such as balloon puncture or vessel irritation when the scaffold is implanted within a vessel. According to the embodiments the minimum distance from the end of the marker head/tail to the brim of the strut (or link) portion 21a/21b, δ2 that is, can be about 10%, 25% and up to 50% of D2. Above 50% means the head or tail can be too small to hold the rivet in place. For a head/tail equal to, or greater than D2 the head may or does extend beyond the brim of the strut/link, which can lead to problems such as forming a relatively sharp edge than can damage the balloon or irritate adjacent tissue. The minimum distance between the marker heads/tails, δ1 that is, is 0 or up to 25% of the distance D1. If the rims or heads of the markers overlap each other this can exceed the maximum height desired for the strut (about 160 microns). The minimum length for the head/tail extending to the right or left of the hole 22, δ3 that is, is anything greater than 50% of D2.

Methods for inserting radiopaque markers into holes commonly rely on a cylindrical hole to retain the marker. Most of the force of retention comes from friction between the walls and the marker material. Marker material has been reliably retained in scaffold holes in this manner when the scaffold has a wall thickness of 150 microns and above. However, it becomes far more challenging to hold the marker material within a hole when the wall thickness is reduced to 100 microns or less than 100 microns. Although a coating material for carrying a drug can help to hold the marker in place, the coatings, such as Everolimus/PDLLA, tends to be quite thin—on the order of 3 microns, which limits it's out of plane shear strength resisting dislodgment of the marker from the hole.

There are several desirable properties or capabilities that follow from a reduction in wall thickness for a scaffold strut. The advantages of using the reduced wall thickness include a lower profile and hence better deliverability, reduced acute thrombogenicity, and potentially better healing. In some embodiments it is desirable to use the same size marker for a scaffold having thinner struts, so that there is no difference, or reduction, in radiopacity between the two scaffold types. Reducing the strut thickness, while keeping the marker hole 22 the same size can however result in the marker protruding above and/or below the strut surfaces due to the reduced hole volume. It may be desirable to keep the abluminal and luminal surfaces 25a, 25b of a marker' flush with corresponding luminal and abluminal surfaces of the strut, in which case the hole 22 diameter (d) may be increased to partially account for the reduced hole volume resulting from the thinner strut.

Paragraphs [0073] through [0083] of U.S. application Ser. No. 14/738,710, which shares a common inventor with this application, describes the factors affecting a scaffold's ability to retain a marker in a hole and the special challenges faced when a wall thickness is less than 160 microns, or less than 125 microns. According to some embodiments it has been found that a marker cannot be retained in a hole reliably by essentially friction alone when the wall thickness is less than 125 microns, i.e., when the scaffold is thin-walled. In a preferred embodiment where the wall thickness is less than 100 microns a marker material is retained within a hole using a rivet-shaped marker, discussed briefly above in connection with FIG. 2C and described in greater detail in connection with FIGS. 8-16.

Following are described embodiments of scaffold patterns suited to meet one of, or a combination of the following objectives:
(i.) reduced crimped profile for a thin-walled scaffold carrying a radiopaque marker,
(ii.) securing a radiopaque marker in a thin-walled scaffold,
(iii.) reducing strain energy buildup in marker-holding structure when the thin-walled scaffold is being deformed during crimping, balloon expansion at a target vessel site, or delivery of the scaffold to a target site, and
(iv.) avoiding protruding or flaring end rings at a distal end of a scaffold for a thin-walled scaffold or scaffold comprising PLLA and having a wall thickness greater than 125 microns.

It will be appreciated that the above objectives are inter-related and more than one objective can be addressed by a single change. For example, by making a marker link more flexible both of objectives (iii) and (iv) can be met. Scaffolds according to these embodiments may be made from a thin-walled tube or sheet of material comprising poly(L-lactide) (PLLA), which is laser cut from a tubular body to produce the patterns shown in FIGS. 3-7. Processes to make the tube may include one or more of extrusion, injection molding, solid-phase processing, and biaxial expansion as described in U.S. Ser. No. 14/810,344 (62571.1212).

Figure 3C:
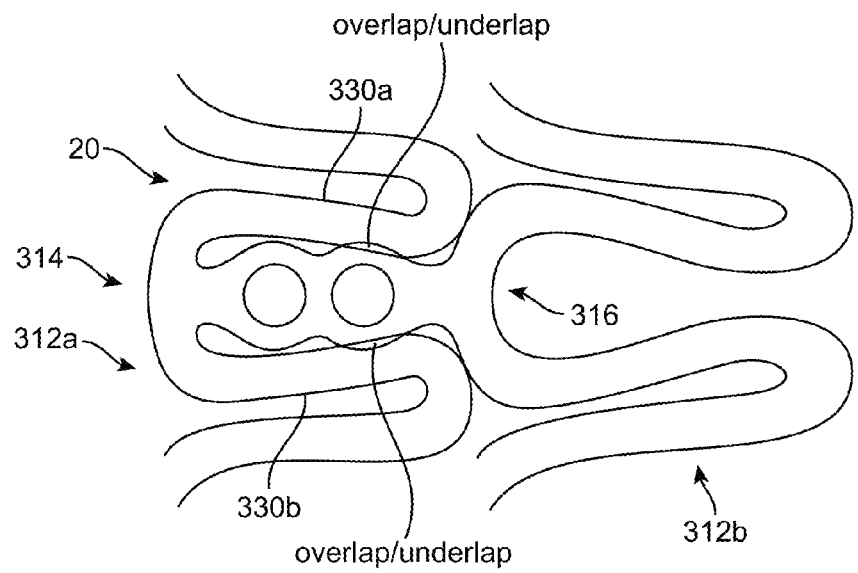
FIG. 3C shows the scaffold of FIG. 3 in a crimped state.
Figure 3D:
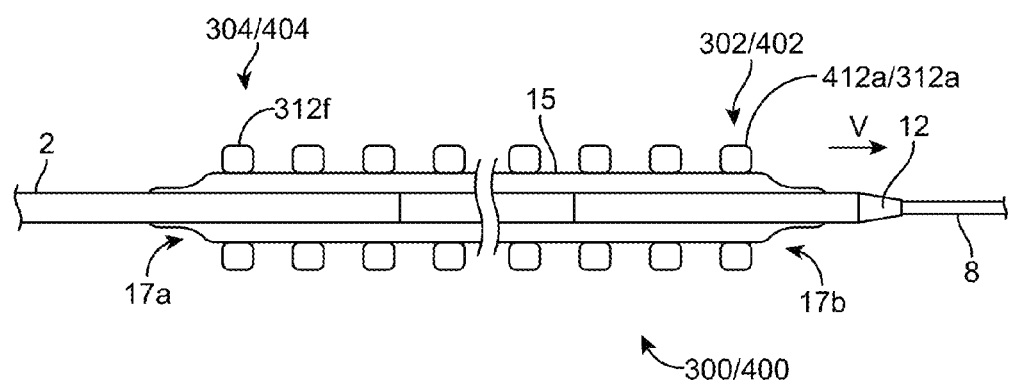
FIG. 3D shows the scaffold of FIG. 3 crimped to a balloon of a balloon catheter.

Scaffolds according to the embodiments, e.g., scaffolds 300, 400, 500, 600 or 700, are preferably crimped to a balloon catheter, such as the one shown in FIG. 3D. The scaffold may be attached to the balloon to secure the desired crimped diameter, such as D-min (defined, infra) using any of the crimping processes described in US20130255853; specifically any of the crimping processes and apparatus for crimping described at paragraphs [0068]-[0073], [0077]-[0099], [0111]-[0126], [0131]-[0146] and FIGS. 1A, 1B, 4A. 4B, 5A, 5B, 8A, and 8B of US20130255853.

FIG. 3 shows a partial, planer view of end portions of a scaffold according to one embodiment, or scaffold 300. The left or distal end portion 302 (i.e. the left side of FIG. 3) includes sinusoidal rings 312a, 312b, and 312c where ring 312a is the outermost ring. Ring 312a and ring 312b are adjoined by two links 334 and a marker link 20. Ring 312c and ring 312d are adjoined by three links 334 that extend parallel to axis A-A. The links 334 extend parallel to axis A-A and have a constant cross-sectional moment of inertia across its length, meaning link 334 has a constant width and thickness and the location of the centroid or geometric center (or longitudinal axis) of the link is everywhere parallel with axis A-A. The right or proximal end portion 304 (i.e. the right side of FIG. 3) includes sinusoidal rings 312d, 312e, and 312f where ring 312f is the outermost ring. Ring 312d and ring 312e are adjoined by three links 334. Ring 312e and ring 312f are adjoined by two links 334 and the marker link 20. Thus, scaffold 300 has a marker link 20 extending between and adjoining the outermost link with the adjacent, inner ring. The scaffold 300 may have 15, 18 or 20 rings 312 interconnected to each other by links 334.

A ring 312, e.g., ring 312*b*, is sinusoidal meaning the curvature of the ring along axis B-B is best described by a sine wave where the wavelength of the sine wave is equal to the distance between adjacent crests 311*a* of the ring. The ring has a constant width at both crowns 307, 309 and 310 and struts 330, which connect a crown to an adjacent crown.

There are three crown types present in each inner ring 312*b* through 312*e*: U-crown, Y-crown and W-crown. Outermost rings have only the Y-crown or W-crown type, and the U-crown type. A crest or peak 311*a* (or trough or valley 311*b*) may correspond to a U-crown, Y-crown or W-crown. For the outermost ring 312*a* there is only a U-crown and W-crown type. For the outermost ring 312*f* there is only a U-crown and Y-crown type. A marker link 20 adjoins rings by forming a W-crown with the first ring (e.g., ring 312*e*) and a Y-crown with the second ring (e.g. ring 312*f*).

A link 334 connects to ring 312*f* at a Y-crown 310. A "Y-crown" refers to a crown where the angle extending between a strut 330 of a ring 312 and the link 334 is an obtuse angle (greater than 90 degrees). A link 334 connects to ring 312*a* at a W-crown 309. A "W-crown" refers to a crown where the angle extending between the strut 330 and the link 334 is an acute angle (less than 90 degrees). A U-crown 307 is a crown that does not have a link connected to it. Marker link 20 connects to a ring at a W-crown 314 and a Y-crown 316.

For the scaffold 300 there are 6 crests or peaks 311*a* and 6 troughs or valleys 311*b* for each ring 312. A crest 311*a* is always followed by a valley 311*b*. Ring 312*b* has 12 crowns: 3 are W-crowns 309, 3 are Y-crowns 310 and 6 are U-crowns 307.

FIGS. 3A and 3B show partial, close-up views of the scaffold 300. FIG. 3A shows section IIIA of FIG. 3 and FIG. 3B shows section IIIB of FIG. 3. The following description, made in respect to FIGS. 3A-3B, applies the same for portions 302 and 304 of scaffold 300 with the understanding that in the case of the link 20 it connects to the outermost ring 312*f* at a Y-crown 316 and adjoining ring 312*e* at a W-crown 314.

Referring to FIG. 3A, consecutive wavelengths of the outermost ring 312*a* have lengths L1 and L2, or the distance (along axis B-B) from crown 314 to U-crown 307 is L1 and the distance from U-crown 307 to Y-crown 309 is L2. The same distances apply for rings 312*b*—crown 316 to W-crown 309 and W-crown 309 to Y-crown 310 are L1 and L2, respectively. For scaffold 300 L1=L2=constant for rings 312*a*, 312*b*. That is, the distance or wavelength from one crest to another is the same. Also, for scaffold 300 L1+L2 is constant everywhere; that is, for all rings the distance between a W-crown and Y-crown is the same, as is the distance between adjacent crests for the rings 312*a* through 312*f*. The distance X in FIG. 3A refers to a half-period or half-length of the sine wave, or ½ of L1. The distance X is equal to the distance from the crown 314 to the adjacent U-crown 307 for crown 312*a*. X is the same for ring 312*b*. In other embodiments L1 is not equal to L2 and X is different between the outermost ring 312*a* and adjoining ring 312*b*.

In alternative embodiments, including scaffolds 400, 500 or 700 described below, the rings may have zig-zag instead of sinusoidal ring shapes. An example of zig-zag shaped rings is found in FIGS. 5A and 6A of US20140039604. A zig-zag ring may be described as non-curved strut elements converging at a crown that is shaped to have an inner and outer crown radius. The same description applies, meaning the ring may be described in terms of wavelengths, struts and crowns, except that the shape is not sinusoidal but zig-zag. The term "undulating" refers to both zig-zag and sinusoidal ring types.

Referring to FIG. 3B, a distance along axis A-A from the peak or crest of the ring 312*a* to the peak or the crest of the adjoining ring 312*b*, or the length of marker 20 (plus the width t1) is A12. A distance along axis A-A from the peak or a crest of the ring 312*b* to the peak or the crest of the adjoining ring 312*c*, or length of marker 334 between these rings (plus the width t2) is A23. For scaffold 300 A12=A23. The width of the link 20 to the left of marker structure 21*a* is tm1 and the width of the marker link 20 to the right of structure 21*b* is tm2. The width of the link 334 is t11. The crowns 307, 310, 309 and 314 and struts 330 of ring 312*a* have a constant width t1. The crowns 307, 310, 309 and 314 and struts 330 of ring 312*b* have a constant width t2. The crowns 307, 310, 309 and 314 and struts 330 of ring 312*c* have a constant width t3. For scaffold 300 t1 is less than t2 and t2=t3. The dimension B1 and B2 refer to a surface of the crowns for rings 312*a* and 312*c*, respectively, extending parallel to axis B-B or the crown surface portion without curvature, i.e., flat. For scaffold 300 B1=B2.

Referring to FIG. 3C there is shown the scaffold 300 having marker 20 in a crimped state. The crimped diameter enforced on scaffold 300 is the theoretical minimum crimped diameter where struts that converge at the same crown are in contact with each other when the scaffold is fully crimped, i.e., when the scaffold is removed from the crimping device, or when placed within a restraining sheath soon after crimping. The equation for the theoretical minimum crimped diameter (D-min) under these conditions is shown below $$D\text{-min}=(1/\pi)\times[(n\times\text{strut\_width})+(m\times\text{link\_width})]+2*t$$

Where

"n" is the number of struts in a ring (12 struts for scaffold 300),

"strut_width" is the width of a strut (170 microns for scaffold 300),

"m" is the number of links adjoining adjacent rings (3 for scaffold 300),

"link_width" is the width of a link (127 microns for scaffold 300), and

"t" is the wall thickness (93 microns for scaffold 300).

Hence, for scaffold 300 D-min=$(1/\pi)\times[(12\times170)+(3\times127)]+2\times(93)$=957 microns.

For adjoined ring pairs 312*a* and 312*b* at the distal end 302, and adjoined ring pairs 312*e* and 312*f* at the distal end the marker link 20 is wider (along axis B-B) than is a link 334 in order to accommodate the markers. As a consequence the adjacent struts 330 can often overlap the link 20 to achieve the same D-min throughout. This condition is depicted in FIG. 3C. Such a state for the crimped scaffold introduces concerns regarding local strength for the rings and link holding the marker. As shown in FIG. 3C there is an overlap (strut presses against abluminal surface of marker) or underlap (strut presses against luminal surface of marker) by the struts 330*a*, 330*b* and/or the associated U crowns associated with these struts. It is preferred to eliminate this overlap/underlap when the scaffold is crimped.

Scaffold struts, in particular thin-walled scaffold struts and links, are not designed to twist or carry significant torsion. Twisting occurs when struts abut and overlap each other. When a scaffold strut has a higher aspect ratio of width to thickness, there is greater propensity for the strut to twist when it abuts adjacent structure, e.g., the structure 21*a* of the marker link 20 (a thin walled scaffold has a higher aspect ratio for the same vessel tissue coverage—strut width—as compared to a thicker-walled scaffold). As can be appreciated from the deformed state of FIG. 3C compared with FIG.

TABLE 1 comparison between scaffold 300 and thicker-walled scaffold

| Property | US 2010/0004735 | Scaffold 300 | Comments/observations |
|---|---|---|---|
| Tubing thickness (microns) | 158 | 93 | Thinner struts may have an increased tendency to overlap each other when encountering strut-to-strut sidewall contact during crimping. |
| 3.0 mm scaffold (before crimp size of 3.0 mm) minimum crimp (in) | 0.051 (in) | 0.041 (in) | More aggressive crimping increases the likelihood of strut-to-strut overlapping |
| Crimped diameter | 0.050 (in) | 0.038 (in) | during crimping, or when a restraining sheath is placed over the crimped scaffold. |
| Average marker bead sphere radius (in) | 0.0045 | | More severe flattening of an identical marker bead sphere |
| Marker bead sphere volume (in$^3$) | 3.82E−07 | 3.82E−07 | results in a 30% broader theoretical cylinder shape |
| Theoretical marker bead cylinder diameter when swaged and flush with strut luminal surface (in) | 0.0088 | 0.0115 | for the thin-walled scaffold, increasing propensity for overlapped struts at marker bead region. |

3 torsion is introduced in the ring structure and possibly also the marker link strut. This type of abnormal deformation can lead to crack propagation or reduced fatigue life of the ring and/or link 20 at the time of balloon expansion in a vessel.

FIG. 3D shows a medical device comprising a balloon catheter and the scaffold 300 crimped to a balloon 15. The distal end 302 of the scaffold 300 is nearest the distal end 17b of the balloon 15 and the proximal end 304 is nearest the balloon proximal end 17a. The tip of or the most distal end 12 of the balloon catheter is shown. A guide wire or mandrel 8 extends from the tip 12, exiting from a lumen of the catheter shaft 2. The scaffold crimped to the balloon (according to D-min or other minimum crimped diameter) can be scaffold 300 or scaffold 400, discussed infra. Scaffolds 500, 600 and 700 may also be used in place of scaffold 300.

As mentioned earlier, when compared to a scaffold that has a comparatively thick wall thickness, such as the scaffold described in US 2010/0004735 or the ABSORB GT1 bioresorbable scaffold, the thin-walled scaffold having a similar scaffold pattern was found to exhibit a significantly higher occurrence rate of strut overlap or underlap (hereinafter MBOL) similar to that shown in FIG. 3C. Higher MBOL occurrence rates are more likely when the width of the link containing the markers is made wider to accommodate the same overall volume of the marker material as used in a scaffold having higher wall thickness struts. The MBOL can also be higher when a more aggressive crimp is employed—e.g., D-min crimp profile.

Furthermore, when the same volume marker bead is attached to both the thin-walled and thick-walled scaffolds and the marker is made flush with the abluminal and luminal surface of the link, the marker bead region must adopt a flatter and broader shape, which enforced shape deforms the structure 21a and 21b to increase the propensity for strut overlaps in the marker bead region, since the marker structure develops a higher aspect ratio to accommodate the marker and/or there can be residual strain from the marker swaging process, which makes the marker structure 21 more susceptible to twisting out of plane. TABLE 1 summarizes these findings.

Paragraphs [0073] through [0083] of U.S. application Ser. No. 14/738,710, which shares a common inventor with this application, describes the factors affecting a scaffold's ability to retain a marker in a hole and the special challenges faced when a wall thickness is less than 160 microns, or less than 125 microns. Additionally, the '710 application explains how the marker-holding structure must be wider for reduced wall thickness and same radiopaque material volume if the marker will remain flush—as desired—with the abluminal surface of the strut (therefore, higher aspect ratio and greater tendency for twisting movement and overlap during crimping). A wider and flatter marker structure increases the aspect ratio (AR) of the link's width to its wall thickness, which increases the likelihood that the link will twist when it comes in contact with an adjacent strut or crown.

In one example the aspect ratio (AR) of the marker link for a thin-walled scaffold having a 93 micron wall thickness, compared to an AR for a scaffold having a higher wall thickness of 158 microns, e.g., as described in US 2010/0004735, and the same volume of marker material held by both the 93 micron and 158 micron marker structures, is about 4.5 (AR=ts/t=419 micron/93 micron=4.5). For the scaffold having the 158 micron all thickness the AR is about 2 (AR=ts/t=322/158). Thus, for the same volume of marker material and reduction in wall thickness from 158 microns to 93 microns the AR increases 2.5 times. Given this significant increase in the aspect ratio it will be appreciated that the tendency for the marker link to twist when it comes in contact with adjacent struts or crowns during crimping, and/or the struts to overlap/underlap the marker link can be appreciated.

It is known that during crimping, scaffold bar arms angles reduce and adjacent bar arm struts naturally move toward the link of a w crown. In this crimping event, the w crown's "outboard radius" and its center point (usually located outside the link) play a crucial role in guiding the way the scaffold struts crimp. In fact, the center point of this outboard radius tends to act as a pivot point that guides the initial behavior of the struts and limits the extent of strut motion toward the marker link features. In this second respect, the MBOL occurring between strut and marker link features are closely related to this outboard radius and pivot point location. In the case of the w crown with marker links 20 and a thin-walled scaffold design, the center points of the w crown were initially positioned within the marker structure 21 region. Therefore, during crimping, the strut closure behavior was not kinematically limited, resulting in frequent occurrences of overlapping/underlapping with the marker link. To reduce the MBOL occurrence rate, the center points of the W crown with the marker structure 21 may be moved to an area outside of the marker structure 21. Hence, during crimping, when the struts of the w crown move toward the marker structure 21, they should avoid pressing into and slipping into an overlap or underlap state which induces torsion in the w crown and/or link.

Figure 4:
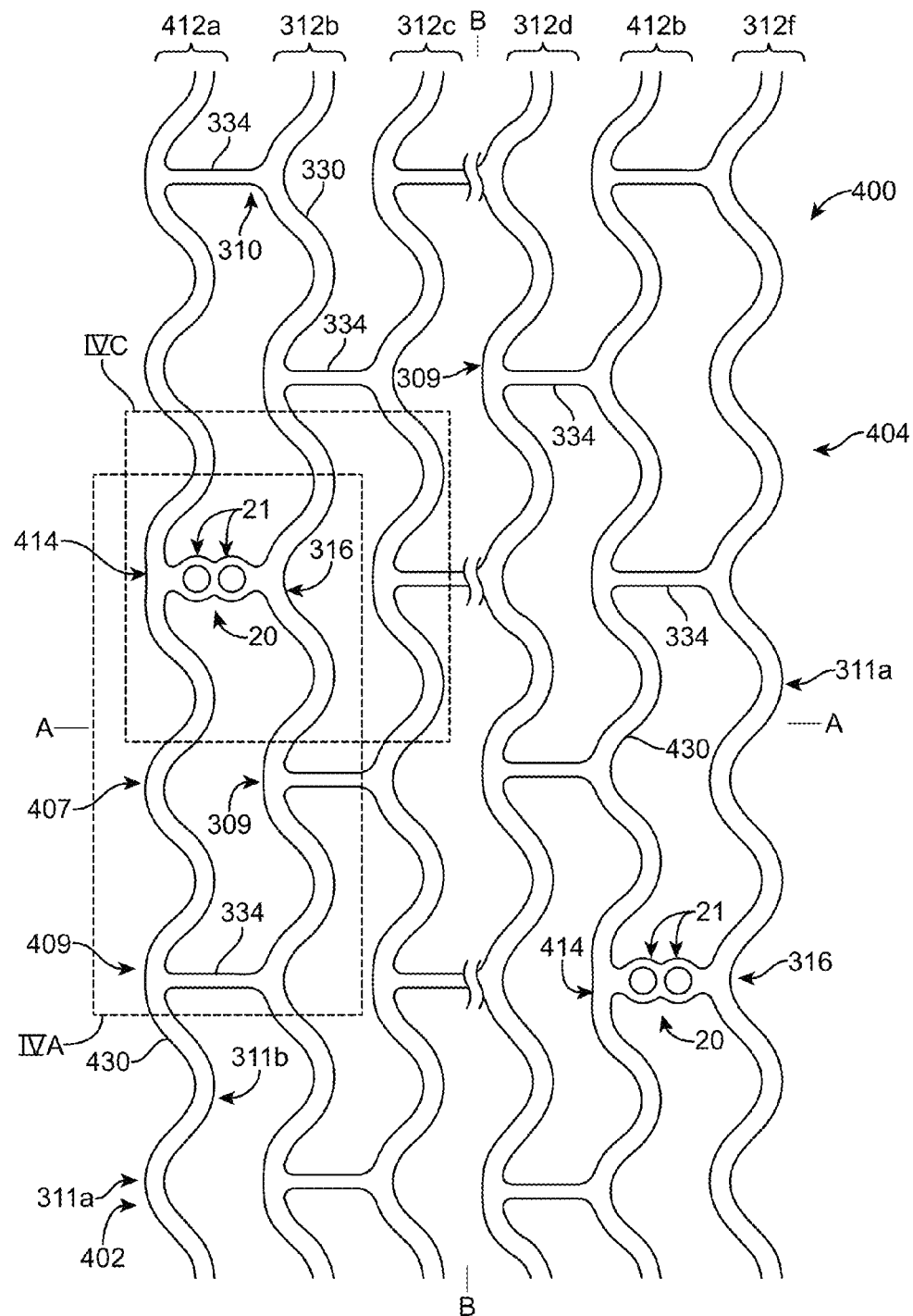
FIG. 4 shows end portions of a scaffold according to another embodiment. The end portions include a link connecting adjoining rings and containing a marker. The rings have a W crown formed in-part by the marker link. The W crown is modified to accommodate a marker structure.

FIG. 4 shows a partial, planar view of end portions of a scaffold according to another embodiment, or scaffold 400. The left or distal end portion 402 (i.e. the left side of FIG. 4) includes sinusoidal rings 412a, 312b, and 312c where ring 412a is the outermost ring. Ring 412b and ring 312c are adjoined by two links 334 and the marker link 20. Ring 312c and ring 312d are adjoined by three links 334 that extend parallel to axis A-A. The right or proximal end portion 404 (i.e. the right side of FIG. 4) includes sinusoidal rings 312d, 412b, and 312f where ring 312f is the outermost ring. Ring 312d and ring 412b are adjoined by three links 334. Ring 412b and ring 312f are adjoined by two links 334 and the marker link 20. Thus, scaffold 400 has a marker link 20 extending between and adjoining the outermost link with the adjacent ring. The scaffold 400 may have 15, 18 or 20 rings 312 interconnected to each other by the links 334.

Scaffold 400 has the same features as described earlier for scaffold 300, except as follows. Rings 412a and 412b are sinusoidal and adjoined to neighboring rings by W-crowns 414 and Y-crowns 416 (as in the case of rings 312a and 312e), but the ring structure for rings 412a and 412b near marker 20 is modified to avoid overlapping struts when the scaffold is crimped to a minimum theoretical crimp diameter (D-min), as discussed earlier.

Figure 4C:
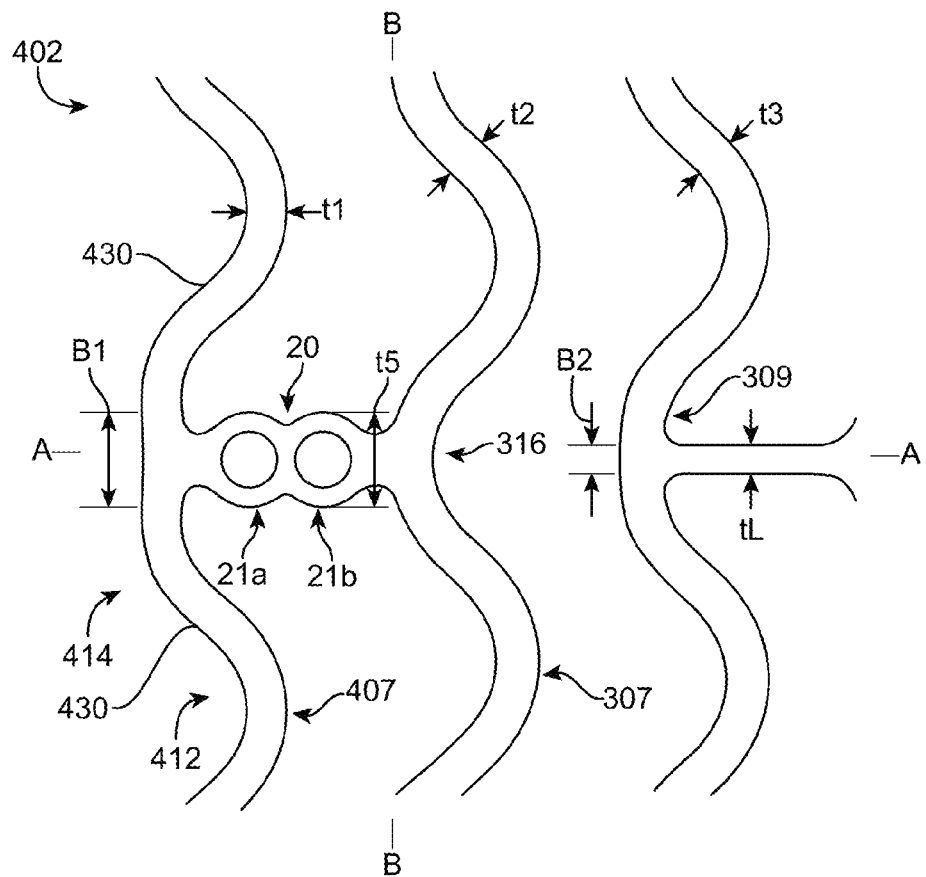
FIG. 4C shows section IVC of the scaffold of FIG. 4.
Figure 4D:
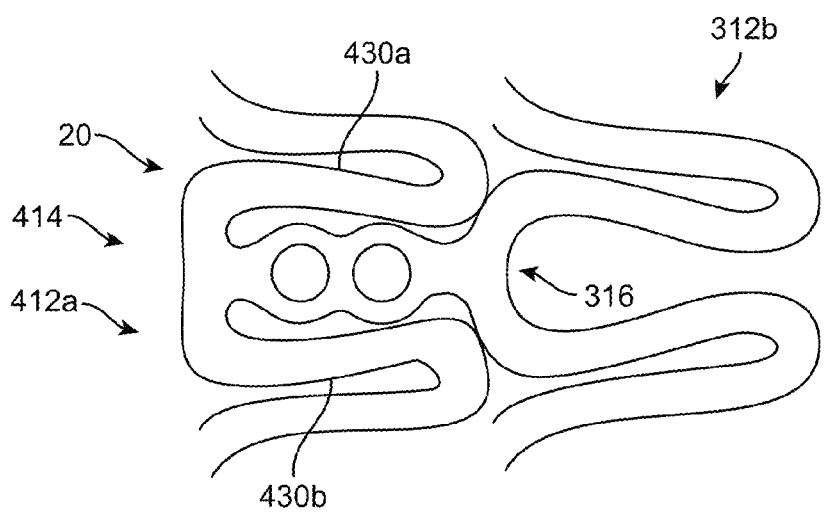
FIG. 4D shows the scaffold of FIG. 4 in a crimped state.

Referring to FIGS. 4A and 4C there is shown close-up views of scaffold 400 at the sections IVA and IVB from FIG. 4, respectively. To avoid the overlap discussed earlier the space between struts portions of the w-crown at the marker for ring 412a and ring 412b is increased. This modification is indicated in the drawings by w-crown 414. The lengthened crown (along axis B-B) provides more space between the strut 430 and marker structure 21a, 21b to avoid the overlap (the resulting crimped shaped with this modification is shown in FIG. 4D). In contrast to w-crowns 309 not associated with the marker link 20, w-crown 414 modifies the scaffold structure near the marker 20 in at least one of ways (1), (2) and (3):

(1) The flat, or non-curved surface portion B1 of the crown is increased in direction B-B over other w-crown 309 flat surface parts B2, e.g., an increase of between about 350% to about 400% for a marker link maximum width (ts) that is about 200% greater than a non-marker link width (tL).

(2) The distance from the w-crown 414 (crest) to the adjacent u-crown 407 (trough) is increased as compared to the distance from the y-crown 316 (crest) to the adjacent u-crown 307 (trough) of ring 312b, and/or for any of rings 312 the distance from a w-crown 309 (crest) or y-crown 310 (crest) to an adjacent u-crown 307 (trough). This is indicated in the drawings by comparing the distance X412 to the distance X312, which measure the length from the crest center to the trough center of rings 412 and 312, respectively. The distance X412 may be about 15% greater than X312 for a marker link maximum width (ts) that is about 200% greater than a non-marker link width (tL).

(3) The distance from the crest 414 to the adjacent crest 407 is greater than the distance from the crest 407 to the crest 409 or L1 is longer than L2 in FIG. 4A, e.g., L1 is about 10% longer than L2, and/or L1 is about 5% longer than the distance between any adjacent crests for rings 312a, 312b, 312d, and 312f and for a marker link maximum width (ts) that is about 200% greater than a non-marker link width (tL).

The features of ring 412a apply equally to ring 412b within the vicinity of marker link 20. FIG. 4B shows a view of the portion 302, where ring 412a is shown in phantom over ring 312a from scaffold 300. The space added between the marker link 20 and strut 430 is indicated by "increased space" in the drawing. The difference in half-periods of the sinusoidal ring portions (X412, X312) extending between the marker link y-crown and w-crown, respectively, can also be seen in this drawing. Also, the features of ring 412a are symmetric about the w-crown 414. Therefore, the modifications of at least one of (1), (2) and (3), discussed supra, apply to both sides of the w-crown 414.

According to another aspect of the scaffold 400 in connection with the "increased space" indicated for scaffold 400 to avoid MBOL or overlap, for some embodiments of making the scaffold marker link and connecting rings to avoid overlap, it is advantageous to also factor in deformation of the structure 21a, 21b when a marker element, rivet or bead, is swaged into the hole.

FIG. 4D shows a portion of scaffold 400 in a crimped state, where the scaffold has been crimped to D-min. As can be seen here, the added space between the strut-portions 430a, 430b of the w-crown 414 at the marker link 20 results in no overlap or underlap when the scaffold is crimped to the theoretical minimum crimp diameter, D-min. Specifically, FIG. 4 shows that with the modification to the ring 412 having the W crown 414 connection to the marker link 20 the struts and/or U crowns adjacent and above and below the marker structure are separated by a distance that is greater than or equal to the maximum width (ts) of the marker structure when the scaffold is crimped to D-min. There is no overlap when the scaffold having the ring 412 is crimped to D-min. The marker link is everywhere between the crowns and struts when the scaffold is crimped to about D-min.

It has been found that when a thin-walled scaffold similar to scaffold 300 was tracked through a simulated calcified and tortuous anatomic model, distal end ring distortion was observed due to struts lifting and catching on obstacles along their path. Additionally, there was potential for the marker structure 21 and holes 22 to deform/stretch resulting in potential dislodgment of the marker material. To address this concern for marker material separation from the thin-walled scaffold, the marker link may be made more flexible in bending by lengthening the link and/or reducing the width of the link portions connecting the structure 21 to the adjacent Y or w crown. This change results in a more flexible hinge region adjacent to the marker structure 21, thereby localizing the deformation to points away from the structure 21 to protect the marker hole 22 from significant deformation. The change also makes the distal and/or proximal ends of the scaffold more flexible and conforming to the balloon, thereby reducing the potential for strut lifting and catching on obstacles during delivery to a target site.

Figure 5:
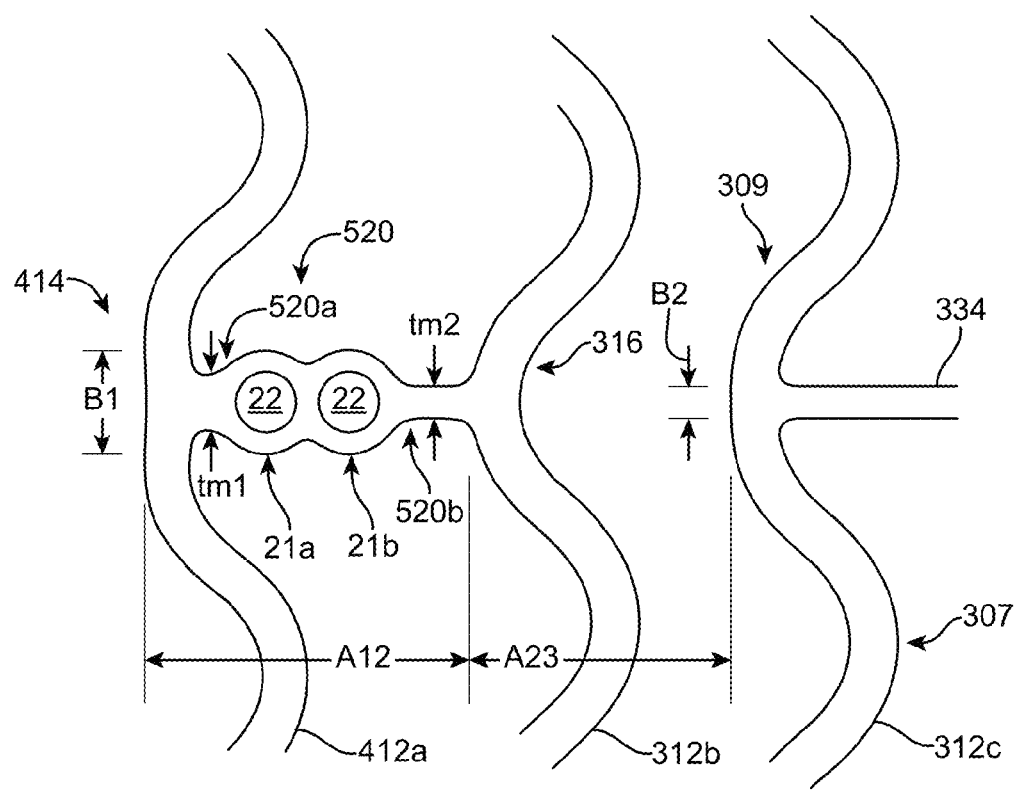
FIG. 5 is a partial view of a scaffold distal end portion according to another embodiment.

FIG. 5 shows a close up view of another embodiment of a scaffold, or scaffold 500. The view of FIG. 5 is the same as for section IVC of FIG. 4 and scaffold 500 has all the features of scaffold 400, except that the marker link adjoining rings 412a and 312b and rings 412b and 312f is modified. Marker link 520 differs from marker link 20 in that an additional link 520b is added, or the existing link to the right of marker structure 21b (see marker link 20) is lengthened. This added, or lengthened marker link portion results in an increase of the distance A12 as compared to when marker 20 is used. Also, distance A12 is longer than distance A23 separating rings not adjoined by a marker link, e.g., rings 312b and 312c in FIG. 5. The same modification—marker link 520 replacing marker link 20—is made to the marker link extending between rings 412b and 312f. Marker link 520 may also replace marker link 20 in scaffold 300 (at both proximal and distal ends). In such case, the same features discussed in respect to scaffold 400 with link 520 also applies to scaffold 300 having link 520.

It was found that when link 20 was replaced by marker link 520 there was less tendency for the radiopaque material held by the marker structure 21 to become dislodged or separate from the scaffold when the scaffold was crimped, balloon expanded or tracked through a tortuous vessel. The reason for the improved retention may be understood by consideration of the strain energy distribution over the link when the scaffold is deformed, or the y-crown 316 of ring 312b moves relative to the w-crown of ring 412a.

If crown 316 of ring 312b moves radially outward or inward relative to crown 414 of ring 412a, or the crowns move in opposite directions along axis B-B, then the marker link 20 deforms. A significant portion of the strain energy in the link 20 resulting from this deformation is carried in the marker structure 21a, 21b because the link portions to the left and right of structure 21 are relatively short and thick (as such, there is little deformation in this part of the marker link and therefore less strain energy carried here). Since the load must be reacted somewhere along the marker link when the ring movement is enforced (i.e., regardless of the link stiffness the rings will move relative to each other by a prescribed magnitude because the ring movement occurs by an enforced displacement or overwhelming force, such as by a crimper jaws closing down on the scaffold), the strain energy is mostly carried in the marker structure 21, which deforms more easily than the short and thick link portions near the crowns. This deformation can change the hole shape that the marker material sits in, thereby resulting in a loss of retention. By lengthening the link portion of the marker 20, or adding link 520b that is significantly longer than link 520a, which represents the length for the link portions at left and right sides of structure 21 for link 20, the strain energy is instead carried less in structure 21 and more by link 520b. As a result, there is less tendency for the marker material to become dislodged during crimping or bending of the scaffold because the marker holes 22 retain their shape during these loading events. In other words, the deformation of the link occurs mostly in the long slender portion 520b so that the holes 22 can retain their shape. Additionally, the link 520b also increases the flexibility of the link, thereby enabling the ring 312b or 312f to move more easily relative to ring 412a and ring 412b, respectively. This aspect is advantageous to avoid problems with the distal end ring flaring or protruding from the balloon when the catheter is navigated about tight vasculature (objective (iv), supra). It is also noted that marker 720, discussed in connection with FIG. 7, similarly addresses objectives (iv) and (iii).

According to one example, the link 520b forming the y-crown 316 has a thickness (tm2) that is about 60% less than the thickness (tm1) of the link portion 520a connecting the forming the w-crown 414. Additionally, the length A12 is about 27% longer than the length A23, so as to accommodate the link 520 with added link portion 520b.

When a thin-walled scaffold, crimped to a delivery system, was tracked through a simulated calcified and tortuous anatomic model, distal end ring distortion was observed due to struts catching on obstacles along their path. To understand the possible causes for the strut catching, a thin-walled scaffold was crimped to a delivery system of the same configuration and placed in bending similar to what existed in the anatomical model observed under microscope. It was observed that the balloon was under compression on the inner curve of the bend and tension on the outer curve of the bend. Under tension, the balloon stretched and conformed to the curve. If the w-crown associated with the marker link happened to be positioned on the outer curve of the bend, it would flare-out (see FIG. 6B) instead of conforming to the underlying curved balloon material at the distal end 15a. The w-crown section of the scaffold remains straight since it is stiff due to the marker material and structure 21.

Figure 6:
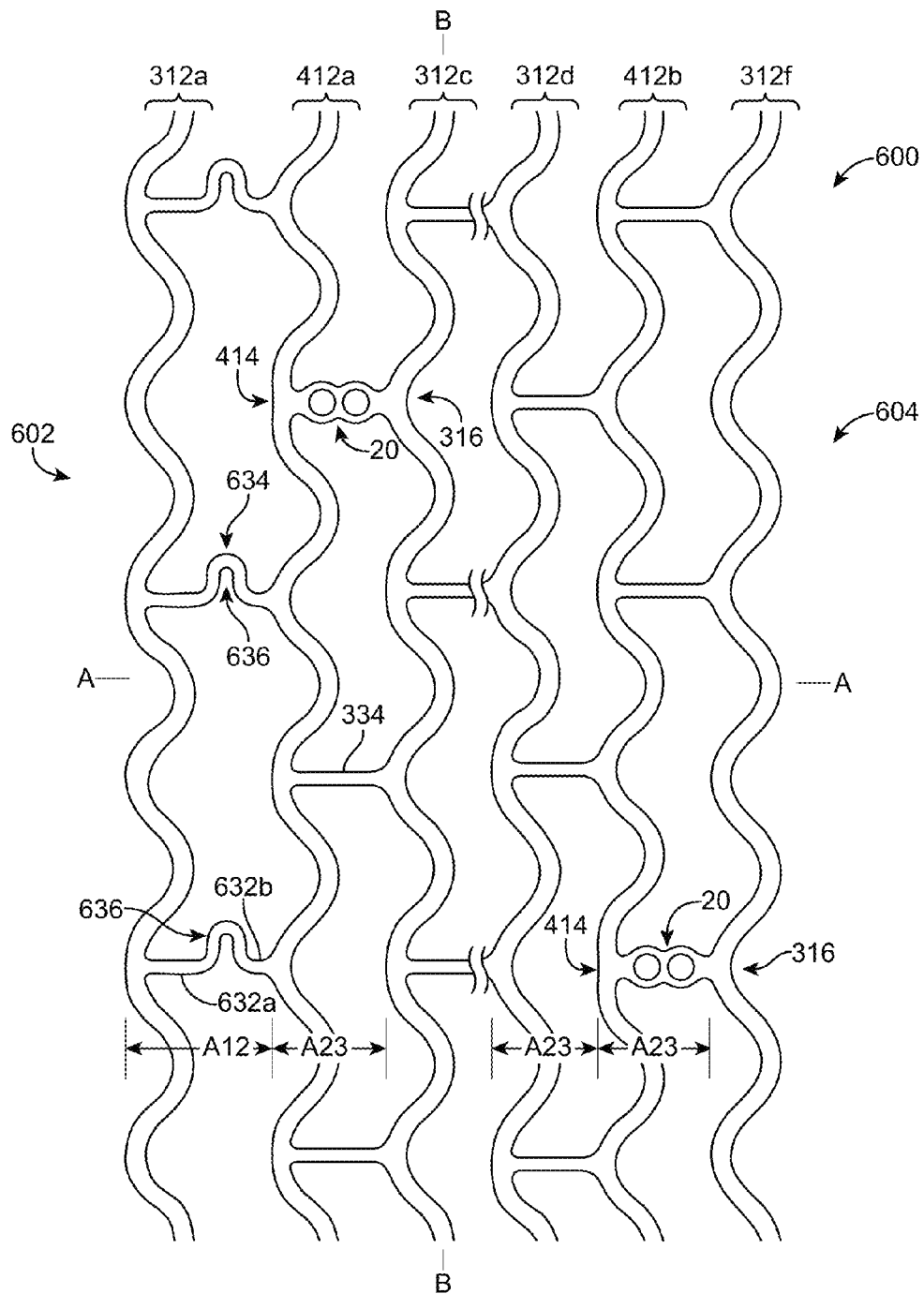
FIG. 6 shows end portions of a scaffold according to another embodiment. The distal end portion is different from the proximal end portion. Non-linear link struts connect the outermost distal ring to an inner ring and a marker link is between inner rings at the distal end portion.

FIG. 6 shows a partial, planar view of end portions of a scaffold according to another embodiment, or scaffold 600. The left or distal end portion 602 (i.e. the left side of FIG. 6) includes sinusoidal rings 312a, 412a, and 312c where ring 312a is the outermost ring. The right or proximal end portion 604 (i.e. the right side of FIG. 6) includes sinusoidal rings 312d, 412b, and 312f where ring 312f is the outermost ring. As can be appreciated from FIG. 6 the distal end portion 602 is different from the proximal end portion 604. This modification to scaffold 300 or scaffold 400 is made to address occurrences of a non-confirming distal, outermost end ring when the scaffold mounted on a balloon catheter is navigated around a sharp turn in vasculature.

The proximal end portion 604 of scaffold 600 is the same as the proximal end portions 304 or 404 associated with scaffolds 300 and 400, respectively. The distal end portion 602 is modified from distal end portions 302 or 402 in the following ways.

The (distal) marker link 20 or marker link 520 is located between inner distal end rings 412a and 312c, in contrast to the (proximal) marker link 20 or 520 located between the outermost distal ring 312f and inner ring 412b. This change to the distal end 602 is desirable for at least one of reasons (a) and (b):

(a) Improved conformity with distal end balloon: the marker link 20 is stiffer in bending than link 634 or, for that matter, link 334, which can result in separation of the distal outermost ring from the balloon distal end. When it is not desirable to modify the marker link structure, or it is not feasible (e.g., because the structure is needed to provide sufficient surface area to hold the desired volume of radiopaque material), a significant reduction in the flexural rigidity of the link connecting the outermost ring 312a to interior ring 412a may be achieved by moving the marker link 20 to between inner rings. The ability then to dramatically decrease the flexural rigidity between the outermost two rings 312a—objective (iv)—is addressed.

(b) Less strain in marker-holding structure: when the scaffold is navigated about a sharp turn it is the outermost rings that will experience the highest strain due to the scaffold being bent. For embodiments of scaffolds where it is not desirable to make less stiff in bending the outermost ring relative to adjacent inner ring (e.g., where it is important to avoid a decrease in radial stiffness for the outermost ring or to avoid increased spacing between rings for purposes of drug coverage or vessel support, both of which can occur when the connecting links are lengthened to make more flexible), by moving the marker link 20 to a location between inner rings the bending strain on the link 20 that can cause the marker material to become dislodged is avoided or mitigated. That is, because the bending strain in the scaffold (produced when a sharp turn is made by the catheter) is higher between the outermost ring and adjacent inner ring than between inner rings, by locating the link 20 to between inner rings (without a need to change the marker link structure) the bending strain on the marker structure 21 is less. Objectives (ii) and (iii) are met.

The scaffold 600 differs also from scaffolds 300 and 400 by the link type used to connect the outermost ring to the inner ring—that is, the link 634 connecting ring 312*a* to ring 412*a*. The outermost distal ring 312*a* is adjoined with ring 412*a* by three non-linear link struts 634 that are significantly more flexible in bending than are link struts 334 connecting interior rings. This also helps with reason (a) for using a scaffold 600 pattern for the distal end.

A non-linear link strut may take on a variety of shapes, but with certain restraints such as providing sufficient space for crimping, e.g., D-min crimped profile. The type shown in FIG. 6 has a U-shaped medial portion 636 connected to the respective y-crown and w-crown by a short, straight link portion and long, straight link portion, respectively. The link portion connecting the portion 636 to the w-crown is longer than the link portion 632*a* connecting to the y-crown in order to provide sufficient clearance for ring struts during crimping (as explained below). With this clearance provided the w-crown 309, formed by the link portion 623*a*, may be crimped down to D-min without U-shaped portion 636 interfering with struts 330 or struts 330 overlapping U-shaped portion 636 in the crimped state.

Figure 6A:
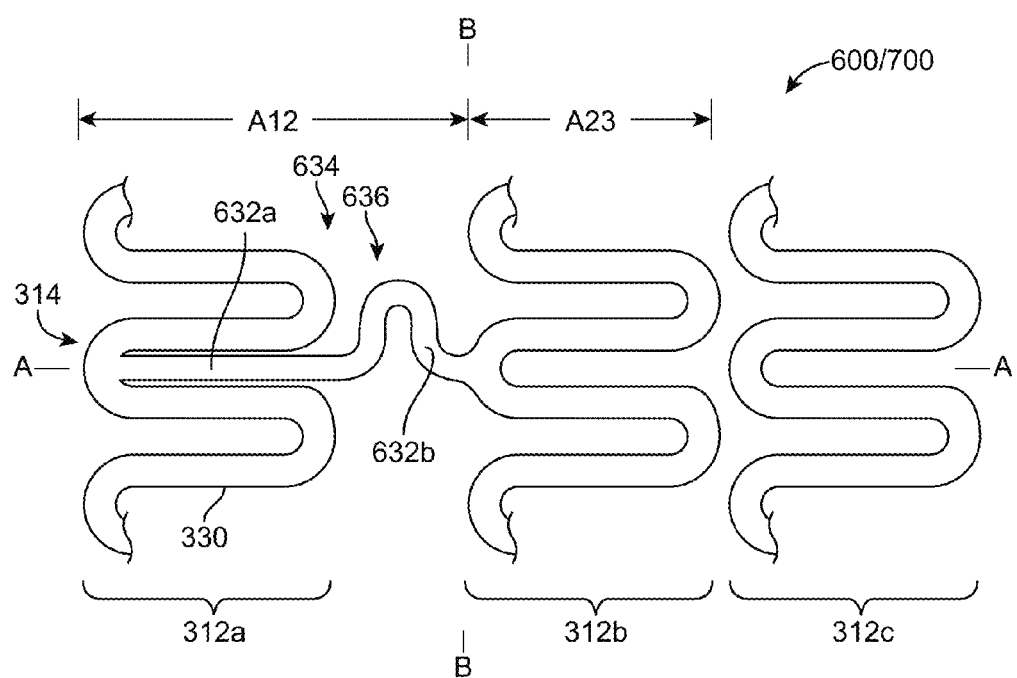
FIG. 6A is partial view of the scaffold of FIG. 6 in a crimped state.

Referring to FIG. 6A there is shown a crimped side profile for scaffold 600. Shown is the link 634 long straight link portion 632*a* and short straight link portion 623*b* with the U-shaped medial portion 636. The length A12 (length measured with respect to axis A-A) may exceed the length A23 by about the length of the U-shaped portion 636, or the sum of the lengths of portions 632*a* and 632*b* is about equal to A23, less the strut width of a ring. In one example, the length A12 is about 40% longer than the length A23.

In other embodiments the U-shaped portion 636 may be replaced by links having a smaller moment of inertia for a region between portions 632*a* and 632*b*, an S-shaped, notched portion, or narrowed portion replacing U-shaped portion. Examples of these link types are described in US20140039604 at FIGS. 14B, 14C, 14D, 14E, and 14F, and accompanying paragraphs [0223]-[0229]. A "non-linear" link strut means any of these links.

Figure 6B:
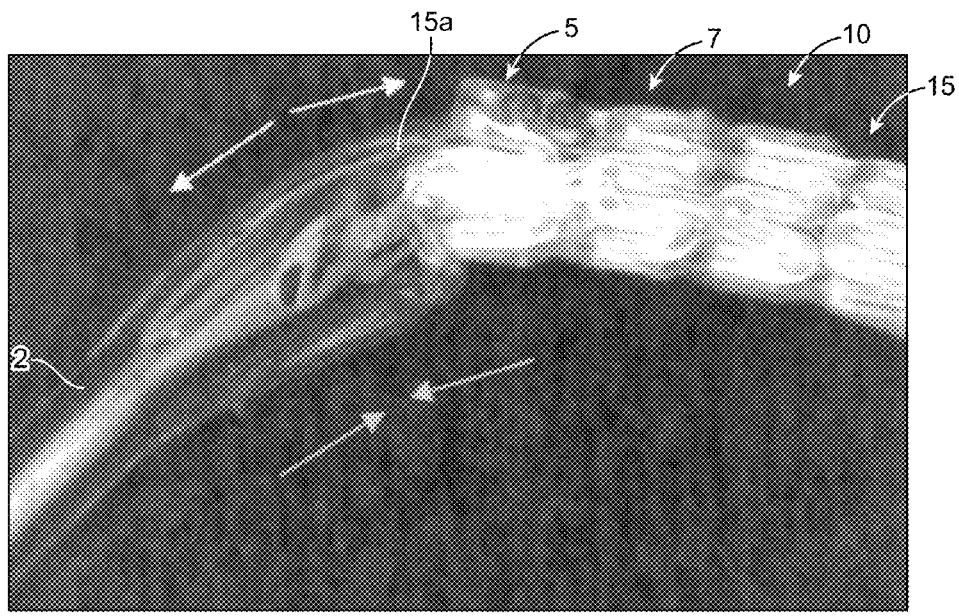
FIG. 6B is an image of a catheter distal end in a bent configuration showing a distal ring of a scaffold flaring or protruding outward from the balloon distal end.

FIG. 6B is an image showing a deformed distal end of a medical device comprising a balloon catheter having a shaft 2 and a scaffold 10 crimped to the balloon 15. As can be seen in this view, when the catheter is directed about a sharp turn (as tracked over a guide wire) the balloon distal end and shaft conform to the angle of the turn but the scaffold distal end 7 does not. More specifically, the outermost ring 5 is flaring or protruding outwards from the distal end. This protruding structure 5 can get caught on walls of vasculature. The most pressing concern with this orientation of the scaffold relative to the balloon distal end is damage that might be caused by the ring 5 catching on the vasculature and damaging the scaffold (due to excessive bending strain). The damage that can occur has been mentioned earlier. First, the marker link structure can be deformed and result in dislodgment of the marker material. Second, the strain can result in fracture of, or crack propagation within the ring 5.

One solution to this problem may be to make the end rings stiffer in bending, so that the vessel obstruction yields to make space for the flaring or protruding scaffold end. For example, one could make the end rings more thick or increase the number of connecting links between the outermost ring and inner ring. It is preferred, however, to instead make the rings less stiff so that the scaffold end will conform more to the balloon distal end. It is also preferred to limit the load put on a marker link, for reasons previously stated. Scaffold 600 (or scaffold 700, infra) meets this need.

Figure 6C:
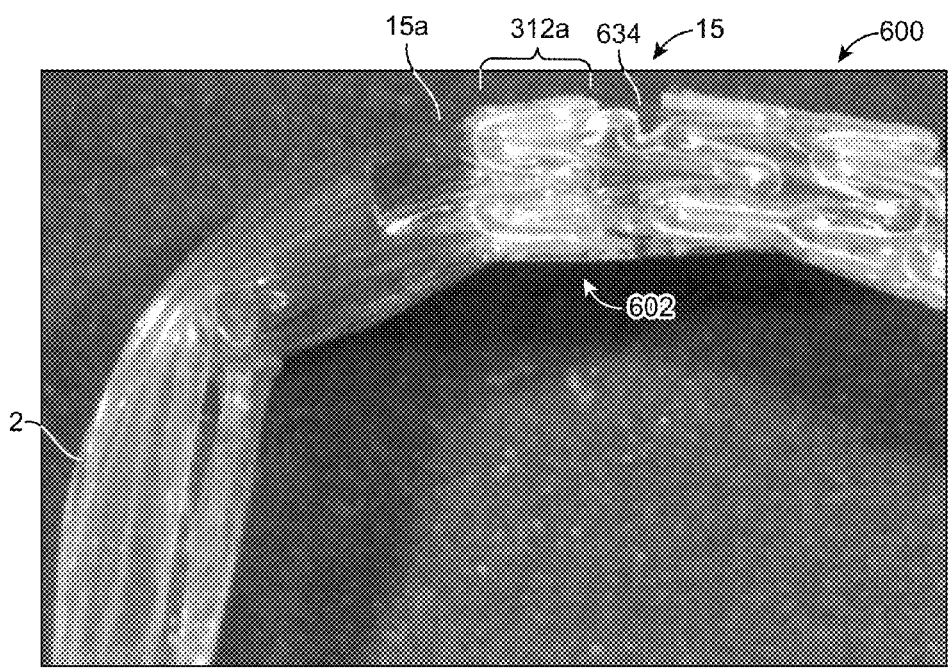
FIG. 6C is an image of a catheter distal end in a bent configuration showing the distal ring of a scaffold according to FIG. 6. The distal end ring no longer flares outward when the catheter is placed in bending.

FIG. 6C is an image of scaffold distal end 602 mounted on the balloon 15 distal end 15*a* as the catheter makes a similar sharp turn in vasculature. As can be seen, by reducing the bending stiffness of the ring 312*a* relative to the inner ring (ring 312*b*) the end ring 312*a* conforms to the shape of the balloon distal end 15*a*. The end ring 312*a* does not flare or protrude out as in the case of scaffold 5. The links 632 act as hinges to accommodate compression and tension that a bend would exert on the distal end ring when the crimped scaffold is put on a bend.

Distal end scaffold conformity with the balloon distal may also be achieved by modifying the marker link structure to become more flexible in bending. In effect, the w-crown formed by the marker link according to the discussion can greatly reduce the stiffness at the w-crown associated with the marker link 314. The thin-walled scaffold design can then have the marker link connected to the outermost ring without the flare-out problem discussed earlier.

FIG. 7 shows a partial, planar view of end portions of a scaffold according to another embodiment, or scaffold 700. The left or distal end portion 702 (i.e. the left side of FIG. 7) includes sinusoidal rings 312*a*, 312*b*, and 312*c* where ring 312*a* is the outermost ring. The right or proximal end portion 704 (i.e. the right side of FIG. 7) includes sinusoidal rings 312*d*, 412*b*, and 312*f* where ring 312*f* is the outermost ring. As can be appreciated from FIG. 7 the distal end portion is different from the proximal end portion. This modification to scaffold 300 or scaffold 400 is also made to address occurrences of a non-confirming distal, outermost end ring when the scaffold mounted on a balloon catheter is navigated around a sharp turn in vasculature.

The proximal end portion 704 of scaffold 700 is the same as the proximal end portions 304 or 404 associated with scaffolds 300 and 400, respectively. Moreover, the distal end portion 702 shares some of the characteristics of scaffold 600 at the distal end portion 602 except as follows.

The marker link 720 (FIG. 2B) is located between the outermost ring 312*a* and inner ring 312*b*, as opposed to the marker link 20 or 520 located between inner links, in the case of scaffold 600. The marker link for scaffold 700 is also different from the marker link of prior embodiments. Marker link 720 has the marker structure 21 orientated vertically rather than horizontally, as in the case of marker link 20 or link 520. That is, the marker structure 21*a* is offset from the marker structure 21*b* along axis B-B rather than axis A-A. There is a long, straight link portion 732*a* connecting the structure 21 at one end and forming the w-crown 314, and a shorter link 732*b* at the opposite end forming the y-crown 316.

The outermost ring 312a for scaffold distal end portion 702 is connected to the inner ring 312b by the one marker link 720 and two of the non-linear links 634 used in scaffold 600. Adjoined inner rings are not connected by a marker link 720 or link 634. The link 334 is used. The marker link 720, in contrast to the marker link 20, is more flexible in bending due to the length of portion 732a and is favorably located between the outermost ring and adjacent inner ring to more easily locate the ends of the scaffold under fluoroscopy. Additionally, one or more of the following advantages are also present when marker 720 is used. First, the marker is more flexible so that the outermost ring will more easily conform to the balloon when the catheter is navigated about a tight turn in the vasculature. In this sense marker 720 has some of the same advantages as marker 520 (objectives (ii) and (iii)). And no change is needed to the ring structure to enable a crimping of the ring having the w-crown formed by the marker link. The ring 312a can be crimped to D-min because the structure 21 does not interfere with the ring structure 21 (objective (i)).

Figure 7A:
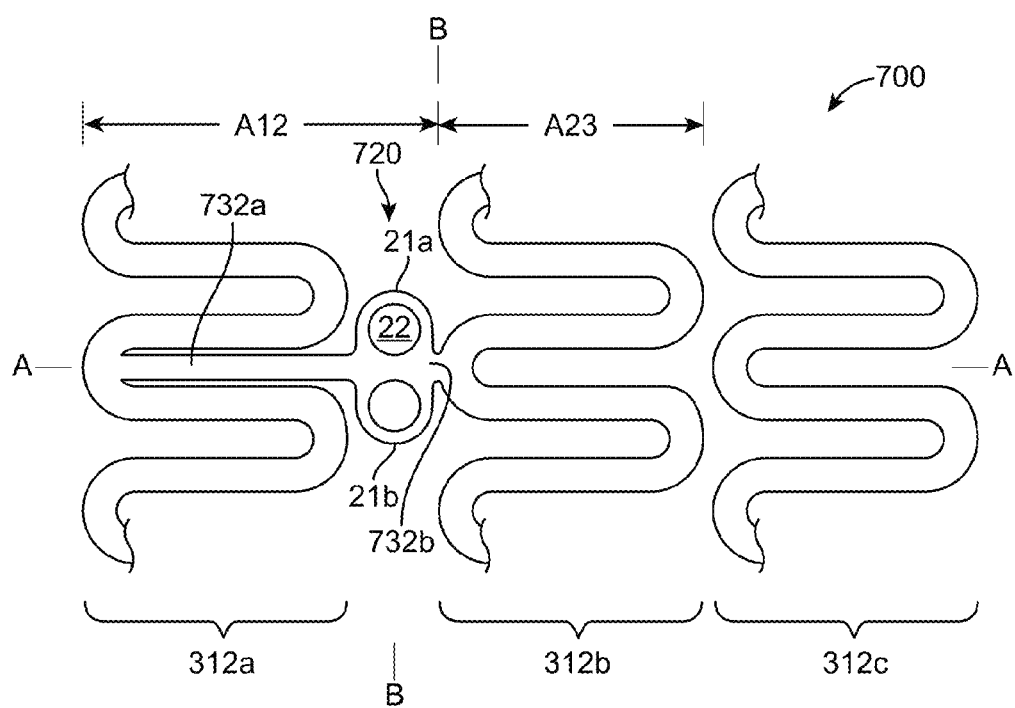
FIG. 7A is a partial view of the scaffold of FIG. 7 in a crimped state.

FIGS. 6A and 7A show the crimped states of scaffold 700 near the marker 720 and link 634 and lengths between rings A12, A23. As can be appreciated from these views, the portions 732a and 632a of the marker and link, respectively, have a length that allows the outer ring 312a to crimp down to D-min without interference from the U-shaped portion 636 or marker structure 21. As can be seen in these views, the structure 21 having holes 22 and U-shaped structure 636 are between a U-crown adjacent a W-crown of the ring on the left and a U crown adjacent a Y crown of the on the right.

Figure 7B:
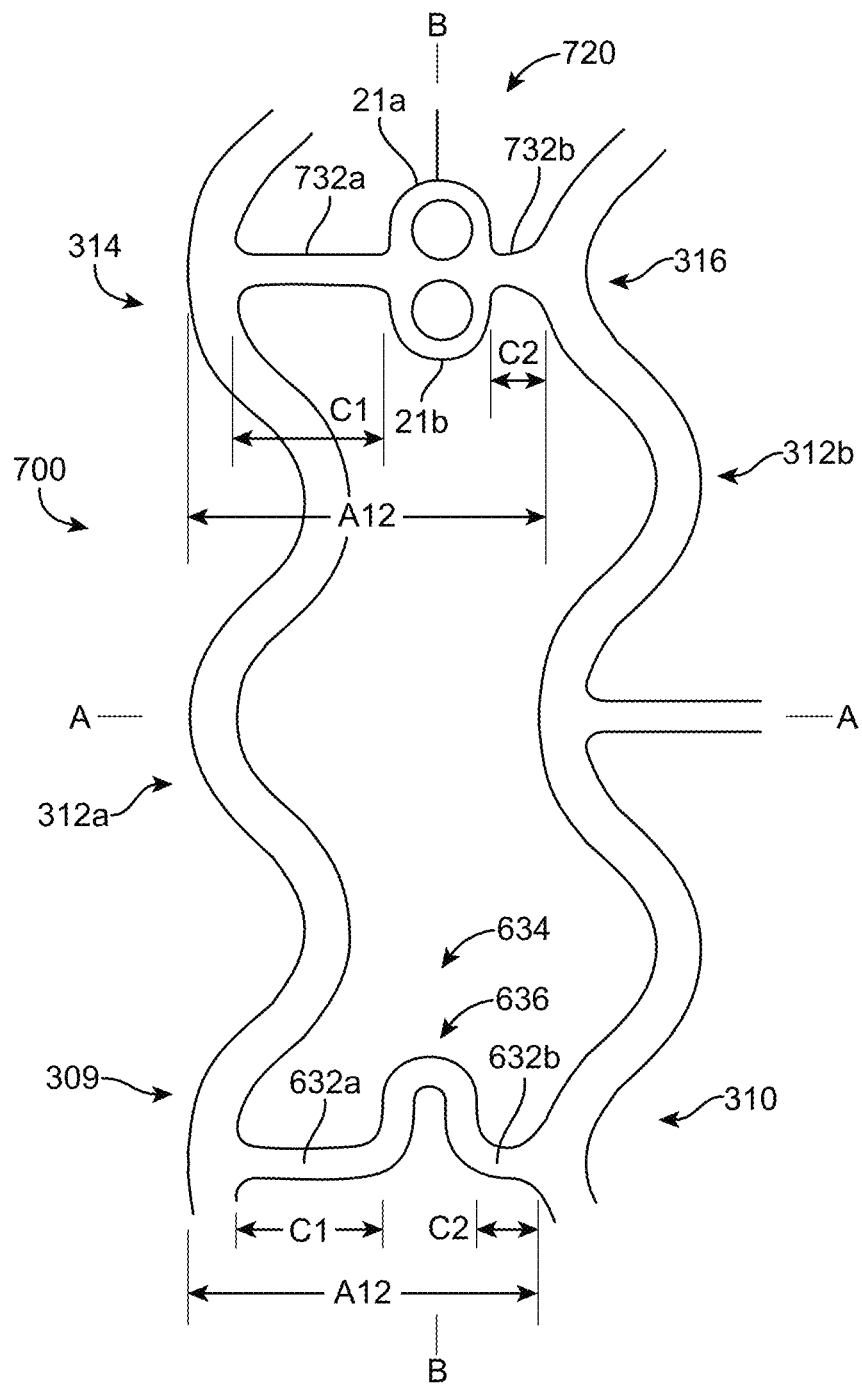
FIG. 7B is a partial view of the scaffold of FIG. 7 taken at section VII in FIG. 7.

Referring to FIG. 7B there is shown a close up view of section VII from FIG. 7. As indicated here, the respective lengths of portions 732a and 732b is c1 and c2. The lengths of portions 632a and 632b are also c1 and c2. Also shown are the lengths A12 and A23 for scaffold 700 (lengths A12, A23, c1 and c2 also apply to the lengths for portions 632a and 632b and ring spacing for scaffold 600). The sum of lengths c1 and c2 is equal to A12 less the length of U-shaped portion 636 and width of the crown. In some embodiments A12 is about 40% greater than A23, c1 is about 36% longer than c2. The length c1 is about equal to the distance between the trough of the adjacent crown and the w-crown formed by portion 732a or 632a, less the width of the crown 314 or strut 330, when the scaffold is in the crimped state (see FIGS. 6A-7A). The marker structure is located to the right of the U-crown adjacent the W-crown formed by the marker link.

Figure 7C:
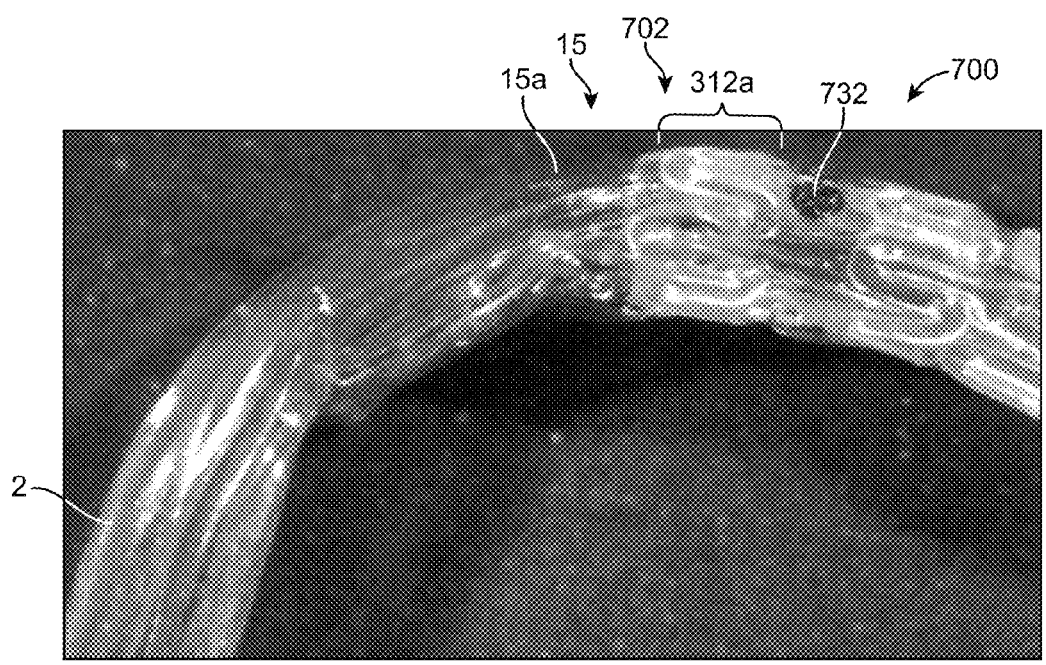
FIG. 7C is an image of a catheter distal end in a bent configuration showing the distal ring of a scaffold according to FIG. 7. The distal end ring does not flare outward when the catheter is placed in bending.

FIG. 7C is an image of scaffold distal end 702 mounted on the balloon 15 distal end 15a as the catheter makes a similar sharp turn in vasculature. As can be seen, by reducing the bending stiffness of the ring 312a relative to the inner ring (ring 312b) the end ring 312a conforms to the shape of the balloon distal end 15a. The end ring 312a does not flare or protrude out as in the case of scaffold 5.

TABLE 2 shows dimensions associated with examples of fabricated scaffolds corresponding to embodiments of the scaffolds depicted in the figures (when an entry has "-", it means the same value as the box immediately to the left. Thus, the value for tm2 for scaffold 400 is 217, and the length B1 for scaffold 500 and scaffold 700 is 374 and 78, respectively).

TABLE 2

| | | FIG. 3/ scaffold 300 (µm) | FIG. 4/ scaffold 400 (µm) | FIG. 5/ scaffold 500 (µm) | FIG. 6/ scaffold 600 (µm) | FIG. 7/ scaffold 700 (µm) |
|---|---|---|---|---|---|---|
| Ring spacing (crown-to-crown, adjoined by marker link or non-linear link) | A12 | 1110 | 1110 | 1300 | 1426 | 1427 |
| Marker link or non-linear link | tm1 | 217 | — | — | 127 | 127 |
| | tm2 | 217 | — | 127 | — | — |
| | ts (max width) | 419 | — | — | — | 749 |
| | c1 | n/a | n/a | n/a | 596 | 596 |
| | c2 | n/a | n/a | n/a | 252 | 254 |
| Ring spacing (crown-to-crown, no marker link or non-linear link) | A23 | 1027 | — | — | 1110 | 1027 |
| Non-marker link | tL | 127 | 127 | — | — | — |
| Crown length | B1 | 79 | 374 | — | 78 | — |
| Crown length | B2 | 78 | — | — | — | — |
| Ring width | t1 | 178 | — | — | 191 | — |
| | t2 | 191 | — | — | 178 | 191 |
| | t3 | 191 | — | — | — | — |
| Wall thickness | w | — | 93 | — | — | — |
| Wavelength (distance between crests) | L1 | 1833 | 1922 | 1922 | n/a | n/a |
| | L2 | 1833 | 1744 | 1744 | n/a | n/a |
| ½ wave length (FIG. 4A: X412 v. X312) | X | 956 | 1089 | 1089 | n/a | n/a |

Referring to TABLE 2 as can be appreciated from the above examples, and discussed earlier in connection with scaffold 300 compared with scaffold 400, 500, 600 and 700; there are changes in the wavelengths, ½ wavelengths, marker link thickness, length, and orientation, non-marker link type and length, ring spacing, and crown width at the marker link, respectively, in response to the needs relating to crimping and/or delivery of the scaffold through a tortuous artery. These relationships apply for a thin-walled scaffold whether in a crimped state or before crimped configuration. Thus, when reference is made to a crimped scaffold, the relationships above also apply. It is also understand that the features of scaffold 400 and/or 500 that are different from scaffold 300 can be incorporated into scaffolds 600 and 700. Or the features of scaffold 400 and/or 500 may not be included in the pattern of scaffolds 600 and 700.

The following discussion relates primary to meeting objective (ii): securing radiopaque material in a scaffold hole provided by a marker structure 21*a*, 21*b*. As mentioned earlier, it has been discovered that for thin-walled scaffolds marker material cannot be reliably retained in a marker hole by frictional engagement with walls of a cylindrical hole. To satisfy objective (ii) in preferred embodiments radiopaque material is secured to any of the scaffolds 300, 400, 500, 600 or 700 by swaging a rivet-like body of the marker material to the marker structure 20, 520 or 720, while not impeding any of the other objectives (i), (iii) or (iv). The attaching and securement of the marker, in some embodiments, does not include any added polymer, adhesive or re-shaping of the cylindrical hole (other than the deformation that occurs during the swaging process). In preferred embodiments a drug-polymer coating is applied after the marker is placed in the hole.

Figure 8A:
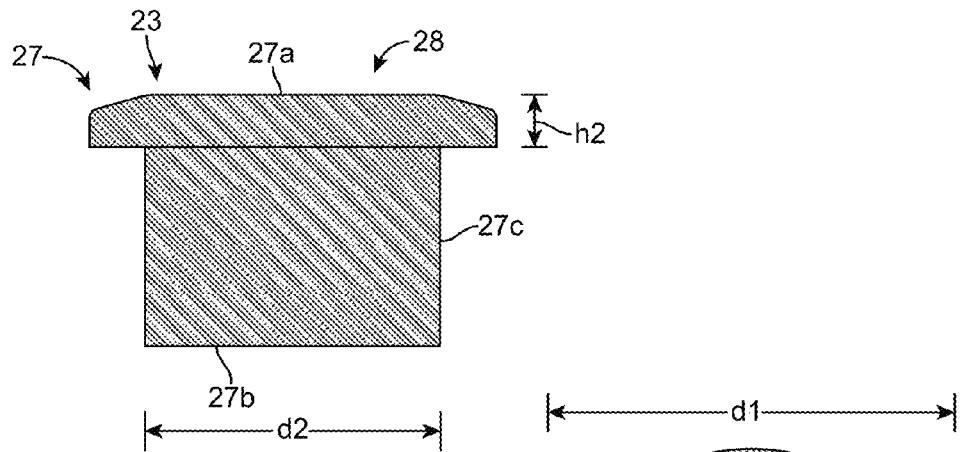
FIGS. 8A-8B show a side and top view, respectively, of a marker according to another embodiment.
Figure 8B:
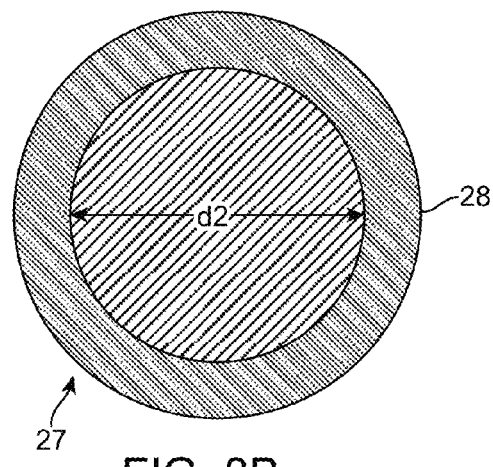

A marker shaped as a rivet is used in place of the spherical marker 25 intended for cylindrical hole. FIGS. 8A and 8B show respective side and top views of the marker 27 shaped as a rivet. The head 28 may include the abluminal surface 27*a* or luminal surface 27*b* of the rivet 27. In the drawings, the head 28 includes the abluminal surface 27*a*. It may be preferred to the have the head 28 be the luminal surface portion of the rivet 27 for assembly purposes, since then the scaffold may be placed over a mandrel and the tail portion of the rivet deformed by a tool (e.g., a pin) applied externally to the scaffold abluminal surface. The rivet 27 has a head diameter d1 and the shank 27*c* diameter d2 is about equal to the hole 22 diameter. The head 28 has a height of h2, which is about the amount the head 28 will extend beyond the abluminal surface 22*a* of the strut portion 21*a*. While not desirable, it may be an acceptable protrusion for a head 28 that does not extend more than about 25 microns, or from about 5 to 10 microns up to about 25 microns from the abluminal surface 22*a*, or a head that extends by an amount no more than about 25% of the strut thickness. The same extent of protrusion beyond the luminal surface 22*b* may be tolerated for the deformed tail of the rivet.

Figure 9:
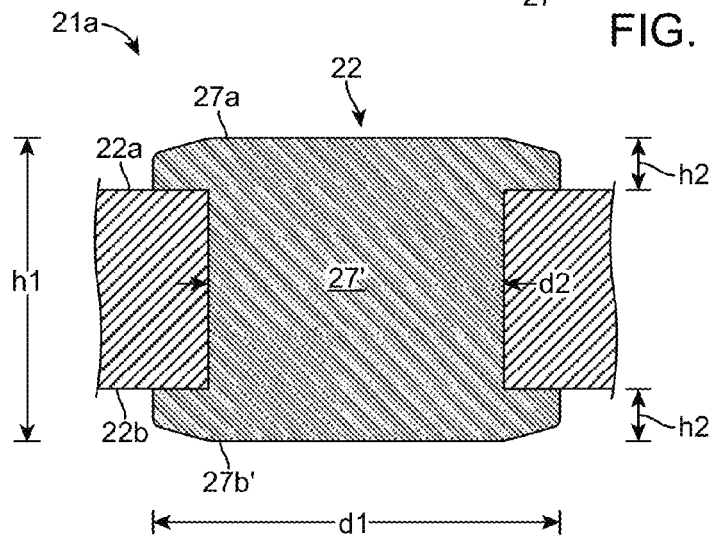
FIG. 9 is a cross-sectional view of a link having a hole and the marker of FIGS. 8A-8B embedded in the hole.

Referring to FIG. 9 there is shown the rivet in the hole 22. The deformed tail 27*b*' secures the rivet 27 in the hole 22. The overall height h1 is preferably not more than about 40% or about 10%-40% greater than the strut thickness (t) and the tail height is about the same as, or within 5 to 20 microns in dimension compared to the head height h2.

The rivet 27 may be attached to the hole 22 of the strut portion 21*a* by first inserting the rivet 27 into the hole 22 from the bore side of the scaffold so that the head 28 rests on the luminal surface 22*b* of the strut portion 21*a*. The scaffold is then slipped over a tight fitting mandrel. With the mandrel surface pressed against the head 28 a tool (e.g., a pin) is used to deform the tail 27*b* to produce the deformed tail 27*b*' in FIG. 9. In some embodiments, the rivet 27 may be first inserted into the hole 22 from the abluminal side so that head 28 rests on the abluminal surface 22*a* of the strut potion 21*a*. With the head 28 held in place by a tool or flat surface applied against the abluminal surface, the tail 27*b* is deformed by a tool, pin, or mandrel which is inserted into the bore or threaded through the scaffold pattern from an adjacent position on the abluminal surface. In some embodiments the rivet 27 may be a solid body (FIG. 8A-8B) or a hollow body, e.g., the shank is a hollow tube and the opening extends through the head 28 of the rivet.

In some embodiments a rivet is a hollow or solid cylindrical tube and devoid of a pre-made head 28. In these embodiments the tube (solid or hollow) may be first fit within the hole then a pinch tool used to form the head and tail portions of the rivet. According to a preferred embodiment there is a process for making radiopaque markers as rivets, mounting the rivets on a scaffold and a scaffold having such markers mounted thereon. A process for making rivet-shaped markers from beads is described first.

As discussed above head and tail portions of the marker help to hold the marker in place, such as when an external force is applied to the rivet or the link structure is deformed during crimping or balloon expansion, or the scaffold makes a sharp turn in vasculature. In some embodiments however a tail portion, e.g., tail 27*b*' of the rivet 27' in FIG. 9, is not present. Instead, the rivet's shank portion is deformed to be trapezoidal or frustoconical in shape or to have enlarged end (e.g., rivet 137' shown in FIG. 15A). This type of marker has been found to produce increased resistance to be being pushed out of the hole of a strut or link when the scaffold is subjected to external forces that deform the link or strut holding the marker.

It is desirable to choose the appropriate size of the bead for forming the rivet. According to some embodiments the bead size, or bead volume to use depends on the strut thickness (t), hole diameter (D2), distance between holes (D1) and rim thickness (D2) of the scaffold structure where the rivet will be mounted (e.g., the link struts having holes 22 in FIG. 2A or 2B). The stock material may be spherical, or cylindrical. Stock made from a radiopaque material can be obtained from commercially available sources.

According to the disclosure, stock beads are used to make rivet markers for mounting in scaffold holes 22. In preferred embodiments rivet markers are mounted or engaged with scaffold holes of thin-walled struts or links having a thickness (t) that are preferably less than about 100 microns. The steps of a rivet-making process and attachment to a scaffold may be summarized as a six-step process.

STEP 1: select from the stock material a marker bead having a diameter or volume within the desired range, i.e., a diameter or volume suitable for mounting on a scaffold according to the dimensions D0, D1, D2 and t (FIG. 2B). Selection of the marker bead having the desired diameter or volume, or removal of a bead too small from the lot, may be accomplished using a mesh screen. The lot of beads is sifted over a mesh screen. Beads that do not have the minimum diameter or volume will fall through openings in the mesh screen. Alternative methods known in the art may also be used to remove unwanted beads or select the right size bead.

STEP 2: deposit the bead selected from Step 1 on a die plate.

STEP 3: cold form the rivet from the bead by pressing the bead into the die plate. At temperatures close to ambient temperature force the bead through the die (e.g., using a plate, mandrel head, pin or tapered ram head) to thereby re-shape the bead into a rivet defined by the die shape and volume of the bead relative to the volume of the die receiving the bead.

STEP 4: remove the formed rivets from the die plate. The formed rivets, which can have a total length of about 190-195 microns and diameter of about 300-305 microns, are removed using a tool having a vacuum tube. The air pressure is adjusted to grip a rivet at, or release it from the tip. The rivet is removed from the die by placing the opening of the vacuum tube over the head of the rivet, reducing the air pressure within the tube to cause the head to adhere to, or become sucked into the tube tip (due to the difference in pressure) and lifting the rivet from the die.

STEP 5: while the rivet remains attached to the tip of the tube, move the rivet to a position above the hole of the scaffold, place the rivet into the hole using the same tool, then increase the air pressure within the tool to ambient air pressure. The rivet is released from the tool.

Figure 14A:
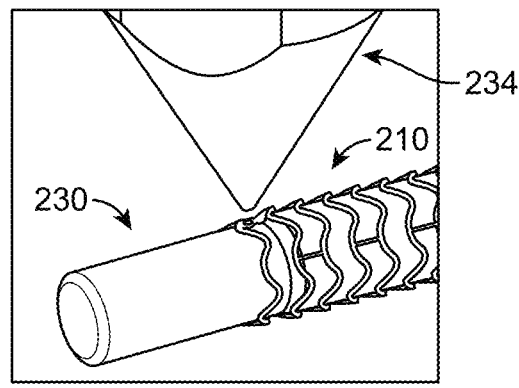
FIGS. 14A, 14B and 14C are perspective views depicting aspects of a process for deforming a rivet lodged in a scaffold hole to enhance engagement with the hole to resist dislodgment forces associated with crimping or balloon expansion.
Figure 14B:
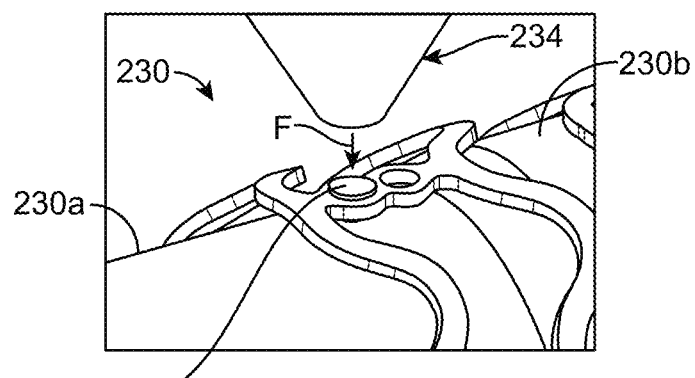
Figure 14C:
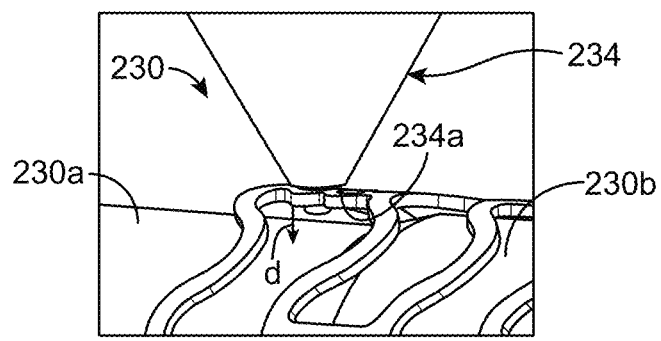

STEP 6: deform the rivet and/or hole to enhance the engagement or resistance to dislodgment of the marker from the hole, e.g., FIGS. 14A-14C.

It will be appreciated that according to STEPS 1-6 there is overcome the problem with the handling of non-spherical beads. For instance, the steps 1-6 above, wherein the rivet need not be re-orientated after being formed from a spherical bead, overcomes the problem of orientated spherical beads so that they can be aligned and placed into holes.

Figure 16A:
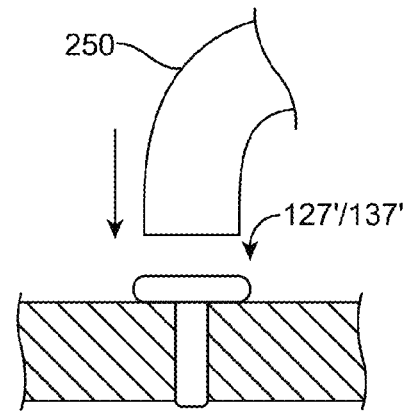
FIGS. 16A through 16C illustrate steps associated with removing a formed rivet marker from a die and placing the rivet marker into the hole of the scaffold.
Figure 16B:
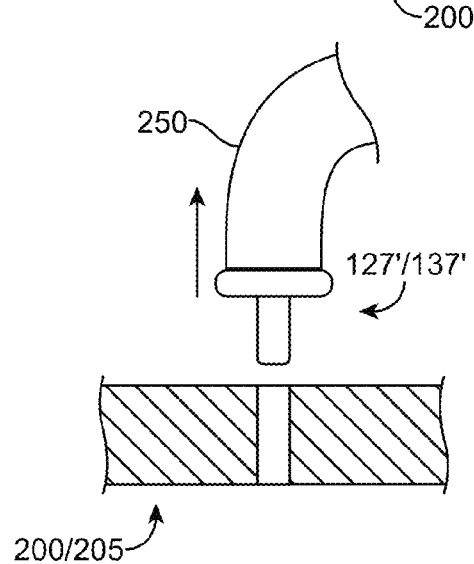
Figure 16C:
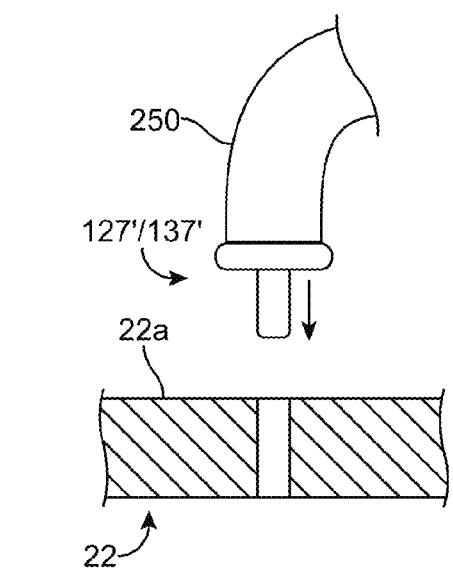

Referring to FIGS. 16A, 16B and 16C there is shown steps associated with transferring a formed rivet 127' (or 137') from a die 200 (or 205) to the scaffold strut hole 22 using a vacuum tool 350. As can be appreciated, the formed radiopaque marker 127' is extremely small, i.e., less than 1 millimeter in its largest dimension, as such the handling and orientation of the marker 127' for placement into the hole 22 is complicated (in contrast to placement of a sphere into the hole) because of the need to orient the shank properly with respect to the hole. For this reason the swaging or forging process is combined with placing into the scaffold hole, by removing the rivet 127' from the hole 200 with the tool 250, FIG. 16A, maintaining the orientation by keeping the rivet 127' attached to the tool, FIGS. 16B-16C, and then placing the rivet 127' into the hole 22a, FIG. 16C.

Figure 10:
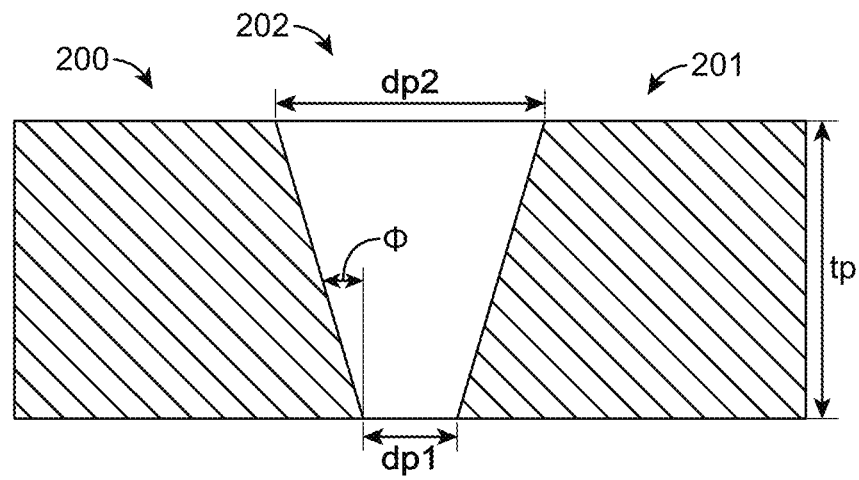
FIG. 10 is a side-cross section of a first die for forming a rivet marker from a radiopaque bead.
Figure 11A:
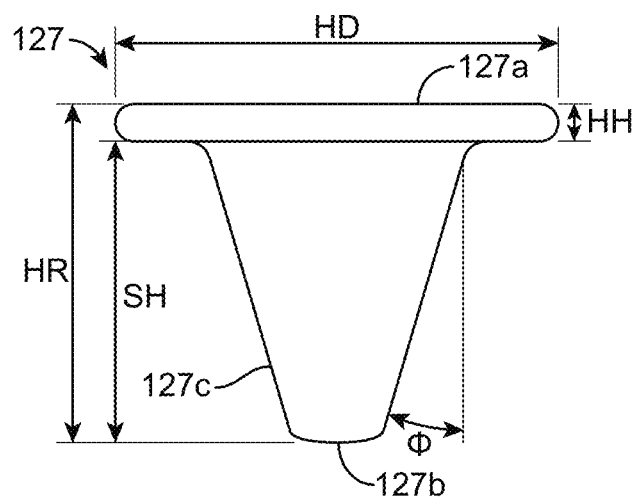
FIG. 11A is a side view of a rivet marker formed using the die of FIG. 10.

With reference to FIGS. 10 and 11A there is shown a first embodiment of a die 200 and marker 127 formed using the die 200, respectively, according to the disclosure. The die is a flat plate having a top surface 201 and a through hole extending from an upper end 201 to a lower end. The hole has an upper end diameter dp2 and lower end diameter dp1 less than dp2. The hole 202 is preferably circular throughout, although in other embodiments the hole may be rectangular or hexagonal over the thickness tp, in which case dp1 and dp2 are lengths or extents across the hole (as opposed to diameters). And the plate 200 has a height tp. The taper angle is related to dp2 and dp1 by the expression $\tan \phi = (\frac{1}{2}(dp2-dp1)/tp)$, which in a preferred embodiment $\phi$ is 1 to 5 degrees, 5-10 degrees, 3-5, or 2-4 degrees. The shape of die 200 produces a frustoconical shank, as depicted in FIG. 18A. A stock bead (not shown) is placed on the upper end of the opening 202 so that the bead sits partially within the hole 202. A flat plate, mandrel or pin ("ram head") is then pressed into the top of the bead so that the bead is forced into the hole 202. The bead is forced into the hole until the ram head is about distance HH from the surface 201. The rivet 127 formed from the foregoing forming process has the taper angle $\phi$ over all of, or a substantial portion of the shank height SH and the shank shape is frustoconical. The overall rivet height is HR, the head thickness is HH and the head diameter is HD. In some embodiments the angle $\phi$ may be sufficiently small so that the shank may be treated as a cylinder, or $\phi$ is about zero.

Figure 12:
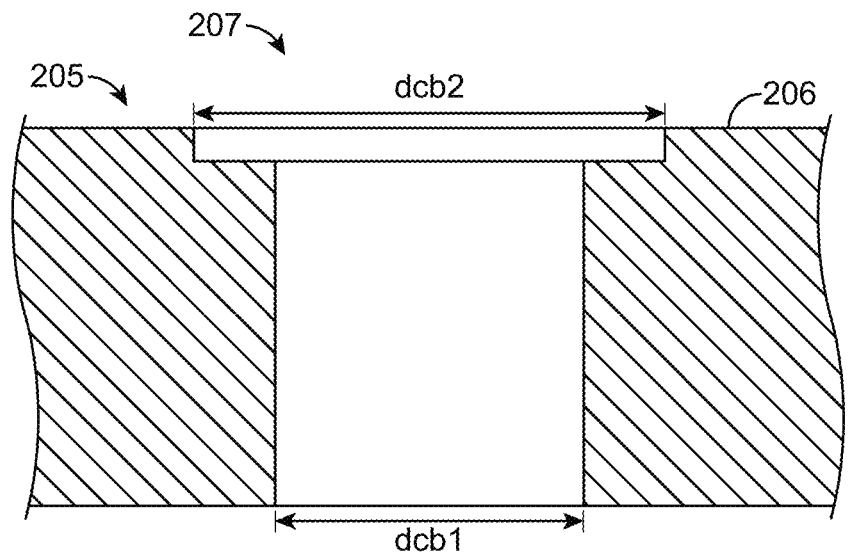
FIG. 12 is a side-cross section of a second die for forming a rivet marker from a radiopaque bead.
Figure 13:
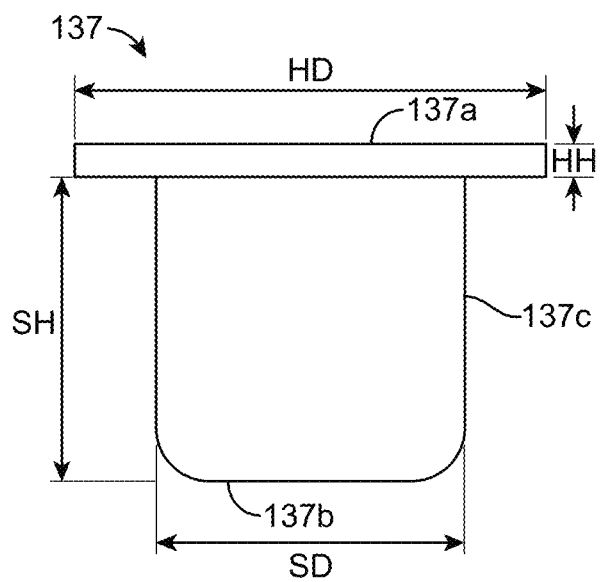
FIG. 13 is a side view of a rivet marker formed using the die of FIG. 12.

With reference to FIGS. 12 and 13A there is shown a second embodiment of a die 205 and marker 137 formed using the die 205, respectively, according to the disclosure. The die is a flat plate having a top surface 206 and a hole extending from an upper end 301 to a lower end. The hole has a constant diameter dcb1 throughout. A counter bore is formed on the upper end 206. The counter bore diameter is dcb2. The hole 207 is preferably circular throughout, although in other embodiments the hole 207 may be rectangular or hexagonal, in which case dcb1 is a length or extent across the hole (as opposed to a diameter). The shape of die 200 produces a rivet having a stepped cylindrical shape or cylindrical shank with a head, as depicted in FIG. 13A. A stock bead (not shown) is placed on the upper end of the opening 207 so that the bead sits partially within the hole 207. A ram head is then pressed into the top of the bead so that the bead is forced into the hole 207. The bead is forced into the hole until the ram head is about distance HH from the surface 206. The rivet 137 formed from the foregoing forming process takes the shape shown in FIG. 13A. The overall rivet height is SH+HH, the head thickness is HH, the shank height is SH and the head diameter is HD.

TABLES 3 and 4, below, provide examples of rivet dimensions for a rivet intended for being secured within a link hole 22 such as shown in FIG. 2A. In this example the thickness of the link is 100 microns and the values in microns (μm) for D0, D1 and D2 are 241, 64 and 64, respectively.

Values for the die 200 dimensions tp, dp2 and dp1 are 178, 229 and 183. The resulting formed rivet dimensions using die 200 are shown in TABLE 3. As can be appreciated from the results, the shank length (or height) is more than 150% of the link thickness and the rivet head diameter (HD) is significantly larger than the hole 22 diameter. The lower portion of the shank is relied on to form a tail portion of the rivet. The mean and standard deviation for HD, SD, and SL are based on the respective "n" samples of rivets measured.

TABLE 3

Rivet formation using tapered plate (FIG. 18A)

|  |  | inches | microns | n |
| --- | --- | --- | --- | --- |
| Rivet head diameter (HD) | mean | 0.0123 | 312 | 51 |
| from taper plate | standard deviation | 0.0015 | 38 |  |
| O.D. Rivet head diameter | mean | 0.0132 | 335 | 27 |
| post swage | standard deviation | 0.0011 | 28 |  |
| Shank Diameter (SD) | mean | 0.0089 | 226 | 51 |
|  | standard deviation | 0.0004 | 10 |  |
| Shank Length (SL) | mean | 0.0072 | 183 | 37 |
|  | standard deviation | 0.0009 | 23 |  |

Values for the die 300 dimensions dcb2 and dcb1 are 305 and 203. The resulting formed rivet dimensions using die 300 are shown in TABLE 3. The mean and standard deviation for HD, SD, HH and SL are based on the respective "n" samples of rivets measured.

TABLE 4

Rivet formation using counter bore plate (FIG. 13A)

|  |  | inches | microns | n |
| --- | --- | --- | --- | --- |
| Rivet head diameter (HD) | mean | 0.012 | 305 | 19 |
| from Die | standard deviation | 0.0003 | 10 |  |
| O.D. Rivet head diameter | mean | 0.013 | 330 | 30 |
| post swage | standard deviation | 0.0007 | 18 |  |
| Rivet head height (HH) | mean | 0.001 | 25 | 31 |
| Shank Diameter (SD) | standard deviation | 0.008 | 203 | 31 |
| Shank Length (SL) | mean | 0.0075 | 190 | 24 |
|  | standard deviation | 0.0008 | 20 |  |

In TABLES 3 and 4 "O.D. Rivet head diameter post-swage" refers to the outer diameter of the rivet marker head after the rivet marker is pressed into the scaffold hole.

Discussed now are examples of processes for mounting either of the rivets 127, 137 to the scaffold hole 22. According to some embodiments the rivet shank is placed into the hole 22 from the abluminal or outer side of the scaffold, so that the head sits on the abluminal surface 22*a*. The rivet may instead be placed from the luminal side of the hole. The rivet is firmly pressed into the hole so that a maximum portion of the shank extends from the luminal or abluminal sides, respectively.

Figure 11B:
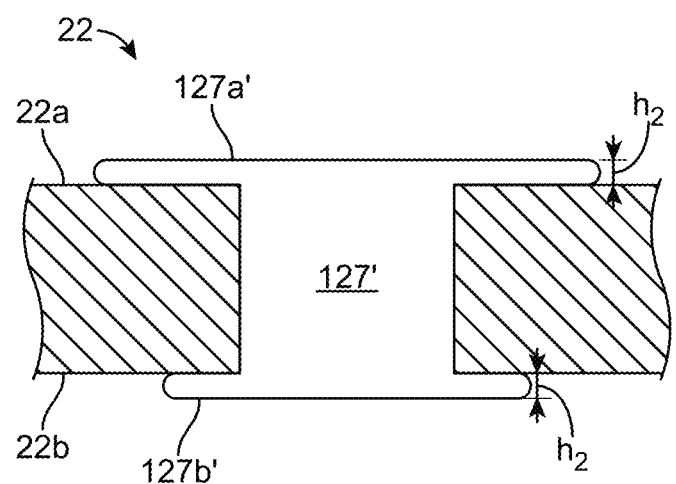
FIG. 11B is a side cross-section of a scaffold strut with the marker of FIG. 11A engaged with a hole of the strut and after a forming process deforms the marker to make upper and lower rims retaining the marker in the hole.

For the rivet 127 after it is placed in the hole 22 the side opposite the head is subjected to a swaging process. With reference to FIG. 11B there is shown in cross-section the deformed rivet 127' in the hole 22. The rivet 127' has a head 127*a*' that extends from the surface 22*a* by an amount h2. The length h2 may be about 25 microns, between 25 and 50 microns or between 5 and 50 microns. The same dimensions apply to a tail 127*b*' that extends from the opposite surface of the link (e.g., luminal surface). The diameter of the head 127*a*' can be larger than the tail, or the tail 127*b*' diameter can be larger than the head 127*a*' diameter. The tail portion is formed from the extended shank length that protrudes from the link surface by swaging. The tail 127*b*' is formed by swaging. For example, the rivet 127 is placed in from surface 22*a* (abluminal side) so that a significant portion of the shank length, e.g., 50% of the strut thickness, extends from the luminal side. A cylindrical mandrel (not shown) is placed through the scaffold's bore. This mandrel has an outer diameter slightly less than an inner diameter of the scaffold and provides a swaging surface to form the tail 127*b*'. The mandrel is rolled back and forth over shank portion extending form the luminal surface. This motion causes the shank material to flatten out around the hole, thereby producing the tail portion 127*b*'. The resulting rivet 127' is secured in place, at least in part, by the tail portion 127*b*' resisting forces tending to push the rivet towards the abluminal side of the hole and the head portion 127*a*' resisting forces tending to push the rivet towards the luminal side of the hole 22. As shown, the deformation of the shank produces the tail 127*b*' having a flange disposed on the surface 22*b*. The flange may be circular like the head and may have a flange radial length greater or less than the radial length of the flange of the head 127*a*'.

Figure 15A:
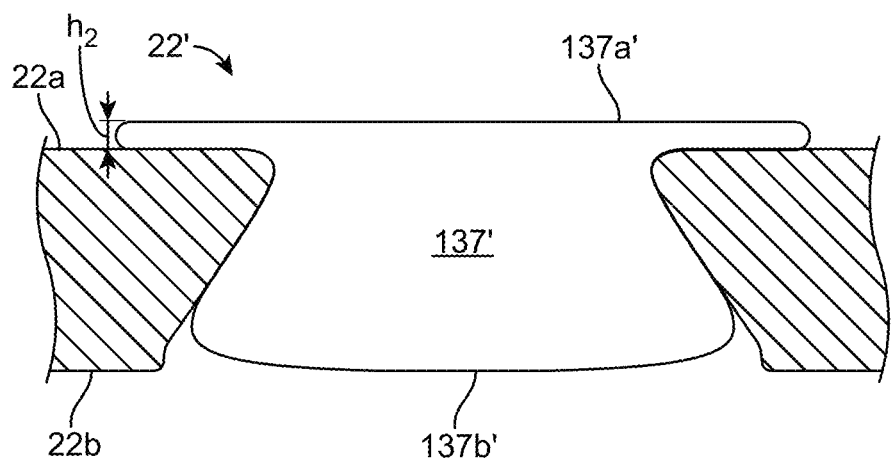
FIG. 15A is a side cross-sectional view of a deformed rivet marker and scaffold hole following the process described in connection with FIGS. 14A-14C.
Figure 15B:
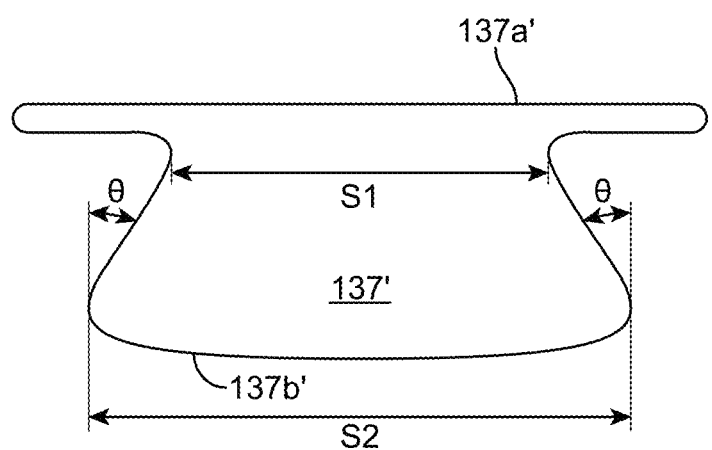
FIG. 15B is a view of the deformed marker illustrated in FIG. 15A.

With reference to FIGS. 15A and 15B, a stepped mandrel is used in conjunction with a ram head to produce the rivet 137' from rivet 137. The rivet has a shank 137' that is reformed from, e.g., a generally-cylindrical shape when using the die 205, FIG. 12, to the shape shown in FIGS. 15A through 15C. This shank shape may be characterized by a taper angle θ of magnitude of from between about 5 and 15 degrees, 5 to 9 degrees, or about 3 to 8 degrees. The shank according to some embodiments of a rivet in the hole 22 is frustoconical in shape, wherein the shank end opposite, or distal of the head 137*a*', or end 137*b*' is larger or has a larger diameter than the shank portion proximal or nearest the head 137*a*'. The deformed shank 22' may have a shank diameter S2 nearest one of the abluminal and luminal side openings of the hole 22' that is larger than the shank diameter S1 nearest the other of the luminal and abluminal side opening, or S2>S1. According to some embodiments, as shown in FIG. 15A the cylindrical hole 22 is also deformed into the hole 22' that has an opening at surface 22*b* larger than the hole opening at surface 22*a*. According to some embodiments both the hole 22 and rivet 137 are deformed when the rivet 137 is mounted on the scaffold.

The structure illustrated in FIG. 15A may be made by a second process of attaching a rivet marker to a scaffold hole 22. In contrast to the first process a tool is not rolled across the surface where the shank tail portion protrudes from the hole opening. Instead, the shank tail end is pushed directly into a non-compliant surface, which can be a surface of a metal mandrel. The rivet is forced to deform by a compression force between the surface of the mandrel and head of a ram 234, which pushes the rivet into the mandrel surface. The first process producing the deformed rivet 127' by contrast is formed by a combination of rolling a hard surface into the shank and a restraint on the head 127*a*, which holds the rivet head against the surface 22*a* while the tail end 127*b* is being swaged. Under the second process the force line of action is completely along the axis of the rivet, or perpendicular to the rivet head. The result is a flattened or widened shank portion and deformed hole with little or no flange or rim formed from the tail portion of the shank.

The second process is now described in further detail with reference to FIGS. 14A-14C. The scaffold 400 is placed over a stepped mandrel 230. This mandrel has a first outer diameter and a second outer diameter, which is less than the first outer diameter. The scaffold portion holding the marker 137 is placed over the lower diameter portion of the mandrel 230. The larger diameter portion of the mandrel 230 holds the adjacent parts of the scaffold. The lower diameter part of the mandrel 230 has a surface 230*a* and the larger diameter portion has a surface 230*b*. As shown in FIGS. 14B, 14C the ram 234 pushes with a force F (FIG. 14B) the scaffold portion holding marker 137 into the mandrel surface 230*a*, which causes this scaffold end to deflect a distance "d" towards the surface 230*a* (FIG. 14A). After the scaffold reaches the surface 230*a*, the ram 234 continues to push into the scaffold portion holding the marker (by pressing directly against the head 137*a*) to create the deformed marker 137' and hole 22' as shown in FIG. 15A. The surface 230*a* chosen may be smooth or free of grooves, pitting, depressions or other surface irregularities (other than a surface of a cylinder) that would inhibit flow of material during swaging. In a preferred embodiment the mandrel surface is smooth compared to the surface of the head 234 pressed into the rivet marker 137. That is, the coefficient of friction (Mu) between the head 234 and surface 137*a*' is greater than Mu between surface 230*a* of mandrel 230 and surface 137*b*'.

The shape of the deformed shank 137' and hole 22' shown in FIG. 15*b* produced higher push-out forces than previously believed (a "push-out force" means the force needed to dislodge the marker from the hole). Indeed, unexpectedly it was discovered that the deformed rivet 137' and hole 22' had a higher resistance to dislodgement than a marker fit into a link having an over 50% higher thickness, irrespective of the presence of the head 137*a*'. For example, tests for a minimum dislodgment force needed to push the rivet 137' out from the side 22*a* of the hole 22' of a strut having a 100 micron thickness were higher than the dislodgment force needed to push out a marker mounted according to US20070156230 (FIG. 8A, 8B or where the sphere is deformed more into a cylinder when in the depot, thus increasing the surface-to-surface contact to a maximum) and for a hole of a strut having an about 50%-higher thickness (158 microns vs. 100 microns). As TABLE 4 demonstrates:

TABLE 4

| Scaffold (TABLE 1) | Marker process | Bead volume ($\mu m^3 \times 10^6$) | US20070156230 (FIGS. 8A, 8B) | Interior hole surface area (thickness × diameter × π) ($\mu m^2 \times 10^3$) | Push-out force (gram-force) from luminal to abluminal side of link |
|---|---|---|---|---|---|
| A | Press sphere into hole (US20070156230, FIGS. 8A, 8B) | 6.76 | wall thickness 158 µm and hole diameter 234 µm | 116.2 | 51.5 (n = 8) |
| B | FIGS. 14A-14C and using rivet marker 137 | 6.76 | wall thickness 100 µm and hole diameter 241 µm | 75.7 | 78.6 (n = 31) |

There are higher push-out forces for scaffold B, even though scaffold A has more surface area for contact with the marker, thus higher frictional forces resisting dislodgment. This result indicates that the deformation that occurs during the swaging process resulting in the deformed rivet marker and hole of FIG. 15A has a significant effect on the push-out force (note: the gram-force push-out force reported in TABLE 4 was applied to the luminal side 22b for scaffold B). Given the more than 50% higher wall thickness Scaffold A should have had a higher dislodgment force (the same bead material, bead volume and poly(L-lactide) scaffold material for Scaffold A and B). The higher dislodgment force can be explained by the shape of the deformed shank and hole, which essentially produces a lower portion 137b' that is significantly larger than the opening 22a of the strut 22. Thus, the dislodgment force must be high enough to deform the opening 22a' and/or shank portion 137b' in order to dislodge the marker from the 22a side of hole 22' (as opposed to only needing to overcome essentially a frictional force between the material and walls of the hole).

The shape 137' in FIG. 15B may be formed by a swaging process that deforms the rivet while it sits inside the hole 22. The rivet may have the shape and/or characteristics of rivet 27, 127 or 137 before swaging. The flow of rivet material transversely (shear flow) during swaging near tail portion 137b' causes it to expand out and also yield (enlarge) the strut hole nearer to opening 22b'. This produces the trapezoidal-like or frustoconical shape of the rivet shank and hole. The swaging process of FIGS. 14A-14C applies equal and opposite forces that are about co-linear with the axis of symmetry of the rivet (as opposed to a rolling motion on one side). If instead a cylinder or sphere (as opposed to a rivet) were placed in the hole 22 and about the same coefficient of friction (COF) existed between the swaging surface 230a and tail 137b as the COF between the swaging surface 234 and the head 137a, but otherwise the same swaging process as in FIGS. 14A-14C, it is believed that the result would be a more symmetric deformed marker, e.g., a squashed cylinder or barrel-shaped marker depending on the COF, such as the shape shown in US20070156230. This result can be appreciated from Kajtoch, *J Strain in the Upsetting Process*, Metallurgy and Foundry Engineering, Vol. 33, 2007, No. 1 (discussing influence of coefficient of friction between ram and ingot on resulting shapes for slenderness ratios greater than 2). The shape of the radiopaque material forced into the hole is also a factor, e.g., a rivet 137 verses a sphere (scaffold A). The presence of the head on one side results in a shank forming an asymmetric shape about the strut mid-plane axis. It is believed that a combination of the rivet shape and coefficient of friction differences produced the favorable result.

In a preferred embodiment a smooth mandrel 230 surface 230a presses against the surface 137b, as compared to a more rough surface of the head 234 that presses against the surface 137a. In a preferred embodiment the coefficient of friction for the abluminal side was greater than 0.17 or Mu>0.17, whereas the coefficient of friction on the luminal side was less than 0.17 or Mu<0.17. As discussed above, the effect of a difference in the coefficient of friction can be explained by the restraint on shear or later material flow near the end abutting the respective swaging head. If the coefficient of friction is sufficiently low then the surface area expands out laterally, as opposed to being held relatively constant. Thus, since Mu is less on the luminal side there is more lateral flow than on the abluminal side. The result, when combined with use the rivet shape, is believed to be the frustoconical shape as disclosed, e.g., as shown in FIGS. 15A-15B, which may be thought of as a shank having a locking angle θ.

There may be a heating step for a scaffold following marker placement. In some embodiments this heating step may correspond to a rejuvenation step of the scaffold polymer, prior to crimping, to remove aging effects of the polymer.

Thermal rejuvenation (including thermal treatment of a bioresorbable scaffold above TG, but below melting temperature (Tm) of the polymer scaffold) prior to a crimping process may reverse or remove the physical ageing of a polymeric scaffold, which may reduce crimping damage (e.g., at the crests of a scaffold) and/or instances of dislodgment of a marker.

According to some embodiments a scaffold is thermally treated, mechanically strained, or solvent treated to induce a rejuvenation or erasure of ageing in a polymer shortly before crimping the scaffold to a balloon and after marker placement. Rejuvenation erases or reverses changes in physical properties caused by physical ageing by returning the polymer to a less aged or even an un-aged state. Physical ageing causes the polymer to move toward a thermodynamic equilibrium state, while rejuvenation moves the material away from thermodynamic equilibrium. Therefore, rejuvenation may modify properties of a polymer in a direction opposite to that caused by physical ageing. For example, rejuvenation may decrease density (increase specific volume) of the polymer, increase elongation at break of the polymer, decrease modulus of the polymer, increase enthalpy, or any combination thereof.

According to some embodiments, rejuvenation is desired for reversal or erasure of physical ageing of a polymer that was previously processed. Rejuvenation is not however intended to remove, reverse, or erase memory of previous processing steps. Therefore, rejuvenation also does not educate or impart memory to a scaffold or tube. Memory may refer to transient polymer chain structure and transient polymer properties provided by previous processing steps. This includes processing steps that radially strengthen a tube from which a scaffold is formed by inducing a biaxial orientation of polymer chains in the tube as described herein.

In reference to a marker—scaffold integrity or resistance to dislodgment during crimping, it has been found that a heating step can help reduce instances where crimping causes dislodgment of a marker. According to some embodiments, any of the foregoing embodiments for a marker held within the scaffold hole 22 can include, after the marker has been placed in the hole, a heating step shortly before crimping, e.g., within 24 hours of crimping. It has been found that the scaffold is better able to retain the marker in the hole 22 following heating. A mechanical strain, e.g. a limited radial expansion, or thermal rejuvenation (raise the scaffold temperature above the glass transition temperature (TG) of the load-bearing portion of the scaffold polymer for a brief time period) can have a beneficial effect on scaffold structural integrity following crimping and/or after balloon expansion from a crimped state.

In particular, these strain-inducing processes tend to beneficially affect the hole 22 dimensions surrounding the marker when the hole is deformed in the manner discussed earlier in connection with FIGS. 15A-15B.

According to some embodiments the scaffold after marker placement is heated to about 20 degrees, or 30 degrees above the glass transition temperature of the polymer for a period of between 10-20 minutes; more preferably the scaffold load bearing structure (e.g., the portion made from a polymer tube or sheet of material) is a polymer comprising poly(L-lactide) and its temperature is raised to between about 80 and 85 Deg. C for 10-20 minutes following marker placement.

Figure 15C:
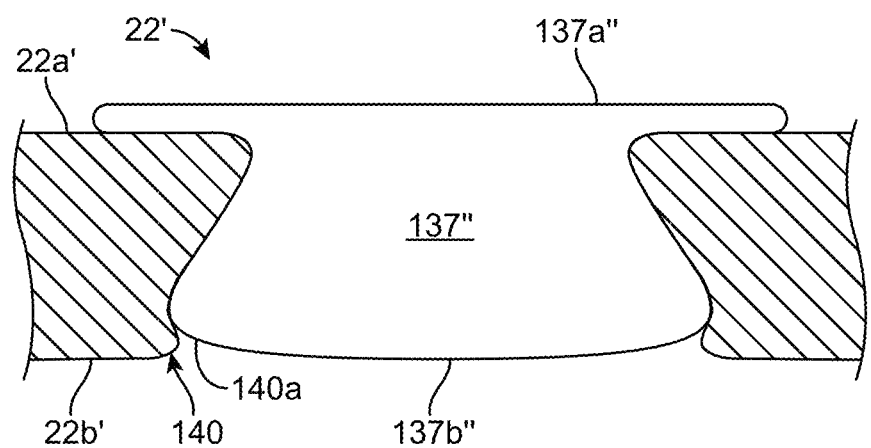
FIG. 15C is a side cross-sectional view of the rivet and marker hole of FIG. 15A following a heating step.

According to some embodiments it has been found that raising the temperature of the scaffold after marker placement re-shaped portions of the hole 22 to improve the fit of the marker in the hole. With reference to FIG. 15C after the rivet marker 137 is placed in the hole 22 according to the second process the hole shape deforms to produce a lip or edge 140 at the end 137b", which may produce a higher resistance to dislodgment than for a scaffold-marker structure not subsequently treated by a rejuvenation step. The surface 140a of the lip 140 interferes more with dislodgment of the marker when a force is directed towards the end 22b'.

In accordance with the foregoing objectives of achieving a desired crimp profile for a thin-walled scaffold there is a method for crimping such a scaffold to a balloon that meets the following needs:
  Structural integrity: avoiding damage to the scaffold's structural integrity when the scaffold is crimped to the balloon, or expanded by the balloon.
  Safe delivery to an implant site: avoiding dislodgement or separation of the scaffold from the balloon during transit to an implant site.
  Uniformity of expansion: avoiding non-uniform expansion of scaffold rings, which can lead to structural failure and/or reduced fatigue life.

As previously reported in US20140096357 a scaffold is not as resilient as a stent made from metal, which is highly ductile. The needs therefore for satisfying all of the above needs are especially for a thin-walled scaffold that can fracture more easily during crimping or balloon expansion.

Figure 17A:
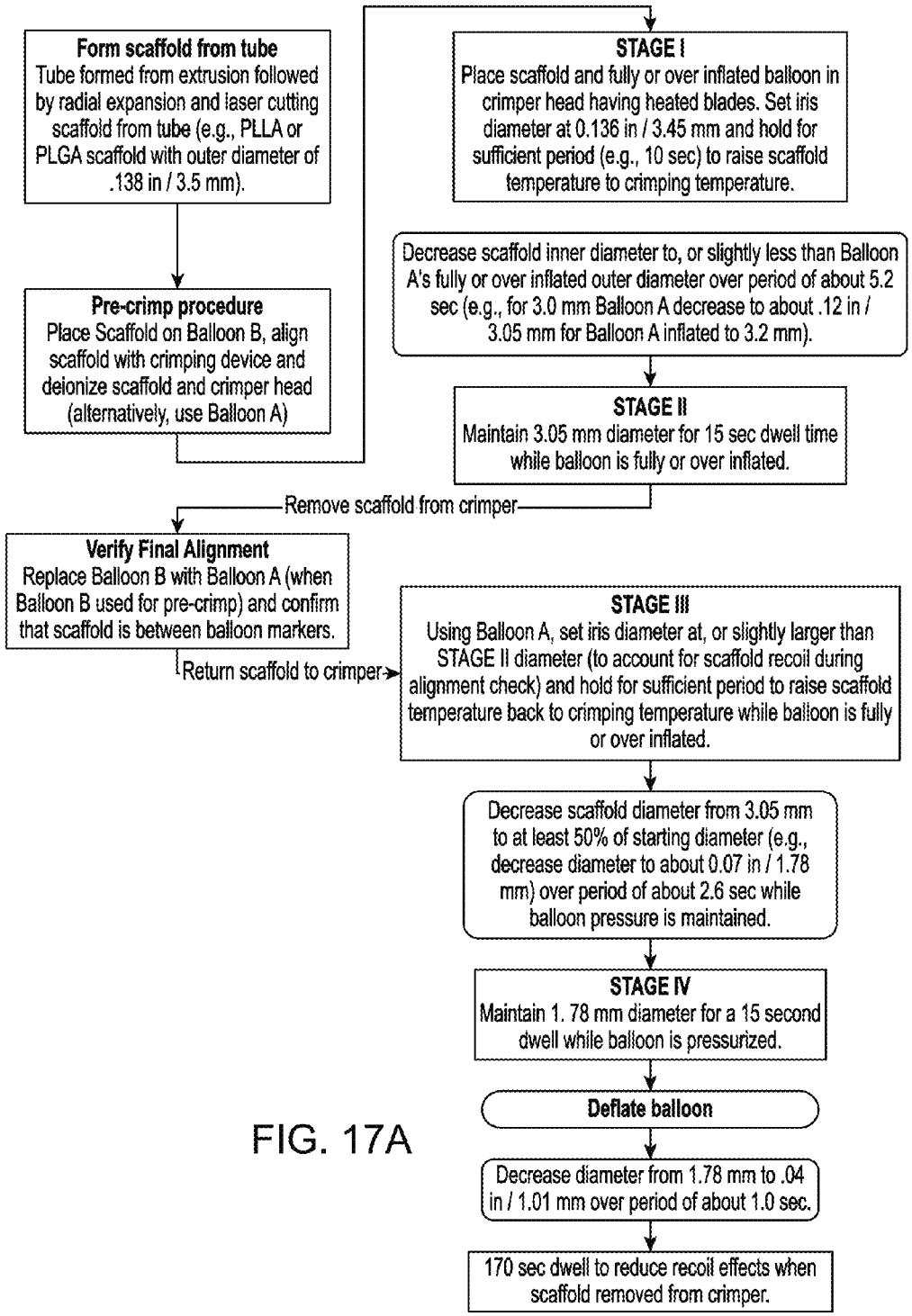
FIGS. 17A and 17B describe a process for crimping a thin-walled scaffold according to the disclosure.
Figure 17B:
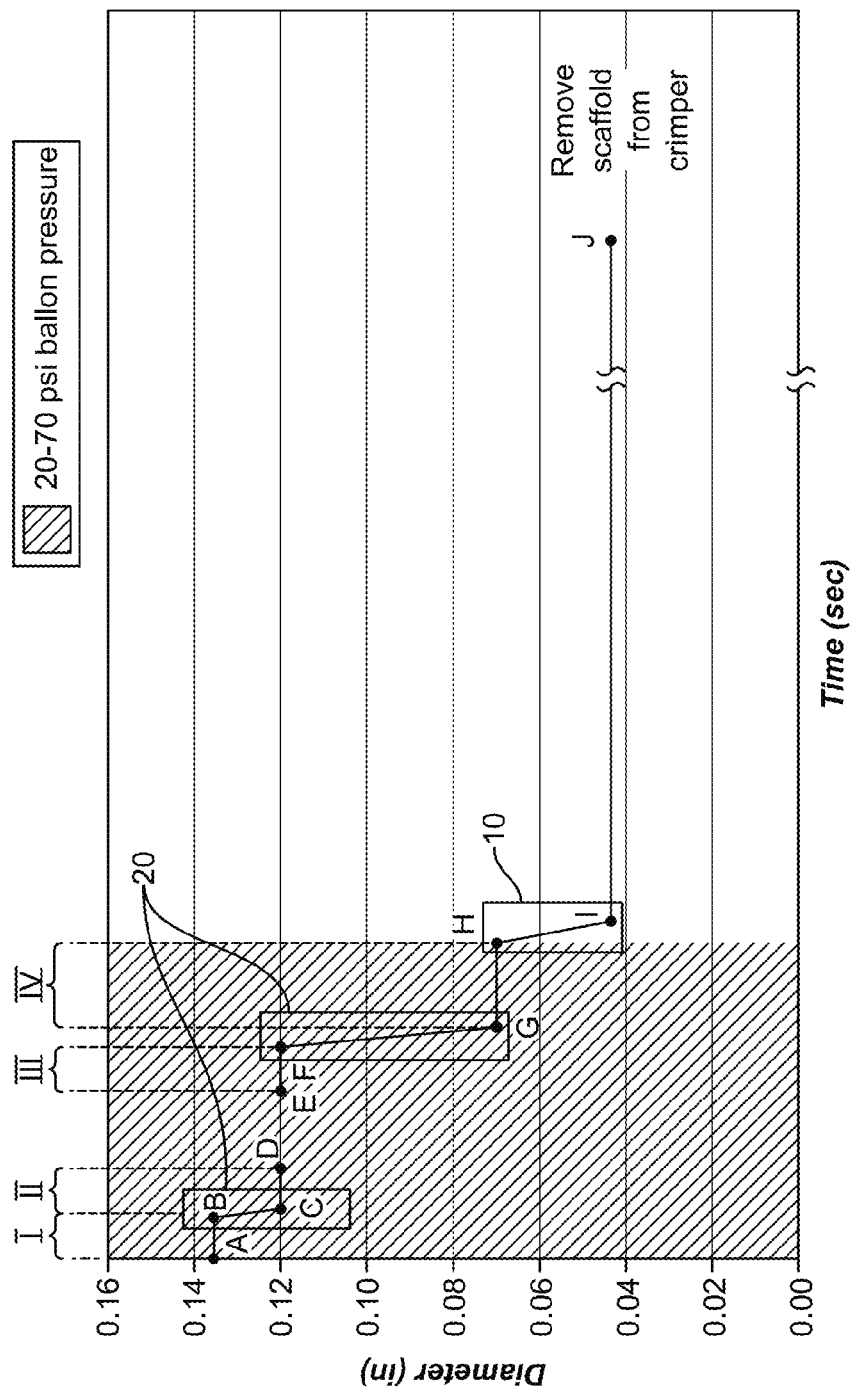

FIGS. 17A-17B illustrate steps associated with a crimping process for crimping to a balloon catheter (FIG. 3D) for the thin-walled scaffolds 300, 400, 500, 600 or 700 according to the disclosure. It has been found that this crimping process can satisfy all the above needs for a scaffold crimped to D-min. In this example there is a crimping process described for crimping a 3.5 mm scaffold to a 3.0 mm semi-compliant PEBAX balloon. FIG. 17B illustrates in graphical form the crimping portion of the FIG. 17A flow—a graph of scaffold diameter verses time with a balloon pressure of between about 20-70 psi (or 1 atm up to the fully or over-inflated balloon pressure) applied throughout substantially all of the crimping process. For example, the balloon pressure is maintained at 70 psi for steps A-G, then the pressure is allowed to decrease (or deflated) to 50 psi (or 1 atm) for the period G-H. Balloon pressure is removed at point H. No balloon pressure is used for steps H-J for purposes of achieving a low crossing profile or crimping to D-min and avoiding damage to the balloon.

FIG. 17A indicates three possibilities for crimping, depending on need. First, there are two balloons used: Balloon A and Balloon B. balloon B is used for the pre-crimp step(s) and Balloon A (used with the delivery system) is used for the final crimp. Second, there is only one balloon used (Balloon A) for the entire crimp process including the verify alignment check. In this case, the scaffold inner diameter is larger than the fully or overinflated Balloon A. As such, during pre-crimp there may be shifting on the balloon. Third, there is only one balloon used (Balloon A) for the entire crimp process without a verify final alignment check. In this case, the balloon for the delivery system has a fully or overinflated state that is about equal to the inner diameter of the scaffold inner diameter.

Stage I: The scaffold supported on the fully inflated balloon of the balloon-catheter is placed within the crimp head. The balloon when inflated and supporting the scaffold in this state has substantially all folds removed. In a preferred embodiment the catheter's balloon (i.e., the balloon used in the final product—a stent delivery system) is used for Stage I through Stage II. In other embodiments it may be preferred to use a second, larger balloon for Stage I and II (as explained in more detail below). The blades of the crimper are heated to raise the scaffold temperature to a crimping temperature. In the preferred embodiments the crimping temperature is between a lower end of the glass transition temperature for the polymer (TG) and 15 degrees between TG.

After the scaffold reaches the crimping temperature, the iris of the crimper closes to reduce the scaffold inner diameter (ID) to slightly less than the outer diameter (OD) of the fully or over inflated balloon (e.g., from 3.45 mm to about 3.05 mm for the PEBAX 3.0 mm semi compliant balloon inflated to a diameter of about 3.2 mm). In this example, Balloon B would be used for the diameter reduction down to the 3.0 mm balloon size, or the Balloon A size (e.g., the 3.0 mm balloon).

Stage II: The crimper jaws are held at the 3.05 mm diameter and maintained at this diameter for a second dwell period at the crimping temperature. After Stage II the scaffold has about 90% of its pre-crimp diameter.

The foregoing Steps I-II reduce the scaffold diameter down to the size of the fully inflated balloon of the stent delivery system (i.e., Balloon A). Since at the time of the initial alignment check (before any crimping) the scaffold inner diameter was larger than the balloon fully inflated diameter (e.g. the scaffold diameter is about 109%-116% of the fully inflated balloon diameter for a balloon with diameters of 3.0 mm to 3.2 mm, respectively) there is a possibility that the scaffold shifts longitudinally (relative to the balloon) while being crimped down to the balloon size. Given this possibility, the scaffold is removed from the crimper and its alignment on the balloon is checked relative to proximal and distal balloon markers.

"Verify final alignment" step: When the scaffold requires adjustment on the balloon, a technician makes manual adjustments to move the scaffold into position. It has been found difficult, however, to make these minor adjustments while the scaffold rests on the fully inflated balloon and has an inner diameter slightly less than the balloon's outer diameter. To address this need, the balloon pressure is slightly decreased, or the balloon temporarily deflated so that the re-alignment may be done more easily. When the scaffold is properly re-aligned between the balloon markers, the scaffold and fully inflated balloon are placed back into the crimper. With the scaffold inner diameter and balloon sizes now about equal the final crimping of the scaffold to the catheter's balloon can commence. To ensure no further longitudinal movement of the scaffold relative to the balloon, it is preferred to have the scaffold diameter be slightly less than the balloon fully inflated diameter prior to the start of Stage III. As noted above, where two balloons are used, Balloon B is replaced with Balloon A, alignment is done with respect to Balloon A and the scaffold is crimped down to the final diameter on Balloon B.

Stage III: The scaffold and balloon are returned to the crimper. The jaws are closed to a diameter about the same as, or slightly larger than in Stage II (to account for recoil occurring during the alignment check). The crimper jaws are held at this diameter for a third dwell time, which may be the time needed for the scaffold to return to the crimping temperature.

The iris diameter is then reduced to an ID corresponding to about, or slightly less than the OD for the balloon if the balloon were not pressurized and had randomly distributed folds. That is, the scaffold is crimped down to the approximate OD for the balloon if it were pressurized then deflated so that substantially all pre-made folds are replaced by random folds. For example, the iris diameter is reduced down to about 1.78 mm for the 3.5 mm scaffold. After this diameter reduction the scaffold OD is about 60% of its diameter at Stage III and about 50% of its starting, or pre-crimp OD.

Stage IV: After the scaffold OD is reduced to about 50% of its starting diameter, the crimper jaws are held at this diameter for a third dwell time. In a preferred embodiment balloon pressure is slightly decreased during this dwell. For example, for the 3.0 mm semi-compliant PEBAX balloon the pressure is decreased from 70 psi to 50 psi during the Stage IV dwell. This decrease is preferred to achieve a lower crossing profile and/or to protect balloon material from overstretch.

Following the Stage IV dwell period, the balloon is deflated or allowed to return to atmospheric pressure and the iris of the crimper is reduced down to a final crimp OD, e.g., 1.01 mm or about 30% of its pre-crimp OD. This balloon deflation may occur by opening the valve supplying the pressurized gas to the balloon while, or just before the iris diameter is reduced to the final crimp diameter.

The crimper jaws are then held at the final crimp diameter for about a 170 second dwell period, or between 100 and 200 seconds with the crimping temperature maintained (i.e., scaffold temperature being between 15 degrees below TG and about TG) or without the crimping temperature being maintained. This final dwell period is intended to reduce the amount of scaffold recoil when the crimped scaffold is removed from the crimper. Immediately following the 170 second dwell the scaffold is removed and a retaining sheath is placed over the scaffold to further aid in reducing recoil. A leak test may be done after the final stage crimping.

It may be necessary to provide auxiliary pressure sources for a balloon in order to maintain a relatively constant pressure throughout the diameter reduction and dwell periods (as illustrated in the above example). Indeed, in one embodiment it was found that during diameter reduction there was a pressure drop in the balloon. To address this pressure drop, a secondary pressure source was used to maintain the same pressure during diameter reductions as during dwell periods.

The foregoing example of a preferred crimping process, which selectively pressurizes the balloon throughout the crimping steps, is expected to provide three benefits while minimizing any possible overstretching of the balloon. The first benefit is increased scaffold-balloon retention. By maintaining relatively high pressure in the balloon through most of the crimping steps, more balloon material should become disposed between struts of the scaffold since balloon material is being pressed more into the scaffold, than the case when crimping is done without balloon pressurization, or only after the scaffold is substantially reduced in diameter. Additionally, it is expected that by substantially removing folds before any diameter reduction, the balloon material becomes more compliant. As such, more balloon material is able extend between struts, rather than being pressed between the scaffold and catheter shaft when the scaffold is being crimped.

The second benefit of balloon pressurization is more uniform expansion of the crimped scaffold when the balloon is expanded. When the balloon is inflated from the beginning, before any crimping takes place and when there is the greatest space available for the balloon to unfold within the mounted scaffold, balloon material become more uniformly disposed about the circumference of the catheter shaft after crimping. In a preferred embodiment the balloon is fully inflated and held at this inflated state for at least 10 seconds before any crimping to ensure all pre-made folds are removed. If the balloon is only partially expanded, as in the case where the balloon is inflated after the scaffold has been partially crimped (thereby leaving less space available for the balloon to fully unfold), fold lines or balloon memory not removed by balloon pressure, it is believed that the presence of folds or partial folds causes balloon material to shift or displace during crimping, thereby resulting in a more non-uniform distribution of balloon material about the circumference of the catheter shaft after crimping.

The third benefit is avoidance of out of plane twisting or overlapping scaffold struts, which can result in loss of strength, cracks or fracture in struts. As discussed earlier, support of the scaffold within crimper with an inflated balloon is believed to counteract or minimize any tendency for struts to move out of alignment.

The foregoing benefits may be achieved without risk that balloon material will be excessively stretched during the crimping process when balloon pressure is selectively controlled. Referring to FIG. 3B, the pressure range provided is 20-70 psi. The upper end of this pressure range forms the fully inflated balloon in the case of the balloon used in the example and may be maintained for the first three stages. Balloon pressure reduction to 50 and 20 psi for Stage IV follows. It was found through several tests that maintaining a constant, and consistent fully inflated balloon pressure up until the beginning of stage IV or after the crimped scaffold had reached about ½ of the original scaffold diameter, followed by a slight decrease in pressure, provided a good balance of stent retention, uniform expansion, low crossing profile, uniform crimping and avoidance of damage to balloon material.

As noted earlier, there are three possibilities for crimping: use two balloons—Balloon A and Balloon B. Balloon B is used for the pre-crimp step (a) and Balloon A (used with the delivery system) is used for the final crimp. Second, there is only one balloon used (Balloon A) for the entire crimp process including the verify alignment check. In this case, the scaffold inner diameter is larger than the fully or over-inflated Balloon A. As such, during pre-crimp there may be shifting on the balloon. Third, there is only one balloon used (Balloon A) for the entire crimp process without a verify final alignment check. In this case, the balloon for the delivery system has a sully or overinflated state that is about equal to the inner diameter of the scaffold inner diameter. These different embodiments are described further, below.

In some embodiments a process is described by the example in FIGS. 17A-17B and as described above, with the following exception. Two balloons are used—a sacrificial or secondary balloon (Balloon B) in addition to the catheter's balloon (Balloon A)—as opposed to only Balloon A as in the above example of a preferred embodiment. Balloon B is a balloon that has a larger nominally inflated balloon diameter than Balloon A, or is capable of being over inflated to a larger diameter than Balloon A. Balloon B is used for Stages I and II. Balloon B is selected to have a fully inflated diameter that is the same as, or slightly larger than the original inner diameter of the scaffold. One advantage of this alternative embodiment is that the scaffold is supported by a balloon throughout the crimping process (as opposed to the above example where Balloon A can provide little or no radial support for the scaffold since there is a gap at Stage I). After Stage II, the scaffold is removed from the crimper and Balloon B is replaced by Balloon A. Thereafter, the crimping process continues as described earlier.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in claims should not be construed to limit the invention to the specific embodiments disclosed in the specification.

What is claimed is:

1. A medical device, comprising:
a thin-walled scaffold having a network of rings interconnected by links, wherein each ring has a plurality of crests, wherein a crest is one of a U crown, Y crown and W crown, each ring extends circumferentially in an undulating fashion along a vertical axis (B-B) perpendicular to a longitudinal axis (A-A); and
a marker link extending between a first ring and a second ring of the network of rings, the marker link including a structure having a hole and a radiopaque material is contained within the hole;
wherein the marker link forms with the first ring a first ring W crown and with the second ring a second ring Y crown, wherein a ½ wave length of the first ring measured from the first ring W crown to an adjacent U crown of the first ring is greater than a ½ wave length of the second ring measured from the second ring Y crown to an adjacent U crown of the second ring; and
wherein a length of the marker link is greater than a length of a link connecting the second ring to a third ring adjoined with the second ring.

2. The medical device of claim 1, wherein the marker link includes a first link portion extending from the structure to the first ring W crown and a second link portion extending from the second ring Y crown to the structure, wherein a width of the first link portion is greater than a width of the second link portion.

3. The medical device of claim 2, wherein a length of the first length portion is less than a length of the second link portion.

4. The medical device of claim 1, wherein the structure includes a first hole and a second hole, each containing the radiopaque material, wherein the first and second holes are aligned parallel to the axis A-A.

5. The medical device of claim 1, wherein the first ring includes a first, second and third crest, the first crest corresponding to the first ring W crown, the second crest corresponding to a first ring U crown and the third crest corresponding to a first ring Y crown, the second crest is adjacent the first crest and the third crest is adjacent the second crest, wherein a second wavelength extending from the second crest to the third crest is less than a first wavelength extending from the first crest to the second crest.

6. The medical device of claim 1, wherein a flat portion of the first ring W crown is greater than a flat portion of a third ring W crown of a third ring adjoined with the second ring, and/or a flat portion of a fourth W crown of the first ring.

7. The medical device of claim 1, wherein a wavelength of the first ring forming the first ring W crown is longer than a wavelength of the second ring forming the second ring Y crown.

8. A medical device, comprising:
a thin-walled scaffold having proximal and distal end portions formed by a network of rings interconnected by links, wherein each ring of the network of rings includes a plurality of crests, wherein a crest is one of a U crown, Y crown and W crown, and each ring extends circumferentially in an undulating fashion along a vertical axis (B-B) perpendicular to a longitudinal axis (A-A);
a marker link extending between a first ring and a second ring of the rings, the marker link including a structure having a hole and a radiopaque material is contained within the hole;
wherein the marker link forms with the first ring a first ring W crown and with the second ring a second ring Y crown, the first right W crown corresponding to a first crest;
wherein a first wave length of the first ring measured from the first crest to a second crest of the first ring, adjacent the first crest, is greater than a second wave length of the first ring measured from the second crest to an adjacent third crest of the first ring; and
wherein the marker link has an aspect ratio (AR) of between about 4 and 5, or about 4.5, where AR is defined as a maximum width of the marker link divided by a wall thickness of the marker link.

9. The medical device of claim 1, wherein the first ring has n crests and n−1 wavelengths where n is at least 6 and not more than 12, and wherein a first and second wavelength measured from the first crest and above and below, respectively, the first crest is greater than the remaining n−3 wavelengths measured between the n−1 crests.

10. The medical device of claim 9, wherein all of the remaining n−3 wavelengths have the same length.

11. The medical device of claim 8, wherein a length of the marker link is about equal to a length of a link connecting the second ring to a third ring.

12. A medical device, comprising:
a balloon catheter having a balloon, the balloon having a distal balloon end and a proximal balloon end;
a thin-walled scaffold crimped to the balloon, the scaffold having proximal and distal end portions formed by a network of rings interconnected by links, wherein each ring has a plurality of crests, wherein a crest is one of a U crown, Y crown and W crown, and each ring extends circumferentially in an undulating fashion along a vertical axis (B-B) perpendicular to a longitudinal axis (A-A);
a marker link extending between a first ring and a second ring of the rings, the marker link including a structure having a hole and a radiopaque material is contained within the hole;
wherein the marker link forms with the first ring a first ring W crown and with the second ring a second ring Y crown, the first ring W crown corresponding to a first crest;
wherein a first wave length of the first ring measured from the first crest to a second crest adjacent the first crest is greater than a second wave length of the first ring measured from the second crest to a third crest adjacent the second crest;
wherein the thin-walled scaffold has an outer diameter of about D-min; and
wherein $$D\text{-min} = (1/\pi) \times [(n \times \text{strut\_width}) + (m \times \text{link\_width})] + 2*t,$$

"n" is the number of struts in a ring,
"strut_width" is the width of a strut,
"m" is the number of links adjoining adjacent rings,
"link_width" is the width of a link, and
"t" is the wall thickness.

13. The medical device of claim 12, wherein a maximum width of the structure measured along axis B-B is greater than a maximum width of a link extending between the second ring and a third ring adjoined to the second ring.

14. The medical device of claim 12, wherein the marker link includes a first link portion extending from the structure to the W crown and a second link structure extending from the Y crown to the structure, wherein a width of the first link portion is greater than a width of the second link portion.

15. The medical device of claim 14, wherein a length of the first length portion is less than a length of the second link portion.

16. The medical device of claim 12, wherein the structure includes a first and second hole containing the radiopaque material, wherein the first and second holes are aligned parallel to the axis A-A.

17. The medical device of claim 1, wherein the marker link has an aspect ratio (AR) of between about 4 and 5, or about 4.5, where AR is defined as a maximum width of the marker link divided by a wall thickness of the marker link.

18. The medical device of claim 17, wherein
a width of the W-crown is greater than a width of the Y crown,
wherein the marker link includes a first link portion extending from the structure to the first ring W crown and a second link portion extending from the second ring Y crown to the structure, and
wherein a width of the first link portion is greater than a width of the second link portion, and/or a length of the first link portion is less than a length of the second link portion.

19. The medical device of claim 17, wherein the thin-walled scaffold has an outer diameter of about D-min; and wherein $$D\text{-min} = (1/\pi) \times [(n \times \text{strut\_width}) + (m \times \text{link\_width})] + 2*t,$$

"n" is the number of struts in a ring,
"strut_width" is the width of a strut,
"m" is the number of links adjoining adjacent rings,
"link_width" is the width of a link, and
"t" is the wall thickness.

20. The medical device of claim 6, wherein the flat portion of the first ring W crown is about 350% to 400% higher than the flat portion of the second ring Y-crown.

21. The medical device of claim 17, wherein the structure includes two radiopaque markers, each having a volume of 3.82E-07 in$^3$.

* * * * *